United States Patent
Endo et al.

(10) Patent No.: US 9,199,921 B2
(45) Date of Patent: Dec. 1, 2015

(54) SILICA-SUPPORTED CATALYST

(75) Inventors: Satoshi Endo, Tokyo (JP); Takaaki Kato, Tokyo (JP)

(73) Assignee: ASAHI KASEI CHEMICALS CORPORATION, Tokyo (JP)

( * ) Notice: Subject to any disclaimer, the term of this patent is extended or adjusted under 35 U.S.C. 154(b) by 0 days.

(21) Appl. No.: 14/112,269

(22) PCT Filed: Apr. 9, 2012

(86) PCT No.: PCT/JP2012/059707
§ 371 (c)(1),
(2), (4) Date: Oct. 17, 2013

(87) PCT Pub. No.: WO2012/144369
PCT Pub. Date: Oct. 26, 2012

(65) Prior Publication Data
US 2014/0194642 A1  Jul. 10, 2014

(30) Foreign Application Priority Data
Apr. 21, 2011 (JP) .................... 2011-095422

(51) Int. Cl.
| | |
|---|---|
| B01J 23/28 | (2006.01) |
| C07C 253/24 | (2006.01) |
| B01J 21/08 | (2006.01) |
| B01J 23/00 | (2006.01) |
| B01J 23/22 | (2006.01) |
| B01J 23/31 | (2006.01) |
| B01J 23/34 | (2006.01) |
| B01J 27/057 | (2006.01) |
| B01J 35/10 | (2006.01) |
| B01J 23/30 | (2006.01) |

(52) U.S. Cl.
CPC ............... *C07C 253/24* (2013.01); *B01J 21/08* (2013.01); *B01J 23/002* (2013.01); *B01J 23/22* (2013.01); *B01J 23/28* (2013.01); *B01J 23/30* (2013.01); *B01J 23/31* (2013.01); *B01J 23/34* (2013.01); *B01J 27/0576* (2013.01); *B01J 35/1009* (2013.01); *B01J 35/1014* (2013.01); *B01J 35/1038* (2013.01); *B01J 2523/00* (2013.01)

(58) Field of Classification Search
CPC ....................................................... B01J 23/28
USPC .................................. 502/249; 558/319, 322
See application file for complete search history.

(56) References Cited

U.S. PATENT DOCUMENTS

| | | |
|---|---|---|
| 5,132,269 A | 7/1992 | Sasaki et al. |
| 5,422,328 A | 6/1995 | Ushikubo et al. |
| 8,772,195 B2 * | 7/2014 | Ishii et al. ............ 502/246 |
| 2003/0017944 A1 | 1/2003 | Hinago et al. |
| 2006/0155139 A1 | 7/2006 | Yanagi et al. |
| 2006/0199730 A1 | 9/2006 | Seely et al. |
| 2008/0248947 A1 | 10/2008 | Zajac et al. |
| 2013/0253217 A1 * | 9/2013 | Ishii et al. ............ 558/319 |
| 2014/0256977 A1 * | 9/2014 | Ishii et al. ............ 560/208 |

FOREIGN PATENT DOCUMENTS

| | | | |
|---|---|---|---|
| EP | 1602405 A1 | | 12/2005 |
| EP | 2392399 A1 | * | 12/2011 |
| JP | 57-75147 A | | 5/1962 |
| JP | 4-118051 A | | 4/1992 |
| JP | 6-285372 A | | 10/1994 |
| JP | 6-316407 A | | 11/1994 |
| JP | 2002-159853 A | | 6/2002 |
| JP | 2002-219362 A | | 8/2002 |
| JP | 2003-220334 A | | 8/2003 |
| JP | 2006-61888 A | | 3/2006 |
| JP | 2009-148749 A | | 7/2009 |
| JP | 2009-285581 A | | 12/2009 |
| JP | 2010-523314 A | | 7/2010 |
| JP | 2010-172851 A | | 8/2010 |
| WO | WO 2004/078344 A1 | | 9/2004 |
| WO | WO 2010087262 A1 | * | 8/2010 |

OTHER PUBLICATIONS

The European Search Report, dated Feb. 19, 2015, issued in the corresponding European Patent Application No. 12774665.9.

* cited by examiner

*Primary Examiner* — Nyeemah A Grazier
(74) *Attorney, Agent, or Firm* — Birch, Stewart, Kolasch & Birch, LLP

(57) ABSTRACT

A silica-supported catalyst used when producing a corresponding unsaturated nitrile in a vapor-phase catalytic ammoxidation reaction of propane or isobutane, the catalyst including a metal oxide represented by the following formula (1), $$MoV_aNb_bX_cT_dZ_eO_n \qquad (1)$$

(wherein X represents at least one or more elements selected from Sb and Te; T represents at least one or more elements selected from Ti, W, Mn, and Bi; Z represents at least one or more elements selected from La, Ce, Yb, and Y; and a, b, c, d, e, and n are in the range of $0.05 \le a \le 0.5$, $0.01 \le b \le 0.5$, $0.001 \le c \le 0.5$, $0 \le d \le 1$, and $0 \le e \le 1$, respectively, and n denotes a value that satisfies an atomic valence)
wherein the silica-supported catalyst has an average pore size of 60 to 120 nm, a total pore volume of 0.15 cm³/g or more, a specific surface area of 5 to 25 m²/g, and a crystallite size of 40 to 250 nm as determined from half width of a (001) peak by X-ray diffraction.

7 Claims, No Drawings

SILICA-SUPPORTED CATALYST

BACKGROUND OF THE INVENTION

1. Field of the Invention

The present invention relates to a silica-supported catalyst used in the production of an unsaturated nitrile.

2. Description of the Related Art

A method in which propylene or isobutylene is subjected to a vapor-phase catalytic oxidation or vapor-phase catalytic ammoxidation reaction to produce a corresponding unsaturated carboxylic acid or unsaturated nitrile is conventionally well known. In recent years, attention has been directed to a method which subjects propane or isobutane instead of propylene or isobutylene to a vapor-phase catalytic oxidation or vapor-phase catalytic ammoxidation to produce the corresponding unsaturated carboxylic acid or unsaturated nitrile. Consequently, as a catalyst for vapor-phase catalytic ammoxidation of propane or isobutane, a variety of oxide catalysts have been proposed.

Patent Literature 1 discloses a silica-supported catalyst having an increased pore volume as a result of using a silica sol and silica powder as silica raw materials.

Patent Literature 2 discloses a composite oxide catalyst used when producing an acrolein or acrylic acid, which has a pore distribution adjusted to a specific range.

Patent Literature 3 discloses a granular porous ammoxidation catalyst in which the pores are controlled to within a specific range in order to improve the yield of the target product.

Patent Literature 1: Japanese Patent Laid-Open No. 2002-219362
Patent Literature 2: Japanese Patent Laid-Open No. 2003-220334
Patent Literature 3: International Publication WO 2004-078344

Problems to be Solved by the Invention

If a silica sol and silica powder are mixed as described in Patent Literature 1, although the pore volume can be increased, the average pore size does not increase. Consequently, although an improvement in fluidity is seen due to the increase in pore volume, this does not lead to an improvement in the yield of the target product. Further, Patent Literature 1 contains no description about combustion of the raw material ammonia, which is one of the problems when producing a nitrile by subjecting an alkane to vapor-phase catalytic ammoxidation.

Patent Literature 2 describes increasing the yield by controlling pore size. However, since fluidity can be thought to be poor in view of the description of hammer molding, it can be understood that the catalyst is a catalyst for a fixed-bed reaction, and is not suited to a fluidized-bed reaction.

The method described in Patent Literature 3 improves the yield of the target product by setting the pore size in a specific range. Based on supplementary experiments carried out according to the method described in Patent Literature 3, the present inventors discovered that although the pore distribution of the obtained catalyst satisfies "an integral volume of pores having a pore size of 80 Å or less of 20% or less based on the total pore volume of the catalyst, and an integral volume of pores having a pore size of 1,000 Å or more of 20% or less based on the total pore volume of the catalyst", the pores were distributed toward the comparatively small pore size between 80 and 1,000 Å. For an alkane ammoxidation catalyst having a strong oxidizing power, small-sized pores are not suitable because the combustion of the raw material ammonia and/or a degradation reaction of the target product tend to proceed. Further, since the crystallite size is not defined, it can be thought that the improvement in yield is not sufficient.

It is an object of the present invention to, in view of the above-described circumstances, provide a catalyst having a low rate of combustion of the raw material ammonia, and a high target product yield.

Means for Solving the Problems

Under such circumstances, as a result of extensive research to solve the above-described problems in the conventional art, the present inventors discovered that by using a silica-supported catalyst that contains at least Mo, V, and Nb, and that has a value for specific physical properties, such as average pore size, in a proper range, a target product yield is greatly increased, and further, that since combustion of raw material ammonia can be suppressed, an unsaturated nitrile can be efficiently produced, thereby completing the present invention.

Namely, the present invention is as follows.

[1] A silica-supported catalyst used when producing a corresponding unsaturated nitrile in a vapor-phase catalytic ammoxidation reaction of propane or isobutane, the catalyst comprising a metal oxide represented by the following formula (I),

$$MoV_aNb_bX_cT_dZ_eO_n \quad (1)$$

(wherein X represents at least one or more elements selected from Sb and Te; T represents at least one or more elements selected from Ti, W, Mn, and Bi; Z represents at least one or more elements selected from La, Ce, Yb, and Y; and a, b, c, d and e are in the range of $0.05 \leq a \leq 0.5$, $0.01 \leq b \leq 0.5$, $0.001 \leq c \leq 0.5$, $0 \leq d \leq 1$, and $0 \leq e \leq 1$, respectively, and n denotes a value that satisfies an atomic valence)

wherein the silica-supported catalyst has an average pore size of 60 to 120 nm, a total pore volume of 0.15 cm$^3$/g or more, a specific surface area of 5 to 25 m$^2$/g, and a crystallite size of 40 to 250 nm as determined from half width of a (001) peak by X-ray diffraction.

[2] The silica-supported catalyst according to the above [1], wherein a pore volume of pores having a pore size of less than 60 nm based on total pore volume is less than 30%, and a pore volume of pores having a pore size exceeding 120 nm based on total pore volume is less than 30%.

[3] The silica-supported catalyst according to the above [1] or [2], wherein a support amount of silica is 20 to 70% by mass based on total mass of the catalyst formed from a metal oxide and silica.

[4] A method for producing a silica-supported catalyst, comprising the steps of:

(I) preparing a raw material-prepared solution containing Mo, V, Nb, X, T, and Z, wherein an atomic ratio a of V to one Mo atom is $0.05 \leq a \leq 0.5$, an atomic ratio b of Nb to one Mo atom is $0.01 \leq b \leq 0.5$, an atomic ratio c of X to one Mo atom is $0.001 \leq c \leq 0.5$, an atomic ratio d of T to one Mo atom is $0 \leq d \leq 1$, and an atomic ratio e of Z to one Mo atom is $0 \leq e \leq 1$;

(II) drying the raw material-prepared solution to obtain a dry powder;

(III) pre-stage calcining the dry powder at 200 to 400° C. to obtain a pre-stage calcined body; and (IV) main-calcining the pre-stage calcined body at 600 to 750° C. to obtain a calcined body, wherein the raw material-prepared solution comprises 0 to 30% by mass based on total mass of the silica raw materials of (i) a silica sol having an average primary particle size of 3 nm or more and less than 20 nm, 30 to 70% by mass based on total mass of the silica raw materials of (ii) a silica sol having an average primary particle size of 20 nm or more and 100 nm or less, and 30 to 70% by mass based on total mass of the silica raw materials of silica powder having an average primary particle size of 50 nm or less, and wherein a total of the silica sol (i), the silica sol (ii), and the silica powder is 100% by mass based on silica.

[5] A method for producing a corresponding unsaturated nitrile by performing a vapor-phase catalytic ammoxidation reaction of propane or isobutane using the silica-supported catalyst according to any one of the above [1] to [3].

Advantages of the Invention

The present invention can provide a catalyst having a low rate of combustion of ammonia, and a high target product yield.

DETAILED DESCRIPTION OF THE PREFERRED EMBODIMENT

Hereinafter, an embodiment of the present invention (hereinafter, referred to as "the present embodiment") will be described in detail. Note that the present invention is not limited to the following embodiment, and many variations may be made within the scope of the present invention.

The silica-supported catalyst according to the present embodiment is a silica-supported catalyst used when producing a corresponding unsaturated nitrile in a vapor-phase catalytic ammoxidation reaction of propane or isobutane, including a metal oxide represented by the following formula (I), $$MoV_aNb_bX_cT_dZ_eO_n \qquad (1)$$

(wherein X represents at least one or more elements selected from Sb and Te; T represents at least one or more elements selected from Ti, W, Mn, and Bi; Z represents at least one or more elements selected from La, Ce, Yb, and Y; and a, b, c, d, e, and n are in the range of $0.05 \leq a \leq 0.5$, $0.01 \leq b \leq 0.5$, $0.001 \leq c \leq 0.5$, $0 \leq d \leq 1$, and $0 \leq e \leq 1$, respectively, and n denotes a value that satisfies an atomic valence)

wherein the silica-supported catalyst has an average pore size of 60 to 120 nm, a total pore volume of 0.15 cm³/g or more, a specific surface area of 5 to 25 m²/g, and a crystallite size of 40 to 250 nm as determined from half width of a (001) peak by X-ray diffraction.

Since the silica-supported catalyst according to the present embodiment has an optimized metal composition ratio for the metal oxide included in the catalyst, it has a good catalytic performance. Although the method for producing the silica-supported catalyst according to the present embodiment is not especially limited, it is preferred to produce the silica-supported catalyst based on the following method that includes steps (I) to (IV).

A method for producing a silica-supported catalyst, including the steps of:

(I) preparing a raw material-prepared solution containing Mo, V, Nb, X, T, and Z, wherein an atomic ratio a of V to one Mo atom is $0.05 \leq a \leq 0.5$, an atomic ratio b of Sb to one Mo atom is $0.01 \leq b \leq 0.5$, an atomic ratio c of Nb to one Mo atom is $0.001 \leq c \leq 0.5$, an atomic ratio d of W to one Mo atom is $0 \leq d \leq 1$, and an atomic ratio e of Z to one Mo atom is $0 \leq e \leq 1$;

(II) drying the raw material-prepared solution to obtain a dry powder;

(III) pre-stage calcining the dry powder at 200 to 400° C. to obtain a pre-stage calcined body; and (IV) main-calcining the pre-stage calcined body at 600 to 750° C. to obtain a calcined body, wherein the raw material-prepared solution comprises 0 to 30% by mass based on total mass of the silica raw materials of (i) a silica sol having an average primary particle size of 3 nm or more and less than 20 nm, 30 to 70% by mass based on total mass of the silica raw materials of (ii) a silica sol having an average primary particle size of 20 nm or more and less than 100 nm, and 30 to 70% by mass based on total mass of the silica raw materials of silica powder having an average primary particle size of 50 nm or less, and wherein a total of the silica sol (i), the silica sol (ii), and the silica powder is 100% by mass based on silica.

(Step (I) Raw Material Formulation Step)

Step (I) is a step of preparing a raw material-prepared solution containing Mo, V, Nb, X, T, and Z, wherein an atomic ratio a of V to one Mo atom is $0.05 \leq a \leq 0.5$, an atomic ratio b of Nb to one Mo atom is $0.01 \leq b \leq 0.5$, an atomic ratio c of X to one Mo atom is $0.001 \leq c \leq 0.5$, an atomic ratio d of T to one Mo atom is $0 \leq d \leq 1$, and an atomic ratio e of Z to one Mo atom is $0 \leq e \leq 1$.

In the raw material formulation step, a raw material-prepared solution is obtained by dissolving or dispersing the constituent elements of the silica-supported catalyst in a solvent and/or dispersion medium in a specific ratio. Generally, water can be used as the raw material-prepared solution solvent. The raw material-prepared solution includes Mo, V, Nb, X, T, and Z (in which X represents at least one or more elements selected from Sb and Te, T represents at least one or more elements selected from Ti, W, Mn, and Bi, and Z represents at least one or more elements selected from La, Ce, Yb, and Y). As the raw materials of the raw material-prepared solution, a salt or a compound containing the constituent elements of the silica-supported catalyst can be used.

As a raw material for Mo, for example, ammonium heptamolybdate [$(NH_4)_6Mo_7O_{24} \cdot 4H_2O$], molybdenum trioxide [$MoO_3$], phosphorus molybdate [$H_3PMo_{12}O_{40}$], silicon molybdate [$H_4SiMo_{12}O_{40}$], molybdenum pentachloride [$MoCl_5$], and the like can be used. Particularly preferred is ammonium heptamolybdate [$(NH_4)_6Mo_7O_{24} \cdot 4H_2O$]

As a raw material for V, for example, ammonium metavanadate [$NH_4VO_3$], vanadium pentoxide [$V_2O_5$], vanadium chlorides [$VCl_4$, $VCl_3$] and the like can be used. Particularly preferred is ammonium metavanadate [$NH_4VO_3$].

As raw materials for Nb, for example, niobic acid, an inorganic niobate and an organic niobate can be used. In particular, niobic acid is preferable. Niobic acid is represented by $Nb_2O_5 \cdot nH_2O$ and is also referred to as niobium hydroxide or niobium oxide hydrate. Further, an Nb raw material solution in which a molar ratio of dicarboxylic acid/niobium is 1 to 4 is also preferably used, and as the dicarboxylic acid, oxalic acid is preferable.

Raw materials for X (Sb and Te) are not particularly limited as long as the raw materials contain these elements. A compound containing these elements and a solution in which the metal of these elements is solubilized in an appropriate reagent can be used. As the compound containing these elements, an ammonium salt, a nitrate, a carboxylate, an ammonium salt of a carboxylic acid, a peroxocarboxylate, an ammonium salt of a peroxocarboxylic acid, a halogenated ammonium salt, a halide, acetyl acetate, and an alkoxide of these elements can usually be used. Preferably, an aqueous raw material such as a nitrate, and a carboxylate can be used.

Raw materials for T (Ti, W, Mn and Bi) are not particularly limited as long as the raw materials contain these elements. A compound containing these elements and a solution in which the metal of these elements is solubilized in an appropriate reagent can be used. As the compound containing these elements, an ammonium salt, a nitrate, a carboxylate, an ammonium salt of a carboxylic acid, a peroxocarboxylate, an ammonium salt of a peroxocarboxylic acid, a halogenated ammonium salt, a halide, acetyl acetate, and an alkoxide of these elements can usually be used. Preferably, an aqueous raw material such as a nitrate, and a carboxylate can be used.

Raw materials for Z (La, Ce, Yb and Y) are not particularly limited as long as the raw materials contain these elements. A compound containing these elements and a solution in which the metal of these elements is solubilized in an appropriate reagent can be used. As the compound containing these elements, an ammonium salt, a nitrate, a carboxylate, an ammonium salt of a carboxylic acid, a peroxocarboxylate, an ammonium salt of a peroxocarboxylic acid, a halogenated ammonium salt, a halide, acetyl acetate, and an alkoxide of these elements can usually be used. Preferably, an aqueous raw material such as a nitrate, and a carboxylate can be used.

In the formulation of the raw material, the procedure of dissolving the raw materials for the catalyst forming elements, the procedure of mixing the raw material, or the procedure of dispersing the raw material is not particularly limited. The raw materials may be dissolved, mixed, or dispersed in the same aqueous medium. Alternatively, the raw materials may be separately dissolved, mixed, or dispersed in an aqueous medium, and the aqueous mediums may be mixed. When necessary, heating and/or stirring may be performed.

In the silica-supported catalyst, one of important points is that the component Z is uniformly distributed in the catalyst particles. Here, uniformity means that the distribution of the component Z in the catalyst particles is not uneven. Preferably, the "uniformity" means that not less than 80% of oxide particles containing the component Z (mass ratio) exist in the catalyst particles as fine particles having a particle size of not more than 1 µm. A more suitable definition of "uniformity" is that when the cross section of the catalyst particle is subjected to composition analysis, a dispersion value (a value obtained by dividing the standard deviation by the average value) of a signal intensity ratio of the component Z to Si is in the range of 0 to 0.5. Here, the dispersion value is shown by "Dx."

An ordinary composition analysis method can be used for the composition analysis. For example, SEM-EDX, XPS, SIMS, EPMA, and the like can be used. Preferably, the EPMA can be used. Here, the EPMA is commonly called an Electron Probe X-ray Microanalyzer (the term X-ray may be omitted to refer to the apparatus). The analysis apparatus is an apparatus in which a characteristic X-ray obtained by irradiating a substance with an accelerated electron beam is observed to perform the composition analysis of the fine region (spot) irradiated with the electron beam. By the EPMA, usually, about the cross section of the solid particle such as catalyst particles and carrier particles, information on a specific element such as the concentration distribution and change in the composition can be obtained.

The dispersion value (Dx) of the intensity ratio of the component Z to Si analyzed by the EPMA is a value obtained by measuring the cross section of the particle to be measured and performing calculation according to an ordinary method for plane analysis of the cross section of the particle by the EPMA, which is performed in the field of the catalyst, as follows. Namely, first, distribution of X-ray peak intensity of Si (the number of count ISi) in any position (x, y) in the cross section of the catalyst particle is measured so that the entire cross section of the catalyst particle is covered. Next, similarly, distribution of X-ray peak intensity (the number of count IX) of the component Z is measured so that the entire cross section of the catalyst particle is covered. Based on the obtained series of data (x, y, ISi, IX) on Si and the component Z, a peak intensity ratio IR of the component Z to Si (IR=IX/ISi) in the same position (x, y) is determined, and the simple average (IR)av and standard deviation S of IR are determined. The value obtained by dividing the standard deviation S by the simple average (IR)av is defined as the dispersion value (Dx). At this time, the simple average and the standard deviation may be determined by an ordinary method. In the present specification, the term "silica-supported catalyst" (sometimes simply referred to as "catalyst") includes a catalyst from which protruding objects formed on the particle surface have been removed from the calcined body after the main-calcination. Since the measurement of the dispersion value relies on observation of the cross section, and is not influenced by the state of the surface, the same value will be exhibited after main-calcination even if the measurement is carried out before the step of removing the protruding objects.

Preferably, in order to avoid uncertainty of data due to an edge effect of the cross section of the particle in the measurement, a region that is 10% of the cross section area in the cross section of the catalyst particle and corresponds to the outer periphery of the particle is excluded, a region of 90% from the center in the cross section of the catalyst particle is used as an effective region, and the data of the effective region is calculated. Of course, from the beginning, the plane analysis by the EPMA may be performed on only the inside of the cross section of the catalyst particle from which 10% of the region corresponding to the outer periphery of the particle is excluded, and the dispersion value Dx may be determined from the data.

Since the catalyst according to the present embodiment is a silica-supported catalyst in which a metal oxide is supported on silica, the raw material-prepared solution is prepared so as to include a silica raw material. From the perspective of controlling the average pore size of the catalyst with a silica sol to 60 to 120 nm, it is preferred that the raw material-prepared solution includes 0 to 30% by mass based on total mass of the silica raw materials of (i) a silica sol having an average primary particle size of 3 nm or more and less than 20 nm, 30 to 70% by mass based on total mass of the silica raw materials of (ii) a silica sol having an average primary particle size of 20 nm or more and less than 100 nm, and 30 to 70% by mass based on total mass of the silica raw materials of silica powder having an average primary particle size of 50 nm or less, in which a total of the silica sol (i), the silica sol (ii), and the silica powder is 100% by mass based on silica. The order in which these silica raw materials are added to the raw material-prepared solution is not especially limited, and these silica raw materials may be mixed before adding to the raw material-prepared solution. Although the reason is not clear, if a specific content of the silica sol (i), the silica sol (ii), and the silica powder is used, based on experimentation the present inventors learned that a catalyst having a large average pore size and a high wear resistance strength can be produced.

It is thought that if the silica sol (i) and silica sol (ii) are used, small-diameter silica particles come in between large-diameter silica particles, so that there is an effect of reducing fine pores in the catalyst. In addition, it is thought that by adding the silica powder, the silica sols are prevented from aggregating, so that there is an effect of increasing large pores. Since the catalyst according to the present embodiment has a larger average pore size than a conventional catalyst, it is presumed that the reaction temperature becomes uniform due to an increase in the rate of diffusion of the raw material ammonia and target product in the catalyst particles and/or increase in the diffusion of heat in the catalyst particles, whereby combustion of the raw material ammonia and degradation of the target product can be suppressed.

Metals included as impurities in the silica raw materials may affect the performance of the produced silica-supported catalyst. An example of impurities in the silica raw material is sodium. The amount of sodium is preferably 0.02 atoms or less per 100 atoms of silicon, and more preferably 0.01 atoms or less. If more than 0.02 atoms per 100 atoms of silicon are included, when the obtained silica-supported catalyst is used in the ammoxidation reaction, the raw materials and/or target product tend to undergo a degradation reaction.

When producing an unsaturated nitrile by vapor-phase ammoxidation of an alkane, due to the low reactivity of alkanes, the reaction is carried out in the presence of a catalyst having a strong oxidizing power and/or at a high temperature. Consequently, combustion of the raw material ammonia and degradation reaction of the target product tend to occur. If combustion of the raw material ammonia occurs, there will be a shortage of ammonia for use in the production of the unsaturated nitrile, so that a large amount of ammonia needs to be supplied with respect to the alkane. Consequently, productivity deteriorates. In the present embodiment, by suppressing combustion of the raw material ammonia, the unsaturated nitrile can be efficiently produced. Further, obviously, by suppressing degradation of the unsaturated nitrile, which is the target product, the yield improves.

If the average pore size of the catalyst is less than 60 nm, combustion of the raw material ammonia and degradation reaction of the target product tend to occur. On the other hand, if the average pore size of the catalyst is more than 120 nm, the wear resistance strength deteriorates, so that the catalyst is not suitable for a fluidized-bed reaction. From the above-described perspectives, the average pore size of the catalyst according to the present embodiment is adjusted to a range of 60 to 120 nm, and is preferably adjusted to a range of 65 to 100 nm.

Based on supplementary experiments carried out by the present inventors regarding conventional catalysts used in an ammoxidation reaction of an olefin, such as propylene or isoprene, the pore volume of pores having a pore size of less than 60 nm was found to be 30% or more of the total pore volume. For an alkane ammoxidation reaction, since the oxidizing power of the alkane is strong, if the pore volume of pores having a pore size of less than 60 nm is 30% or more of the total pore volume, it is thought that combustion of the raw material ammonia and/or degradation reaction of the target product tend to occur. Therefore, for an alkane ammoxidation reaction, it is preferred that the catalyst has a comparatively large size and that the pore sizes are uniform. On the other hand, by setting the pore volume of pores having a pore size of more than 120 nm to less than 30% of the total pore volume, the wear resistance strength is large, so that the catalyst tends to be suitable for use in a fluidized-bed reaction. From the above-described perspectives, it is preferred that the silica-supported catalyst according to the present embodiment has a pore volume of pores having a pore size of less than 60 nm of less than 30% of the total pore volume, and a pore volume of pores having a pore size of more than 120 nm of less than 30% of the total pore volume.

To produce such a catalyst, it is preferred to use silica sols having different particle sizes, and control the sintering of the silica by calcining at 600 to 750° C. It is preferred to carry out the calcining at 600° C. or more, because the sintering of the silica proceeds sufficiently, and the pore volume of pores having a particle size of 60 nm or more increases.

From the perspective of improving the strength of the catalyst, it is preferred that the support amount of silica included in the catalyst is 20% by mass or more based on the total mass of the catalyst formed from a metal oxide and silica. From the perspective of imparting sufficient activity, the support amount of support silica included in the catalyst is preferably 70% by mass or less, and more preferably 40 to 65% by mass, based on the total mass.

As the raw material for the silica carrier, only silica sol may be used. Alternatively, part of the raw material can be replaced by powder silica. If the powder silica is used as the raw material for the silica carrier, an effect of improving the activity of the catalyst and/or yield of the target object is expected. On the other hand, if only the powder silica is used without using the silica sol to prepare the catalyst, the resistance to wear of the catalyst is remarkably reduced. In the present embodiment, the term "powder silica" indicates fine particles of solid $SiO_2$. If the primary particle size of the silica is excessively large, the catalyst to be obtained is likely to be fragile. Accordingly, the powder silica of a nanometer size is preferred. The powder silica is preferably produced by a high-temperature method.

From the viewpoint of easiness in addition to and mixing with the raw material-prepared solution, the powder silica is preferably dispersed in advance in water. A method of dispersing the powder silica in water is not particularly limited, and the power silica can be dispersed using an ordinary homogenizer, homomixer, or ultrasonic vibrator alone or in combination thereof. The primary shape of the powder silica at this time may be spherical, or non-spherical.

The average primary particle size of the silica sol and the silica powder, which are the support raw materials, can be determined by a BET method (a BET adsorption isotherm method). Silica that is generally available commercially can be thought to have a distribution width in which the average primary particle size is about in the center. In order to sufficiently exhibit an ammonia combustion suppression effect, it is preferred that the standard deviation of each silica particle size distribution is as small as possible. Specifically, it is preferred that the standard deviation is not greater than 30% of the average primary particle size.

To control the average pore size of the catalyst, it is effective to change the average primary particle size of the silica sol. Generally, if the average primary particle size of a silica sol is increased, the strength of the obtained catalyst tends to decrease. On the other hand, since a high strength is desirable for an industrial fluidized-bed catalyst, conventionally a silica sol having an average primary particle size of a dozen or so nm is usually used as a silica raw material. When a catalyst is produced using such a silica sol based on a conventional method, the average pore size is about 20 to 50 nm, which does not satisfy the range of 60 to 120 nm for average pore size defined in the present embodiment. Further, the yield is also not sufficient. By changing the calcining conditions, the average pore size can be controlled. If the calcining temperature is increased and/or the calcining time lengthened, the average pore size tends to increase. However, if the average pore size is controlled by changing the calcining conditions, the specific surface area and/or crystallite size also change. Therefore, it is difficult to control the average pore size, specific surface area, and crystallite size just based on the calcining conditions. As described above, with the catalyst production methods described above in the Description of the Related Art, it is essentially impossible to obtain a catalyst that satisfies average pore size, specific surface area and/or crystallite size. It is preferred to control the average pore size based on a method using silica sols having different average primary particle sizes, since the specific surface area and/or crystallite size can be controlled based on the calcining conditions. The specific surface area and the crystallite size can be controlled by regulating the calcining conditions, because the temperature region in which the sintering of silica, which has a large impact on specific surface area, is different from the temperature region in which the crystals grow.

The means for controlling the average pore size of the catalyst according to the present embodiment to the proper range is not especially limited. Any means may be used, as long as the average pore size can be controlled to the proper range. Examples of the means for controlling the average pore size of the catalyst include a method in which the average primary particle size of the above-described silica sols, which are silica raw materials, a method in which silica powder is used for a part of the silica raw materials, a method in which the ratio between the silica support and the metal oxide in the catalyst is changed and the like.

It is preferred that the raw material-prepared solution contains, as a part of the silica raw materials, 30 to 70% by mass of silica powder having an average primary particle size of 50 nm or less based on silica. In the present embodiment, "based on silica" is a ratio based on the total weight of the silica sols and silica powder. It is more preferred that the average primary particle size of the silica powder is 10 to 20 nm. Further, it is more preferred that the amount of silica powder is 30 to 50% by mass based on silica. If silica powder is used, the specific surface area of the catalyst increases. To control the specific surface area and the crystallite size to the proper range, it is preferred to carry out the main calcining at a calcining temperature of 640 to 750° C., a calcining time of 1 to 20 hours, and an average rate of temperature decrease after the main calcining has finished of 0.05 to 20° C./min.

When controlling the average pore size by changing the ratio between the support amount of silica and the metal oxide amount in the catalyst, it is preferred to set the support amount of silica to 20 to 70% by mass based on the total mass of catalyst formed from the metal oxide and silica, and more preferably to 40 to 60% by mass. Generally, if the support amount of silica is decreased, the average pore size shifts toward the larger pore size side, so that the specific surface area decreases. To control the specific surface area and the crystallite size to the proper range, it is preferred to carry out the main calcining at a calcining temperature of 600 to 700° C., a calcining time of 0.1 to 5 hours, and an average rate of temperature decrease after the main calcining has finished of 0.5 to 50° C./min.

Examples of the method to measure the catalyst pore distribution include gas adsorption, mercury intrusion and the like. However, the value depends on the measurement method. The pore distribution value of the catalyst according to the present embodiment is determined based on a mercury intrusion method (using the Pore Master GT, manufactured by Quantachrome Instruments). This mercury intrusion method measures the pore size distribution based on the relationship between pressure and intrusion amount when mercury is injected into the interior of the catalyst particles. Using the obtained data as primary data, an integral curve of the pore volume as a function of pore size calculated based on the assumption that the pores have a cylindrical shape is obtained. Values obtained by taking the first derivative of this integral curve of the pore volume with respect to the pore size are plotted against the corresponding pore size, and the resultant graph is generally called "pore distribution". Specifically, 0.4 to 0.6 g of a sample (catalyst) is fed into a dilatometer (expansion gauge), the contents thereof are evacuated to 6.67 Pa or less with a vacuum pump, and then mercury is injected. Next, the dilatometer is placed in an autoclave. The decrease of the mercury liquid level while gradually increasing the pressure from ordinary pressure to 413 MPa is tracked, and the pore distribution is measured based on the changes in pressure and the mercury liquid level (injected amount of mercury into the catalyst pores).

For catalysts, when a mercury intrusion method is used the gap between the catalyst particles is measured as pores from several tens of thousand Å to several hundreds of thousand Å. Therefore, pores that are 200 nm or less are added to the integral volume. Further, since the lower measurement limit of the pore size is 6 nm, pores that are 6 nm or more are added to the integral volume. Therefore, in the present embodiment, the total pore volume is taken as the integral volume of pores having a pore size of 6 nm or more and 200 nm or less.

The total pore volume of the catalyst according to the present embodiment is, from the perspective of fluidity in the fluidized-bed reaction, 0.15 cm$^3$/g or more. If the total pore volume is less than 0.15 cm$^3$/g, fluidity decreases, which causes the yield to decrease due to unevenness in the reaction temperature. The total pore volume tends to increase the greater that the average pore size is and/or the greater that the specific surface area is. Examples of means for adjusting the total pore volume include a method in which the average pore size is increased using silica sols having different particle sizes and/or a method in which the specific surface area is increased by decreasing the calcining temperature and/or shortening the calcining time in the calcining step.

Calculation of the average pore size of the catalyst is carried out using formula (I) based on the assumption that the pores are cylindrical.

$$D=4V/S \qquad (i)$$

Here, D represents the average pore size (m), V represents the total pore volume (m$^3$/g), and S represents the specific surface area (m$^2$/g).

Hereinafter, the raw material formulating step will be described using an example in which the solvent and/or disperse medium is water, and the raw material-prepared solution for the silica-supported catalyst containing an Mo compound, a V compound, an Nb compound, a X compound, a T compound and a Z compound is prepared.

The Mo compound, the V compound, the X compound, and the component Z compound are added to water, and the solution is heated to prepare a raw material-prepared solution (A). The heating temperature and heating time during preparation of the raw material-prepared solution (A) are preferably adjusted so that the raw material compound is sufficiently dissolved. The heating temperature is preferably 70° C. to 100° C., and the heating time is preferably 30 minutes to 5 hours. The number of rotation of stirring during heating is similarly adjusted to the number of rotation at which the raw material is easily dissolved. In the case where the raw material is a metal salt, the state of stirring is preferably kept from the viewpoint of sufficiently dissolving the metal salt. At this time, the inside of a container may be an air atmosphere. From the viewpoint of adjusting the oxidation number of the complex oxide catalyst to be obtained, a nitrogen atmosphere can be used. The state where heating of the raw material-prepared solution (A) is completed is called a raw material-prepared solution (A'). The raw material-prepared solution (A') is preferably kept at a temperature of not less than 20° C. and not more than 80° C., and more preferably not less than 40° C. and not more than 80° C. At a temperature of the raw material-prepared solution (A') less than 20° C., a metal kind dissolved in the raw material-prepared solution (A') may be precipitated. After the heating of the raw material-prepared solution (A) has finished, a silica sol is added as a support raw material. When adding two kinds or more of silica sol having different average primary particle sizes, the order in which these are added is not limited, and these silica sols may be mixed prior to adding to the raw material-prepared solution. It is preferred that the temperature of a raw material-prepared solution (A') when adding the silica sols is not more than 80° C. If the silica sols are added at a temperature exceeding 80° C., the stability of the silica sols can weaken, so that the raw material-prepared solution can turn into a gel. Although the timing for adding the silica sols may be when starting the below-described aging, during the aging, or immediately before drying the raw material-prepared solution, it is preferred to add silica sol during the raw material-prepared solution (A') state. In addition, from the perspective of adjusting the oxidation number of the obtained metal oxide, it is preferred to add a suitable amount of hydrogen peroxide to the raw material-prepared solution (A') as necessary. The timing for adding the hydrogen peroxide may be when adding the silica sol to the raw material-prepared solution (A'), during the adjustment of the raw material-prepared solution (A'), or before or after adding the silica sol. At this stage, from the perspective of adjusting the oxidation number of the obtained oxide catalyst to a proper range, the added amount of hydrogen peroxide is preferably 0.01 to 5, more preferably 0.5 to 3, and even more preferably 1 to 2.5, based on $H_2O_2/Sb$ (molar ratio).

The heating temperature and heating time after the hydrogen peroxide solution is added to the raw material-prepared solution (A') is preferably adjusted so that liquid phase oxidation reaction by the hydrogen peroxide solution can sufficiently progress. The heating temperature is preferably 30° C. to 70° C., and the heating time is preferably 5 minutes to 4 hours. Similarly, the number of rotation of stirring during heating is adjusted at the number of rotation that the liquid phase oxidation reaction by the hydrogen peroxide solution easily progresses. From the viewpoint of sufficient progression of the liquid phase oxidation reaction by the hydrogen peroxide solution, stirring is preferably continued during the heating. The thus-prepared aqueous mixed-solution is called a raw material-prepared solution (A").

Next, the Nb compound and dicarboxylic acid are heated and stirred in water to prepare a mixed-solution ($B_0$). Examples of dicarboxylic acid include oxalic acid [$(COOH)_2$]. A hydrogen peroxide solution is preferably added to the mixed-solution ($B_0$) to prepare a raw material-prepared solution (C). At this time, $H_2O_2/Nb$ (molar ratio) is preferably 0.5 to 20, and more preferably 1 to 10 from the viewpoint of forming a complex with the Nb compound and stabilizing the complex in a dissolved state, properly adjusting the state of oxidation and reduction of the catalyst forming elements, and optimizing the ability of the catalyst to be obtained.

Depending on a target composition, the raw material-prepared solution (A"), the raw material-prepared solution (C), the T compound, and the powder silica are suitably mixed to obtain a raw material-prepared solution (D). The obtained raw material-prepared solution (D) is aged to obtain a raw material-prepared solution. The powder silica used here can be added as it is. More preferably, the power silica is added as an aqueous solution in which the powder silica is dispersed in water. The concentration of the powder silica in the water at this time is preferably 1 to 30% by mass, and more preferably 3 to 20% by mass. At a concentration of the powder silica less than 1% by mass, the viscosity of a slurry is excessively low. For this reason, the shape of the particle to be obtained may be distorted, and depressions may be likely to be produced in the catalyst particles. On the other hand, at a concentration of the powder silica more than 30% by mass, the viscosity of the raw material-prepared solution is excessively high, and the raw material-prepared solution may be gelated to produce cloggings within a pipe. As a result, it may be difficult to obtain a dry powder, and the ability of the catalyst may be reduced.

Aging of the raw material-prepared solution (D) means to leave standstill or stir the raw material-prepared solution (D) for a predetermined time. When industrially producing the silica-supported catalyst, the spray dryer has a rate-limiting treatment speed, so that it can take some time for the spray drying of all the mixed solution to finish after a part of the raw material-prepared solution (D) has been spray dried. During this dry spraying, aging of the mixed solution that has not been spray dried can be continued. Specifically, the aging time not only includes the aging time before spray drying, but also the time from start to finish of the spray drying.

A catalyst supported by silica is preferred in terms of, for example, the perspective of sufficiently dissolving and/or dispersing the compound including the catalyst constituent elements, the perspective of appropriately adjusting the redox state of the catalyst constituent elements, the perspective of setting the particle shape and/or strength of the obtained catalyst to a preferred state, and the perspective of improving the catalytic performance of the obtained composite oxide. The silica sol can be properly added. An aqueous dispersion of the silica powder can be used as a portion of the silica sol. The aqueous dispersion of silica powder can also appropriately be added.

The raw material formulating step can be repeatedly performed depending on the amount of production.

The raw material formulating step in the present embodiment preferably comprises the following steps (a) to (d):
(a) a step of preparing a raw material-prepared solution containing Mo, V, X, and the component Z;
(b) a step of adding silica sol and a hydrogen peroxide solution to the raw material-prepared solution obtained in the step (a);
(c) a step of mixing an aqueous solution containing Nb, dicarboxylic acid and a hydrogen peroxide solution and a T compound with the solution obtained in the step (b); and
(d) a step of adding a powder silica-containing suspension to the solution obtained in the step (c), and aging the solution.

(Step (II) Drying Step)

Step (II) is a step of drying the raw material-prepared solution to obtain a dry powder.

The slurry raw material-prepared solution subjected to the raw material formulating step is dried to obtain a dry powder. The drying can be performed by a known method. For example, the drying can be performed by spray drying or evaporation to dryness. In the case where a fluidized bed reaction method is used for the vapor-phase catalytic ammoxidation reaction, use of spray drying is preferred because it is preferable that a micro spherical dry powder be obtained from the viewpoint of preferable fluidity within the reactor. Spraying in the spray drying method can be performed by a centrifugal system, a two-fluid-nozzle system, or a high-pressure nozzle system. Air heated by steam, and an electric heater or the like can be used as a heat source for drying. The temperature at the inlet of the dryer of a spray dryer is preferably 150 to 300° C. from the viewpoint of providing a preferred shape and/or strength of the catalyst particles to be obtained, and improving the ability of the catalyst of the complex oxide to be obtained. The temperature at the outlet of the dryer is preferably 100 to 160° C.

Preferably, the spray rate, the feeding rate of the raw material-prepared solution, and the number of rotation of an atomizer in the case of a centrifugal type are adjusted so that the dry powder to be obtained has a suitable size. The average particle size of the dry powder is preferably 5 μm to 200 μm, and more preferably 10 to 150 μm.

The average particle size of the dry powder can be determined as follows: according to JIS R 1629-1997 "a Particle Size Distribution Measuring Method By a Laser Diffraction Scattering Method for a Fine Ceramic Raw Material," particle size distribution is measured, and averaged based on the volume. More specifically, part of the dry powder is calcined in the air at 400° C. for 1 hour, and the obtained particles are measured using a laser diffraction scattering particle size distribution measurement apparatus LS230 made by Beckman Coulter, Inc.

The average particle size is measured after part of the dry powder is "calcined in the air at 400° C. for 1 hour," because the dry powder is prevented from being dissolved in water. Namely, "calcination in the air at 400° C. for 1 hour" is mainly for measurement, and has nothing to do with the calcining step described later. It may be thought that the particle size is substantially not changed before and after the calcination.

More specifically, the average particle size of the dry powder is measured according to the manual attached to the laser diffraction scattering particle size distribution measurement apparatus (made by Beckman Coulter, Inc., trade name "LS230") as follows. First, after background measurement (Run Speed 60) is performed, 0.2 g of the particles is weighed and placed in a screw cap tube having a proper size, and 10 cc of water is added. The screw cap tube is capped (tightly closed), and sufficiently shaken to disperse the particles in water. 300 W of an ultrasonic wave is applied by the apparatus, and the screw cap tube is sufficiently shaken again. Subsequently, while the ultrasonic wave is applied, the particles dispersed in water are injected into the apparatus main body using a pipette so as to obtain a proper concentration (concentration of 10, PIDS of 60). When the concentration displayed is stabilized, application of the ultrasonic wave is stopped. The screw cap tube is left as it is for 10 seconds, and the measurement is started (measurement time of 90 seconds). The value of a median size in the measurement result is defined as the average particle size.

((III) Pre-stage Calcination Step and (IV) Main Calcination Step)

Step (III) is a step of pre-stage calcining the dry powder at 200 to 400° C. to obtain a pre-stage calcined product.

Step (IV) is a step of main-calcining the pre-stage calcined product at 600 to 750° C. to obtain a calcined product.

Herein, step (III) and step (IV) are collectively referred as a "calcining step" in some cases.

In steps (III) and (IV), the dry powder obtained in the drying step is calcined. The condition such as the calcining temperature, the time, and the atmosphere may be properly determined from the viewpoint of removing organic components contained in the dry powder or crystal growth of the complex oxide, and is not particularly limited. In the production method according to the present embodiment, the condition such as the temperature is changed, and calcination at multi stages such as pre-stage calcination and main calcination is performed as described later.

Herein, the term "protruding object" indicates an object that is exuded and/or adhered onto the surface of the calcined body obtained by the below-described main calcination, and refers to an object that protrudes from the surface of the calcined body or adheres thereto. Here, many protruding objects are protruding crystals of oxides and other impurities. Particularly, in the case of a calcined body containing a plurality of metals, oxides having a composition different from that of the crystals that form most of the calcined body may be formed in such a shape that the oxides are exuded from the main part of the calcined body. In this case, the protruding object is often formed in a shape of a plurality of protruding objects (e.g., a height of 0.1 μm to 20 μm) on the surface of a spherical calcined body (e.g., a diameter of 30 to 150 μm). Removal of the protruding objects will be described in detail below.

(Method of Calcining Dry Powder)

As a calcining apparatus for calcining the dry powder, for example, a rotary furnace (rotary kiln) can be used. The shape of the calcining apparatus is not particularly limited. A tubular shape (calcining tube) is preferable and a cylindrical shape is particularly preferable from the viewpoint of enabling continuous calcination. As a heating method, external heating is preferable from the viewpoint of easiness to adjust the calcining temperature in a preferred temperature raising pattern. An electric furnace can be suitably used. The size and material of the calcining tube can be properly selected depending on the calcining condition and the amount of production. The inner diameter of the calcining tube is preferably 70 to 2000 mm, and more preferably 100 to 1200 mm from the viewpoint of providing even calcining temperature distribution within the catalyst layer, and adjusting the calcining time and the amount of production at a proper value. The length of the calcining tube is preferably 200 to 10000 mm, and more preferably 800 to 8000 mm from the viewpoint of reducing the stagnation time of the dry powder and the catalyst precursor particles within the calcining tube, namely, distribution of the calcining time as much as possible, preventing distortion of the calcining tube, and adjusting the calcining time and the amount of production at a proper value. When an impact is imparted to the calcining tube, the thickness of the calcining tube is preferably 2 mm or more, and more preferably 4 mm or more from the viewpoint that the calcining tube has an enough thickness not to be broken by the impact. The thickness of the calcining tube is preferably 100 mm or less, and more preferably 50 mm or less from the viewpoint that the impact is sufficiently transmitted into the calcining tube. The material of the calcining device is not particularly limited as long as the calcining device preferably has heat resistance and strength to the extent not to be broken by the impact. SUS can be appropriately used as the material of the calcining tube.

Herein, the "catalyst precursor" refers to a compound produced at an intermediate stage of the calcining step.

In the main calcination step, the crystallite size of the catalyst can be controlled. To control the crystallite size to a proper range, it is preferred to carry out the main calcination at 600 to 750° C. for 0.1 to 20 hours, and more preferably at 650 to 720° C. for 0.5 to 5 hours. Crystallite size is greatly influenced by the main calcination temperature and/or time. The higher the calcination temperature is and/or the longer the calcination time is, the larger the crystallite size is. The silica-supported catalyst crystals have a columnar shape, in which the ratio of side faces based on total crystal faces increases when the crystals grow in the (001) direction. It is known that an ammoxidation reaction proceeds at the upper and lower faces, and that the side faces are degradation faces. The crystallite size measured in the present embodiment is the length in the (001) direction. If the crystallite size is more than 250 nm, it is thought that the ratio of degradation faces based on total crystal faces increases. Consequently, combustion of the raw material ammonia and degradation of the target product occur more easily. Conversely, the lower the calcination temperature and/or the shorter the calcination time, the smaller the crystallite size is. If the crystallite size is less than 40 nm, the formation of active sites is insufficient, so that combustion of the raw material ammonia and degradation of the target product occur more easily. Therefore, the crystallite size of the catalyst is 40 to 250 nm, and preferably 40 to 180 nm. Since a catalyst having a crystallite size in the proper range has a high degree of completion of the crystals, and a small low ratio of degradation faces based on total crystal faces, combustion of the raw material ammonia can be suppressed, and the target product can be produced in a high yield.

The crystallite size of the catalyst can be determined based on X-ray diffraction. Since the peaks of impurities that are not involved in the reaction overlap the (001) peak that is involved in the reaction, pre-processing is performed. The pre-processing is carried out by charging 5 to 20 g of catalyst, 200 mL of water, and 2 mL of nitric acid into a pressure-resistant vessel, and leaving for 24 hours or more at 150 to 200° C. in a sealed state to dissolve the impurities. After 24 hours or more has elapsed, the temperature of the pressure-resistant vessel is reduced to room temperature, and filtering is carried out with filter paper. The solid product obtained by the filtering is dried for 24 hours or more in a hot bath set to 30 to 100° C. The dried powder is subjected to X-ray diffraction measurement, whereby the (001) peak for only the crystals involved in the reaction can be obtained.

The method for measuring the crystallite size can be carried out using the Scherrer equation from the half width of the peak obtained based on X-ray diffraction after the pre-processing has finished. The specific X-ray measurement conditions may be as follows. Apparatus: RIGAKU RINT 2500 HF/PC, light source: Cu Kα rays, output: 40 kV at −20 mA, measurement range (2θ): 5 to 50°, scanning speed: 1 deg/min, and number of repetitions: 4. To obtain the correct half width, before measuring the sample, it is preferred to correct the spread in the half width particular to the apparatus using a standard reference substance (LaB6).

The crystallite size was calculated using the Scherrer following equation (ii) from the half width of the (001) peak (interplanar spacing d=4.02) obtained based on X-ray diffraction. The (001) peak (interplanar spacing d=4.02) is a peak derived from the crystal involved in the reaction.

$$L=0.9\lambda/\beta \cos\theta \qquad (ii)$$

Here, L represents crystallite size (Å), λ represents wavelength (Å), β represents the diffraction line width (rad), and θ represents the diffraction angle (rad).

A calcining atmosphere may be under an air atmosphere or under an air flow. However, at least a portion of the calcination is preferably carried out while an inert gas which does not substantially contain oxygen, such as nitrogen, flows from the viewpoint of adjusting to preferable oxidation/reduction state. In the case where calcination is performed in batch, the amount of an inert gas to be fed is not less than 50 N liters/Hr per 1 kg of the dry powder from the viewpoint of adjustment to a preferred state of oxidation and reduction. The supplied amount of the inert gas is preferably 50 to 5000 N liters/Hr, and more preferably 50 to 3000 N liters/Hr. (N liter means a liter measured under normal temperature and pressure conditions, that is, at 0° C. and 1 atm.)

In the case where calcination is continuously performed, the amount of an inert gas to be fed is not less than 50 N liters per 1 kg of the dry powder from the viewpoint of adjustment to a preferred state of oxidation and reduction. The amount is preferably 50 to 5000 N liters, and more preferably 50 to 3000 N liters. On this occasion, the flows of inert gas and dry powder may be in the form of a counter flow or a parallel flow. However, counter flow contact is preferable in consideration of gas components generated from the dry powder and a trace amount of air entering together with the dry powder.

Other than moisture, the dry powder usually contains ammonium radicals, organic acids, inorganic acids, and the like. In the case where calcination is performed while the inert gas substantially containing no oxygen is flowed, the catalyst forming elements are reduced when ammonium radicals, organic acids, inorganic acids, and the like are evaporated or decomposed. In the case where the catalyst forming element in the dry powder has an almost highest oxidation number, in order to obtain the reduction rate of the catalyst in a desired range, only reduction is performed in the calcining step, and this is industrially simple.

On the other hand, as described below, an oxidizing component or a reducing component may be added into the calcining atmosphere so that the reduction rate of the pre-stage calcined body is in a desired range. In the production method according to the present embodiment, the calcining is preferably carried out so that the reduction rate of the obtained pre-stage calcined body is 8 to 12% and the specific surface area of the catalyst is 5 to 25 $m^2/g$. By making the specific surface area of the catalyst be 5 to 25 $m^2/g$, the advantageous effects of even more sufficient activity, suppression of raw material ammonia combustion, and a much higher yield tend to be obtained. If the specific surface area of the catalyst is more than 25 $m^2/g$, the number of degradation sites on the silica surface increases, so that combustion of the raw material ammonia and degradation of the target product tend to occur. If the specific surface area of the catalyst is less than 5 $m^2/g$, a sufficient number of degradation sites is not produced, so that the yield tends to deteriorate. Moreover, regarding the effect of adding the molybdenum compound in order to maintain the yield in the ammoxidation reaction, this effect is exhibited more sufficiently, with no sudden deterioration being shown. Accordingly, this tends to enable the amount and frequency of the molybdenum compound addition to be reduced. Although the reason for this is not clear, it is believed to be that because at a specific surface area of the catalyst of less than 5 $m^2/g$ the active face of the active species involved in the reaction is small, it is difficult for the effect of adding the molybdenum compound to be exhibited. Further, if the specific surface area of the catalyst is more than 25 $m^2/g$, although the active face of the active species involved in the reaction increases, the rate of molybdenum escaping from the active face also increases. Therefore, the specific surface area of the catalyst is 5 to 25 $m^2/g$, and preferably is 8 to 18 $m^2/g$. The specific surface area is determined based on a BET single point method using a Gemini 2360 manufactured by Micrometrics Instrument Corporation.

The reduction rate of the pre-stage calcined product is represented by the following equation (2)

$$\text{Reduction rate}(\%)=((n_0-n)/n_0)\times 100 \qquad (2)$$

(wherein n is the number of oxygen atoms that satisfy a valence of constituent elements other than oxygen in the pre-stage calcined product, and $n_0$ is the number of oxygen atoms needed when the respective constituent elements other than oxygen in the pre-stage calcined product have the highest oxidation number).

Specifically, the dry powder is calcined on the calcining condition as follows: the heating temperature of the dry powder is raised from a temperature lower than 400° C., and continuously or intermittently to a temperature in the range of 600 to 750° C. At this time, the calcining condition is adjusted so that the reduction rate of the pre-stage calcined product calcined when the heating temperature reaches 400° C. is 8 to 12%.

Although the temperature and time at which the catalyst is ultimately calcined (heated) and the silica content affect the specific surface area of the catalyst, the reduction rate when the heating temperature reaches 400° C., the main calcination temperature and/or time, and the rate of decrease in the temperature after the main calcination have an especially large effect. If the reduction rate when the heating temperature reaches 400° C. is low, the specific surface area of the catalyst tends to decrease, while if the reduction rate when the heating temperature reaches 400° C. is high, the specific surface area of the catalyst tends to increase. Further, the main calcination is carried out at a temperature of 600 to 750° C. for 0.1 to 20 hours. The higher the main calcination temperature, or the longer the time, the smaller the specific surface area of the catalyst tends to be. Although the reason is not clear, when performing the calcination over two stages, if the temperature of the main calcination is constant, the higher the maximum temperature of the pre-stage main calcining, the larger the specific surface area becomes, while the lower the maximum temperature of the pre-stage main calcining, the smaller the specific surface area becomes. In addition, it is preferred that the rate of decrease in the temperature after the main calcination is 0.05 to 50° C./min, and 0.05 to 20° C./min is more preferred. The smaller the rate of decrease in the temperature after the main calcination, the smaller the specific surface area tends to be.

The specific surface area and crystallite size of the catalyst can be controlled separately by adjusting the calcining conditions. Since the temperature at which crystal growth proceeds is in the main calcination region, the crystallite size is controlled by the main calcination temperature and/or main calcination time. Since the temperature region in which the sintering of the silica proceeds, which has a large effect on the specific surface area, is wider than the temperature region in which crystal growth proceeds, it is preferred to control the specific surface area by the rate of decrease in the temperature after the main calcination has finished. Further, since the specific surface area has a large effect on the degree of oxidation and reduction, it is preferred to control the reduction rate based on an index.

In the case where calcination is performed by the rotary kiln, the feed rate of the dry powder can be adjusted during the calcination to adjust the specific surface area of the catalyst. If the feed rate is small, the dry powder stagnates within the system for a longer time. For this reason, reduction of the dry powder progresses by a reducing gas such as ammonia, which is produced by heating the dry powder in the calcining tube, the reduction rate is higher, and the specific surface area of the catalyst to be obtained after the main calcination is larger. Conversely, the feed rate is large, the reduction rate is lower, and the specific surface area of the catalyst is smaller. Alternatively, the specific surface area can be adjusted by the amount of nitrogen during the pre-stage calcination. If the amount of nitrogen is increased, the component gas that reduces the pre-stage calcined powder during calcination is quickly discharged to the outside of the system. Accordingly, it is thought that the pre-stage calcined product is difficult to reduce, resulting a small specific surface area. Conversely, if the amount of nitrogen is reduced, the reduction rate is higher, and the specific surface area of the catalyst is larger.

In order to obtain the specific surface area of the catalyst of 5 to 25 m²/g, preferably, the reduction rate when the heating temperature reaches 400° C. is in the range of 8 to 12%, and the final calcining temperature is 600° C. to 750° C.

The calcining step comprises the pre-stage calcination and the main calcination. Preferably, the pre-stage calcination is performed at a temperature in the range of 200 to 400° C., and the main calcination is performed at a temperature in the range of 600 to 750° C. The pre-stage calcination and the main calcination may be successively performed; or the pre-stage calcination may be once completed, and the main calcination may be newly performed. Alternatively, the pre-stage calcination and the main calcination each may have several stages.

In the case where the reduction rate of the pre-stage calcined product during the calcination is measured, the sample may be extracted from the calcining apparatus at the temperature. However, the sample may contact the air at a high temperature to be oxidized, and the reduction rate may be changed. Preferably, after the calcining apparatus is cooled to room temperature, the pre-stage calcined product is extracted from the calcining apparatus, and used as a representative sample. Examples of the method for controlling the reduction rate when the heating temperature reaches 400° C. in a desired range specifically include a method of changing the temperature in the pre-stage calcination, a method of adding an oxidizing component such as oxygen to an atmosphere during calcination, or a method of adding a reducing component to an atmosphere during calcination. Moreover, these may be used in combination.

The method of changing the temperature in the pre-stage calcination is to change the calcining temperature in the pre-stage calcination, and a method of changing the reduction rate when the heating temperature reaches 400° C. Usually, the reduction rate is likely to be reduced by reducing the temperature in the pre-stage calcination, and increased by raising the temperature in the pre-stage calcination. For this reason, the temperature in the pre-stage calcination can be changed to control the reduction rate. The reduction rate can also be controlled by increasing or reducing the amount of nitrogen to be fed, increasing or reducing the amount of the dry powder to be fed, and increasing or reducing the number of rotation of the rotary kiln in the calcination using the rotary kiln. It is thought that if the amount of the nitrogen to be fed is increased, in the oxidized components evaporated from the dry powder by heating the furnace, the proportion of the oxidized components discharged to the outside of the system without being oxidized by a metal oxide that exists within the calcining furnace (the metal oxide is reduced) is higher, and therefore the calcined product is difficult to reduce. It can also be thought that if the amount of the dry powder to be fed is reduced, reduction progresses in the rotary kiln because the catalyst stagnates for a longer time in the rotary kiln. It is also thought that in the case of the rotary kiln, if the number of rotation thereof is reduced, the moving speed of the catalyst within the rotary kiln is reduced; for this reason, reduction progresses because the catalyst contacts a larger amount of the oxidized components for a longer time.

The measurement of the reduction rate of the pre-stage calcined product before the calcination is performed as follows.

Approximately 200 mg of the pre-stage calcined product is weighed and placed in a beaker. Further, an excessive amount of a $KMnO_4$ aqueous solution having a known concentration is added. Further, 150 mL of pure water at 70° C. and 2 mL of 1:1 sulfuric acid (namely, a sulfuric acid aqueous solution obtained by mixing concentrated sulphuric acid with water in a volume ratio of 1/1) are added, and the beaker is covered with a watch glass. The mixed-solution is stirred in a hot water bath at 70° C.±2° C. for 1 Hr to oxidize the sample. At this time, $KMnO_4$ excessively exists, and non-reacted $KMnO_4$ exists in the solution. For this, it is checked that the color of the solution is violet. After oxidation is completed, the solution is filtered by a filter paper to recover the total amount of the filtrate. An excessive amount of a sodium oxalate aqueous solution having a known concentration is added to $KMnO_4$ that exists in the filtrate, and heated and stirred so that the temperature of the solution is 70° C. It is checked that the solution becomes colorless and transparent, and 2 mL of 1:1 sulfuric acid is added. Stirring is continued while the temperature of the solution is kept at 70° C.±2° C., and titrated by a $KMnO_4$ aqueous solution having a known concentration. When the color of the solution keeps light pink for approximately 30 seconds by $KMnO_4$, it is the end point.

From the total amount of $KMnO_4$ and the total amount of $Na_2C_2O_4$, the amount of $KMnO_4$ consumed in oxidation of the sample is determined. From the value, $(n_0-n)$ is calculated, and the reduction rate is determined based on the obtained value.

The measurement of the reduction rate of the calcined product after the main calcination is completed can be performed as follows.

Approximately 200 mg of the calcined product ground by an agate mortar is weighed and placed in a beaker. 150 mL of pure water at 95° C. and 4 mL of 1:1 sulfuric acid (namely, a sulfuric acid aqueous solution obtained by mixing concentrated sulphuric acid with water in a volume ratio of 1/1) are added. Stirring is continued while the temperature of the solution is kept at 95° C.±2° C., and titrated by a $KMnO_4$ aqueous solution having a known concentration. At this time, although the color of the solution temporarily becomes violet by titration of $KMnO_4$, $KMnO_4$ is slowly titrated little by little so as not to continue the color of violet for not less than 30 seconds. The amount of the solution is reduced by evaporation of water. For this reason, pure water at 95° C. is added so that the amount of the solution is kept constant. When the color of the solution keeps light pink for approximately 30 seconds by $KMnO_4$, it is the end point.

Thus, the amount of $KMnO_4$ consumed in oxidation of the sample is determined. From the value, $(n_0-n)$ is calculated, and the reduction rate is determined based on the obtained value.

Other than the measurement method, the measurement of the reduction rate can be performed in the pre-stage calcined product before the main calcination is completed and the calcined product after the main calcination is completed, as follows.

On the condition in which the constituent elements in the sample are not volatilized nor lost, the sample is heated to a temperature higher than the calcining temperature at which the pre-stage calcined product or the calcined product is calcined, and complete oxidation by oxygen is performed. The increased mass (the amount of oxygen bonded) is determined. From this, the value of $(n_0-n)$ is determined. Based on this, the reduction rate is determined.

The calcining is performed in an inert gas or a preferred oxidation/reduction atmosphere. Therefore, the calcining apparatus that has a proper sealing structure, and can sufficiently block contact with an open air is preferably used.

The pre-stage calcination is performed preferably under a flow of an inert gas at a temperature in the pre-stage calcination in the range of preferably 200° C. to 400° C., and more preferably of 300° C. to 400° C. from the viewpoint of easiness to adjust the catalyst to obtained in a preferred state of oxidation and reduction and improvement in the ability of the catalyst. Preferably, the temperature in the pre-stage calcination is kept at a constant temperature in the range of 200° C. to 400° C. The temperature may be changed in the range of 200° C. to 400° C., or mildly raised or lowered. The retention time of the heating temperature is preferably not less than 30 minutes, and more preferably 3 to 12 hours from the viewpoint of easiness to adjust the catalyst to be obtained in a preferred state of oxidation and reduction and improvement in the ability of the catalyst. As the pattern of the temperature that reaches the temperature in the pre-stage calcination, the temperature may be linearly raised, or may be raised as if an arc projected upward or downward is drawn. Moreover, the temperature may be lowered at some time during raising the temperature, or the temperature may be repeatedly raised and lowered. Further, an endothermic reaction occurs during raising the temperature by the component contained in the dry powder and/or the catalyst precursor, and the temperature may be temporarily lowered.

The average temperature raising rate at the time of raising the temperature to the temperature in the pre-stage calcination is not particularly limited. The average temperature raising rate is usually approximately 0.1 to 15° C./min, preferably 0.5 to 5° C./rain, and more preferably 1 to 2° C./min from the viewpoint of easiness to adjust the catalyst to be obtained in a preferred state of oxidation and reduction and improvement in the ability of the catalyst.

The main calcination can be performed preferably under a flow of an inert gas at a temperature of preferably of 600 to 750° C., and more preferably of 650 to 720° C. from the viewpoint of easiness to adjust the catalyst to be obtained in a preferred state of oxidation and reduction, sufficient formation of a crystal structure active to the reaction, and improvement in the ability of the catalyst. The main-calcining temperature is preferably kept at a constant temperature in the range of 650 to 720° C. The temperature may be changed or mildly raised or lowered in the range of 650 to 720° C. Moreover, the temperature may be lowered at some time during raising the temperature, or the temperature may be repeatedly raised and lowered. An endothermic reaction occurs during raising the temperature by the component contained in the dry powder, and the temperature may be lowered in the pattern according to the development of the situation.

The specific surface area of the catalyst can be adjusted by the calcining temperature. A catalyst having a specific surface area can be obtained by increasing or reducing the temperature of the pre-stage calcination or a specific surface area. Preferably, the calcining temperature in the main calcination easily influenced by the specific surface area is adjusted to obtain the target catalyst having a specific surface area.

The time for the main calcination is preferably 0.1 to 20 hours, and more preferably 0.5 to 5 hours. In the case where the calcining tube is partitioned by a weir plate, the pre-stage calcined product and/or the calcined product continuously passes through at least two zones, preferably 2 to 20 zones, and more preferably 4 to 15 zones from the viewpoint of ensuring the stagnation time of the dry powder or the like in the calcining tube. The temperature can be controlled using one or more controller. In order to obtain the desired calcining pattern, a heater and a controller are preferably provided in each of the zones partitioned by these weirs to control the temperature. For example, in the case where seven weir plates are provided so that the length of the portion of the calcining tube placed within the heating furnace is equally divided into eight zones, and the calcining tube having the eight divided zones is used, preferably, the set temperature in each of the eight zones is controlled by the heater and the controller provided in each of the eight zones so that the temperature of the partially-calcined powder and/or the calcined powder is controlled at the desired calcining temperature pattern. For example, in the case where seven weir plates are provided so that the length of the portion of the calcining tube placed within the heating furnace is equally divided into eight zones, and the calcining apparatus having the eight divided zones is used, adjustment can be performed as follows in order to obtain the desired calcining pattern. In the pre-stage calcination, preferably, the temperature of the thermocouple inserted into the central portion of the pre-stage calcined product that stagnates within each of the zones in the calcining apparatus is adjusted so that the zone 1: 120 to 280° C., the zone 2: 180 to 330° C., the zone 3: 250 to 350° C., the zone 4: 270 to 380° C., the zone 5: 300 to 380° C., the zone 6: 300 to 390° C., the zone 7: 320 to 390° C., and the zone 8: 260 to 380° C. from the feeding side of the pre-stage calcined product. Similarly, in the main calcination, adjustment is preferably performed so that the zone 1: 360 to 560° C., the zone 2: 450 to 650° C., the zone 3: 600 to 700° C., the zone 4: 650 to 750° C., the zone 5: 600 to 700° C., the zone 6: 500 to 690° C., the zone 7: 480 to 630° C., and the zone 8: 400 to 580° C.

The specific surface area of the pre-stage calcined product can be adjusted to some extent according to the condition of the pre-stage calcination, but not as much as in the case of the calcined product. Although the reason is not clear, the reduction rate is proportional to the specific surface area, and by performing the same management as above, the range of the specific surface area is easily optimized. However, adjustment of the specific surface area of the catalyst largely depends on the calcining method in the main calcination.

The calcining temperature of 650° C. greatly exceeds the melting points of oxides of the constituent metals. For this reason, a large amount of oxides adhere to the wall surface of the calcining tube. Therefore, the stagnation time of the pre-stage calcined product is preferably increased by increasing the number of strokes to the main-calcining tube using a hammer or the like, or increasing the number of rotation. The rate of these numbers to be increased can be arbitrarily set from a mass balance between the amount of the pre-stage calcined powder to be fed to the main-calcining tube and the amount of the catalyst to be discharged from the main-calcining tube. An oxidizing component (for example, oxygen) or a reducing component (for example, ammonia) may be added to the calcining atmosphere under a flow of the inert gas, if desired.

As the pattern of raising the temperature to the main-calcining temperature, the temperature may be linearly raised, or may be raised as if an arc projected upward or downward is drawn. Moreover, the temperature may be lowered at some time during raising the temperature, or the temperature may be repeatedly raised and lowered. An endothermic reaction occurs during raising the temperature by the component contained in the pre-stage calcined product, and the temperature may be lowered in the pattern according to the development of the situation.

The average temperature raising rate during raising the temperature at which the temperature reaches the main-calcining temperature is not particularly limited, and preferably 0.5 to 8° C./min. The average temperature falling rate after the main calcination is completed is preferably 0.05 to 50° C./min, and more preferably 0.05 to 20° C./min from the viewpoint of control of the specific surface area, sufficient formation of a crystal structure active to the reaction and improvement in the ability of the catalyst. Preferably, the temperature is kept once at a temperature lower than the main-calcining temperature and annealing is performed from the viewpoint of sufficient formation of a crystal structure active to the reaction and improvement in the ability of the catalyst. The temperature to be kept is a temperature 5° C., preferably 10° C., and more preferably 50° C. lower than the main-calcining temperature. From the same viewpoint as above, the time to keep is preferably not less than 0.5 hours, more preferably not less than 1 hour, still more preferably not less than 3 hours, and particularly preferably not less than 10 hours.

When the main calcination is carried out anew once the pre-stage calcination has been completed, a low temperature treatment can be performed at the main calcination. A time required for the low temperature treatment, that is, a time required for reducing the temperature of the pre-stage calcined product and/or the calcined product and raising the temperature to the calcining temperature can appropriately be adjusted by the size, the thickness, and the material of the calcining device, a catalyst production amount, a series of periods for continuously calcining the pre-stage calcined product and/or the calcined product, and a fixing rate and a fixing amount, or the like. The time needed for the low temperature treatment is preferably 30 days or less, more preferably 15 days or less, still more preferably 3 days or less, and particularly preferably 2 days or less during a series of continuous calcination of the calcined product from the viewpoint of sufficiently removing the pre-stage calcined powder and/or the calcined product adhering to the wall surface of the calcining tube, stably keeping the temperature of the oxide layer, and improving the ability of the catalyst to be obtained. The temperature of the oxide layer refers to a temperature measured by a thermocouple inserted into the pre-stage calcined powder and/or main-calcined powder deposited within the calcining apparatus. Further, for example, when the pre-stage calcined powder is supplied at a rate of 35 kg/hr while a rotary kiln having a calcining tube having an inner diameter of 500 mm, a length of 4500 mm, and a thickness of 20 mm and made of SUS is rotated at 6 rpm, and the main calcining temperature is 645° C., the step of lowering a temperature to 400° C. and raising the temperature to 645° C. can be performed in about 1 day. When calcination is continuously performed for 1 year, the calcination can be performed by carrying out such low temperature treatment once a month while a temperature of an oxide layer is stably maintained.

If impact is given to the calcining apparatus in the calcining step, an effect of cracking adhering lumps is likely to be enhanced. In the case where the low temperature treatment is performed, the impact given to the calcining apparatus is preferable because cracked lumps are likely to be easily removed from the calcining apparatus.

Protruding objects are produced on the surface of the particles of the calcined body which has been subjected to the main calcination step. Since the calcined body according to the present embodiment has a more appropriate composition than that of a conventional calcined body, the amount of protruding objects is less, and the effect of the protruding objects is smaller than for a conventional catalyst. However, if protruding objects are present in the reactor during a vapor-phase ammoxidation reaction, because side reactions tend to occur and/or fluidity deteriorates due to the protruding bodies shearing off, it is preferred to remove the protruding objects before the reaction.

It is preferred to lower the amount of protruding objects to 2% by mass or less based on the total mass of the calcined body by removing the protruding objects. Several methods can be thought of as the method for removing the protruding objects. Among these, preferred is a method in which the protruding objects are removed by bringing catalyst particles into contact with each other under a gas flow, for example. Examples of the method include a method in which a gas is flowed through a hopper or the like in which the calcined body is stored, and a method in which the calcined body is placed in a fluidized bed reactor and a gas is made to flow therethrough. Although the method using a fluidized bed reactor is preferred as it does not require any special apparatus for removing the protruding objects, because such an apparatus was not originally designed to bring catalyst particles into contact with each other, unless special measures are taken, such as charging a small amount of catalyst and reacting for some time, depending on the conditions, such as the amount of catalyst to be fed and the time to flow catalyst and the amount of gas, the protruding objects may not be sufficiently removed. According to examination by the present inventors, the air stream at a sufficient flow rate can be contacted with the calcined product having the protruding object to efficiently remove the protruding object. If a proper flow rate is provided in an apparatus having a structure in which the air stream is contacted with the calcined product, the protruding object can be efficiently removed even in a large scale.

For example, an apparatus can efficiently remove the protruding object in a large scale, the apparatus including a main body that accommodates the calcined product, a recover unit for recovering the calcined product provided in an upper portion of the main body, and a returning unit for returning the calcined product and connected to the recover unit. The returning unit is provided so that a lower end thereof is in contact with the air stream. Part of the calcined product contacting the air stream within the main body is recovered by the recover unit, and returned into the main body by the returning unit.

A gas is flowed through the apparatus filled with the calcined product such as a fluidized bed reactor. Thereby, the calcined products contact each other to remove the protruding object. The protruding object removed from the calcined product is much smaller than the calcined product, and discharged with the flowed gas to the outside of the fluidized bed reactor. Preferably, the calcined product is filled into the apparatus so that the density of the calcined product at this time is 300 to 1300 kg/m$^3$. The cross section area of the body of the apparatus to be used is preferably 0.1 to 100 m$^2$, and more preferably 0.2 to 85 m$^2$.

The gas to be flowed is preferably an inert gas such as nitrogen and the air. The linear velocity of the gas to be flowed through the body of the apparatus filled with the calcined product such as a hopper and a fluidized bed reactor is preferably 0.03 m/s to 5 m/s and more preferably 0.05 to 1 m/s. The time to flow the gas is preferably 1 to 168 hours. Specifically, the apparatus for removing a protruding object according to the present embodiment includes a main body, wherein the calcined product accommodated in the main body is contacted with the air stream, or the particles flowed by the air stream contact with each other to remove the protruding object on the surface of the calcined product from the calcined product. Preferably, the length of the air stream in the direction of the air stream flowing is not less than 10 mm, and the average flow rate of the air stream is not less than 80 m/s and not more than 500 m/s in terms of the linear velocity at 15° C. and 1 atmospheric pressure.

If the removal of the protruding objects is carried out using a gram scale, the following apparatus can be used. Namely, an apparatus that has a vertical tube provided with a plate having one or more holes formed in the bottom and a paper filter on an upper portion. The calcined body is fed into the vertical tube, and air is flowed from a lower portion of the vertical tube. The air flow flows through the respective holes to promote contact among the calcined body particles, whereby the protruding objects are removed.

[Vapor-phase Catalytic Ammoxidation Reaction]

The vapor-phase catalytic ammoxidation reaction according to the present embodiment is a method for producing an unsaturated nitrile corresponding to propane or isobutane by a vapor-phase catalytic ammoxidation reaction of propane or isobutane, wherein the silica-supported catalyst is used.

The feed raw materials for propane, isobutane, and ammonia do not always need to have high purity, and a gas of industrial grade can be used. As a feed oxygen source, air, pure oxygen, or air enriched with pure oxygen can be used. Further, as a diluted gas, helium, neon, argon, carbon dioxide gas, steam, nitrogen, and the like may be fed.

The vapor-phase catalytic ammoxidation reaction of propane or isobutane can be performed on the following condition.

The molar ratio of oxygen to be fed in the reaction to propane or isobutane is 0.1 to 6, and preferably 0.5 to 4. The molar ratio of ammonia to be fed in the reaction to propane or isobutane is 0.3 to 1.5, and preferably 0.7 to 1.2. The reaction temperature is 350 to 500° C., and preferably 380 to 470° C. The reaction pressure is $5 \times 10^4$ to $5 \times 10^5$ Pa, and preferably $1 \times 10^5$ to $3 \times 10^5$ Pa. The contact time is 0.1 to 10 (sec·g/cc), and preferably 0.5 to 5 (sec·g/cc).

In the present embodiment, the contact time is defined by the equation below:

$$\text{Contact time(sec·g/cc)} = (W/F) \times 273/(273+T)$$

Here, W, F, and T are defined as follows:
W=amount of the catalyst to be filled (g)
F=flow rate of the raw material mixed gas (Ncc/sec) in a standard state (0° C., $1.013 \times 10^5$ Pa)
T=reaction temperature (° C.)

As the reaction method for the vapor-phase catalytic ammoxidation reaction, the conventional method such as a fixed bed, a fluidized bed, and a moving bed can be used. Preferred is a fluidized bed reactor in which the reaction heat is easily removed. The vapor-phase catalytic ammoxidation reaction may be a single current system or a recycle system.

EXAMPLES

Hereinafter, the present embodiment will be further described in detail with reference to examples and comparative examples. However, the scope of the present embodiment is not limited to the examples.

In the examples and the comparative examples, a ratio of propane conversion, yield of acrylonitrile, and ammonia combustion respectively follow the following definitions.

Ratio of propane conversion(%)=(Number of moles of reacted propane)/(Number of moles of supplied propane)×100

Yield of Acrylonitrile (AN)(%)=(Number of moles of produced acrylonitrile)/(Number of moles of supplied propane)×100

Ammonia combustion (%)=(Number of moles of produced nitrogen)×2/(Number of moles of supplied ammonia)

The numbers of moles of produced acrylonitrile and nitrogen were measured by gas chromatography.

Example 1

(Preparation of Niobium Raw Material Solution)

A niobium raw material solution was prepared by a method as described below. To 500 kg of water, 76.33 kg of niobic acid containing 80.2% by mass of niobium in terms of $Nb_2O_5$ and 290.2 kg of oxalic acid dihydrate [$H_2C_2O_4 \cdot 2H_2O$] were added. A molar ratio of oxalic acid/niobium as feedstocks was 5.0 and a concentration of feedstock niobium was 0.532 (mol-Nb/kg-solution).

The resultant solution was heated for one hour at 95° C. with stirring, thereby obtaining an aqueous solution in which niobium compound was dissolved. This aqueous solution was left standstill, cooled with ice, subjected to a suction filtration for removing a solid content, thereby obtaining a uniform aqueous solution of niobium compound. After repeating the same procedure several times, the resulting aqueous solutions of niobium compound were combined to produce niobium raw material solution. The molar ratio of the oxalic acid/ niobium of this niobium raw material solution was 2.40 by the analysis described below.

10 g of this niobium raw material solution was precisely weighed and put in a crucible, dried for a night at 95° C., and subjected to a heat treatment for one hour at 600° C., thereby obtaining 0.8323 g of $Nb_2O_5$. From this result, the niobium concentration was 0.626 (mol-Nb/kg-solution).

3 g of this niobium raw material solution was precisely weighed and put in a glass beaker having a capacity of 300 ml, added with 200 ml of hot water having a temperature of about 80° C. and, then, added with 10 ml of a 1:1 sulfuric acid. The resultant aqueous solution was titrated by using a ¼ N $KMnO_4$ solution with stirring while being kept at a temperature of 70° C. on a hot stirrer. A point at which a faint light pink color by $KMnO_4$ lasted for about 30 seconds or more was defined as an end-point. A concentration of oxalic acid was determined on the basis of the resultant titer in accordance with the following formula and, as a result, it was 1.50 (mol-oxalic acid/kg).

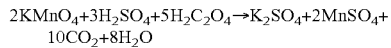

$2KMnO_4+3H_2SO_4+5H_2C_2O_4 \rightarrow K_2SO_4+2MnSO_4+10CO_2+8H_2O$

The obtained niobium raw material solution was used as a niobium raw material solution in production of an oxide catalyst to be described below.
(Formulation of Raw Material-prepared Solution in a Formulation Tank)

19.9 kg of ammonium heptamolybdate $[(NH_4)_6Mo_7O_{24}.4H_2O]$, 2.75 kg of ammonium metavanadate $[NH_4VO_3]$, 3.28 kg of diantimony trioxide $[Sb_2O_3]$, and further an aqueous solution of cerium nitrate in which 495 g of cerium nitrate $[Ce(NO_3)_3.6H_2O]$ was dissolved in 2 kg of water were added to 100 kg of water, and heated under stirring for one hour at 95° C., thereby obtaining a raw material-prepared solution (I).

2.28 kg of a hydrogen peroxide solution containing 30% by mass of $H_2O_2$ was added to 15.9 kg of the niobium raw-material solution. The mixture was stirred and mixed at a solution temperature being kept at about 20° C., thereby obtaining a raw material-prepared solution (II).

The obtained raw material-prepared solution (I) was cooled to 70° C., and 34.2 kg of silica sol containing 30.2% by mass of $SiO_2$ and having an average primary particle size of 50 nm and 3.60 kg of silica sol containing 30.0% by mass of $SiO_2$ and having an average primary particle size of 18 nm were added. Then, 3.80 kg of a hydrogen peroxide solution containing 30% by mass of $H_2O_2$ was added, and stirred and mixed for 30 minutes at 55° C. Thereafter, the raw material-prepared solution (II) and 516 g of an aqueous solution of ammonium metatungstate (50% purity) were added. Further, 8.60 kg of a silica powder was dispersed in 77.4 kg of water, and the resultant mixture was aged as is for 1 hour at 50° C., thereby obtaining a raw material-prepared solution (III).
(Spray Drying of Raw Material-prepared Solution Obtained in Formulation Tank)

Air heated to 210° C. and 50° C. hot water adjusted to a feed rate of 80 kg/Hr were fed to a centrifugal spray dryer until the formulation of the raw material-prepared solution (III) was complete; and the dryer inlet temperature was preset to 210° C. and the outlet temperature to 120° C.

When the feed amount of the raw material-prepared solution fed to the spray dryer was adjusted so that the spray dryer outlet temperature did not fluctuate, the feed amount was 100 kg/Hr. During this period, the outlet temperature was 120±5° C., and did not greatly fluctuate.
(Measurement of UV-visible Reflectance Spectrum)

The obtained dried product was sampled each day. 0.5 g from the obtained 10 samples was tested using a JASCO UV/VIS Spectrometer V-650 manufactured by JASCO Corporation over a range of 200 to 800 nm based on a diffuse reflection method. Spectralon manufactured by Labsphere was used as a baseline reference material. The maximum absorbance value was 1.02. The absorbance at 600 nm was 0.31 to 0.36. Since this was an absorbance for which high performance could be expected based on the description in Japanese Patent Laid-Open No. 2009-148749, all of the spray-dried product was used in the classification operation without sorting.
(Classification Operation)

The obtained dried product was classified using a sieve having a sieve opening of 25 μm to obtain a classified product. The content of particles 25 μm or smaller in the obtained classified product was 0.8% by mass, and the average particle size was 55 μm.
(Calcination of Classified Product)

The obtained classified product was flowed at a rate of 20 kg/hr through a cylindrical calcining tube made of SUS, having an inner diameter of 500 mm, a length of 3,500 mm, and a thickness of 20 mm that was provided with seven weir plates having a height of 150 mm so that the length of the heating furnace section was divided into eight equal sections. Under a nitrogen gas flow of 600 NL/min, the temperature of the heating furnace was adjusted so as to have a temperature profile in which the temperature was increased to 370° C. over about four hours and kept at 370° C. for three hours while the calcining tube was being rotated at 4 rpm, to subject the classified product to pre-stage calcination, thereby obtaining a pre-stage calcined product. Then, the pre-stage calcined product was flowed at a rate of 15 kg/hr through another calcining tube made of SUS having an inner diameter of 500 mm, a length of 3,500 mm, and a thickness of 20 mm that was provided with seven weir plates having a height of 150 mm so that the length of the heating section was divided into eight equal sections, while the tube was being rotated at 4 rpm. At this time, while a portion of the pre-stage calcined product on the powder inlet side of the calcining tube (a portion not covered by the heating furnace) was being hammered once every five seconds from a height of 250 mm above the calcining tube in the direction perpendicular to the rotation axis by a hammering device equipped with a hammer having a mass of 14 kg with a hammering tip end made of SUS, and under a nitrogen gas flow of 500 NL/min, the temperature of the heating furnace was adjusted so as to have a temperature profile in which the temperature was increased to 690° C. at 2° C./min, calcination was carried out at 690° C. for two hours, and the temperature was reduced at 1° C./min, to carry out a main calcination, thereby obtaining an oxide catalyst.
(Composition of Oxide Catalyst)

Analysis of the oxide catalyst showed that it had a composition of $MoV_{0.21}Nb_{0.09}Sb_{0.20}W_{0.01}Ce_{0.01}$. Further, the support amount of silica was 47% by mass based on the total amount of the catalyst formed from a metal oxide and silica.
(Measurement of Specific Surface Area)

The specific surface area was measured based on a BET single point method using a Gemini 2360 manufactured by Micrometrics Instrument Corporation.

The specific surface area was 10.8 $m^2/g$.
(Removal of Protruding Objects)

50 g of the oxide catalyst was fed into a vertical tube (inner diameter: 41.6 mm, length: 70 cm) in which a holed disc having three holes of 1/64 inch in diameter was provided on the bottom of the tube, and a paper filter was provided in the upper part thereof. The length of the air flow in the air flow direction at this time was 52 mm, and the average line speed of the air flow was 310 m/s. Based on confirmation of the oxide catalyst obtained 24 hours later with a SEM, no protruding objects were found to be present on the surface of the oxide catalyst.
(Total Pore Volume)

The total pore volume was determined with a mercury porosimeter.

The total pore volume was 0.297 cm$^3$/g.
(Pore Distribution)

The pore distribution was determined with a mercury porosimeter.

The pore volume ratio of pores having a pore size of less than 60 nm was 3.9%, and the pore volume ratio of pores having a pore size exceeding 120 nm was 1.0%.
(Calculation of Average Pore Size)

Average pore size was calculated using formula (I) and assuming that the pores were cylindrical.

$$D=4V/S \qquad (i)$$

Here, D represents the average pore size (m), V represents the total pore volume (m$^3$/g), and S represents the specific surface area (m$^2$/g).

The calculated average pore size was 110 nm.
(Measurement of Crystallite Size)

The method for measuring the crystallite size can be carried out using the Scherrer equation from the half width of a peak obtained based on X-ray diffraction after the pre-processing has finished. The specific X-ray measurement conditions may be as follows. Apparatus: RIGAKU RINT 2500 HF/PC, light source: Cu Kα rays, output: 40 kV at −20 mA, measurement range (2θ): 5 to 50°, scanning speed: 1 deg/min, and number of repetitions: 4. To obtain the correct half width, before measuring the sample, it is preferred to correct the spread in the half width particular to the apparatus using a standard reference substance (LaB6).

The crystallite size was calculated using the Scherrer equation (ii) from the half width of the (001) peak (interplanar spacing d=4.02) obtained based on X-ray diffraction.

$$L=0.9\lambda/\beta \cos\theta \qquad (ii)$$

Here, L represents crystallite size (Å), λ represents wavelength (Å), β represents the diffraction line width (rad), and θ represents the diffraction angle (rad).

The calculated crystallite size was 106 nm.
(Ammoxidation Reaction of Propane)

Propane was subjected to a vapor-phase ammoxidation reaction by the following method using the oxide catalyst obtained above. 35 g of the oxide catalyst was packed in a Vycor glass fluidized bed-type reaction tube having an inner diameter of 25 mm; and a mixed gas of propane:ammonia:oxygen:helium=1:1:3:18 in molar ratio was supplied for a contact time of 2.8 (sec·g/cc) at a reaction temperature of 440° C. under a reaction pressure of normal pressure. The ratio of propane conversion after the reaction was 89.8%, the yield of acrylonitrile was 54.8%, and the ammonia combustion rate was 18.8%.

Example 2

(Preparation of Niobium Raw Material Solution)

A niobium raw material solution was prepared in the same manner as in Example 1.

(Formulation of Raw Material-prepared Solution in a Formulation Tank)

19.9 kg of ammonium heptamolybdate [(NH$_4$)$_6$Mo$_7$O$_{24}$·4H$_2$O], 2.75 kg of ammonium metavanadate [NH$_4$VO$_3$], 3.28 kg of diantimony trioxide [Sb$_2$O$_3$], and further an aqueous solution of cerium nitrate in which 495 g of cerium nitrate [Ce(NO$_3$)$_3$·6H$_2$O] was dissolved in 2 kg of water were added to 100 kg of water, and heated under stirring for one hour at 95° C., thereby obtaining a raw material-prepared solution (I).

2.28 kg of a hydrogen peroxide solution containing 30% by mass of H$_2$O$_2$ was added to 15.95 kg of the niobium raw-material solution. The mixture was stirred and mixed at a solution temperature being kept at about 20° C., thereby obtaining a raw material-prepared solution (II).

The obtained raw material-prepared solution (I) was cooled to 70° C., and 31.0 kg of silica sol containing 30.2% by mass of SiO$_2$ and having an average primary particle size of 23 nm and 6.80 kg of silica sol containing 30.0% by mass of SiO$_2$ and having an average primary particle size of 13 nm were added. Then, 3.80 kg of a hydrogen peroxide solution containing 30% by mass of H$_2$O$_2$ was added, and stirred and mixed for 30 minutes at 55° C. Thereafter, the raw material-prepared solution (II) and 516 g of an aqueous solution of ammonium metatungstate (50% purity) were added. Further, 8.60 kg of a silica powder was dispersed in 77.4 kg of water, and the resultant mixture was aged as is for 1 hour at 50° C., thereby obtaining a raw material-prepared solution (III).
(Spray Drying of Raw Material-prepared Solution Obtained in Formulation Tank)

Air heated to 210° C. and 50° C. hot water adjusted to a feed rate of 80 kg/Hr were fed to a centrifugal spray dryer until the formulation of the raw material-prepared solution (III) was complete; and the dryer inlet temperature was preset to 210° C. and the outlet temperature to 120° C.

When the feed amount of the raw material-prepared solution fed to the spray dryer was adjusted so that the spray dryer feed temperature did not fluctuate, the feed amount was 100 kg/Hr. During this period, the outlet temperature was 120±5° C., and did not greatly fluctuate.
(Measurement of UV-visible Reflectance Spectrum)

The obtained dried product was sampled each day. 0.5 g from the obtained 10 samples was tested using a JASCO UV/VIS Spectrometer V-650 manufactured by JASCO Corporation over a range of 200 to 800 nm based on a diffuse reflection method. Spectralon manufactured by Labsphere was used as a baseline reference material. The maximum absorbance value was 1.02. The absorbance at 600 nm was 0.31 to 0.36. Since this was an absorbance for which high performance could be expected based on the description in Japanese Patent Laid-Open No. 2009-148749, all of the spray-dried product was used in the classification operation without sorting.
(Classification Operation)

The obtained dried product was classified using a sieve having a sieve opening of 25 μm to obtain a classified product. The content of particles 25 μm or smaller in the obtained classified product was 0.8% by mass, and the average particle size was 55 μm.
(Calcination of Classified Product)

The obtained classified product was flowed at a rate of 20 kg/hr through a cylindrical calcining tube made of SUS, having an inner diameter of 500 mm, a length of 3,500 mm, and a thickness of 20 mm that was provided with seven weir plates having a height of 150 mm so that the length of the heating furnace section was divided into eight equal sections. Under a nitrogen gas flow of 600 NL/min, the temperature of the heating furnace was adjusted so as to have a temperature profile in which the temperature was increased to 370° C. over about four hours and kept at 370° C. for three hours while the calcining tube was being rotated at 4 rpm, to subject the classified product to pre-stage calcination, thereby obtaining a pre-stage calcined product. Then, the pre-stage calcined product was flowed at a rate of 15 kg/hr through another calcining tube made of SUS having an inner diameter of 500 mm, a length of 3,500 mm, and a thickness of 20 mm that was provided with seven weir plates having a height of 150 mm so that the length of the heating furnace section was divided into eight equal sections, while the calcining tube was being rotated at 4 rpm. At this time, while a portion of the pre-stage calcined product on the powder inlet side of the calcining tube (a portion not covered by the heating furnace) was being hammered once every five seconds from a height of 250 mm above the calcining tube in the direction perpendicular to the rotation axis by a hammering device equipped with a hammer having a mass of 14 kg with a hammering tip end made of SUS, and under a nitrogen gas flow of 500 NL/min, the temperature of the heating furnace was adjusted so as to have a temperature profile in which the temperature was increased to 685° C. at 2° C./min, calcination was carried out at 685° C. for two hours, and the temperature was reduced at 1° C./min, to carry out a main calcination, thereby obtaining an oxide catalyst.

(Composition of Oxide Catalyst)

Analysis of the oxide catalyst showed that a metal oxide had a composition of $MoV_{0.21}Nb_{0.09}Sb_{0.20}W_{0.01}Ce_{0.01}$. Further, the support amount of silica was 47% by mass based on the total amount of the catalyst formed from a metal oxide and silica.

(Measurement of Specific Surface Area)

Based on a measurement carried out in the same manner as in Example 1, the specific surface area was 12.8 m$^2$/g.

(Removal of Protruding Objects)

Protruding objects were removed in the same manner as in Example 1.

(Total Pore Volume)

Based on a measurement carried out in the same manner as in Example 1, the total pore volume was 0.288 cm$^3$/g.

(Pore Distribution)

Based on a measurement carried out in the same manner as in Example 1, the pore volume ratio of pores having a pore size of less than 60 nm was 6.8%, and the pore volume ratio of pores having a pore size exceeding 120 nm was 0.6%.

(Calculation of Average Pore Size)

Based on a measurement carried out in the same manner as in Example 1, the average pore size was 90 nm.

(Measurement of Crystallite Size)

Based on a measurement carried out in the same manner as in Example 1, the crystallite size was 98 nm.

(Ammoxidation Reaction of Propane)

Propane was subjected to a vapor-phase ammoxidation reaction by the following method using the oxide catalyst obtained above. 35 g of the oxide catalyst was packed in a Vycor glass fluidized bed-type reaction tube having an inner diameter of 25 mm; and a mixed gas of propane:ammonia:oxygen:helium=1:1:3:18 in molar ratio was supplied for a contact time of 2.8 (sec·g/cc) at a reaction temperature of 440° C. under a reaction pressure of normal pressure. The ratio of propane conversion after the reaction was 90.1%, the yield of acrylonitrile was 54.9%, and the ammonia combustion rate was 18.6%.

Example 3

(Preparation of Niobium Raw Material Solution)

A niobium raw material solution was prepared in the same manner as in Example 1.

(Formulation of Raw Material-prepared Solution in a Formulation Tank)

19.9 kg of ammonium heptamolybdate [$(NH_4)_6Mo_7O_{24}\cdot 4H_2O$], 2.75 kg of ammonium metavanadate [$NH_4VO_3$], 3.28 kg of diantimony trioxide [$Sb_2O_3$], and further an aqueous solution of cerium nitrate in which 495 g of cerium nitrate [$Ce(NO_3)_3\cdot 6H_2O$] was dissolved in 2 kg of water were added to 100 kg of water, and heated under stirring for one hour at 95° C., thereby obtaining a raw material-prepared solution (I).

2.28 kg of a hydrogen peroxide solution containing 30% by mass of $H_2O_2$ was added to 15.95 kg of the niobium raw-material solution. The mixture was stirred and mixed at a solution temperature being kept at about 20° C., thereby obtaining a raw material-prepared solution (II).

The obtained raw material-prepared solution (I) was cooled to 70° C., and 25.3 kg of silica sol containing 30.2% by mass of $SiO_2$ and having an average primary particle size of 25 nm and 12.5 kg of silica sol containing 30.0% by mass of $SiO_2$ and having an average primary particle size of 10 nm were added. Then, 3.80 kg of a hydrogen peroxide solution containing 30% by mass of $H_2O_2$ was added, and stirred and mixed for 30 minutes at 55° C. Thereafter, the raw material-prepared solution (II) and 516 g of an aqueous solution of ammonium metatungstate (50% purity) were added. Further, 8.60 kg of a silica powder was dispersed in 77.4 kg of water, and the resultant mixture was aged as is for 1 hour at 50° C., thereby obtaining a raw material-prepared solution (III).

(Spray Drying of Raw Material-prepared Solution Obtained in Formulation Tank)

Air heated to 210° C. and 50° C. hot water adjusted to a feed rate of 80 kg/Hr were fed to a centrifugal spray dryer until the formulation of the raw material-prepared solution (III) was complete; and the dryer inlet temperature was preset to 210° C. and the outlet temperature to 120° C.

When the feed amount of the raw material-prepared solution fed to the spray dryer was adjusted so that the spray dryer feed temperature did not fluctuate, the feed amount was 100 kg/Hr. During this period, the outlet temperature was 120±5° C., and did not greatly fluctuate.

(Measurement of UV-visible Reflectance Spectrum)

The obtained dried product was sampled each day. 0.5 g from the obtained 10 samples was tested using a JASCO UV/VIS Spectrometer V-650 manufactured by JASCO Corporation over a range of 200 to 800 nm based on a diffuse reflection method. Spectralon manufactured by Labsphere was used as a baseline reference material. The maximum absorbance value was 1.02. The absorbance at 600 nm was 0.31 to 0.36. Since this was an absorbance for which high performance could be expected based on the description in Japanese Patent Laid-Open No. 2009-148749, all of the spray-dried product was used in the classification operation without sorting.

(Classification Operation)

The obtained dried product was classified using a sieve having a sieve opening of 25 μm to obtain a classified product. The content of particles 25 μm or smaller in the obtained classified product was 0.8% by mass, and the average particle size was 55 μm.

(Calcination of Classified Product)

Classified products were calcined in the same manner as in Example 2.

(Composition of Oxide Catalyst)

Analysis of the oxide catalyst showed that a metal oxide had a composition of $MoV_{0.21}Nb_{0.09}Sb_{0.20}W_{0.01}Ce_{0.01}$. Further, the support amount of silica was 47% by mass based on the total amount of the catalyst formed from a metal oxide and silica.

(Measurement of Specific Surface Area)

Based on a measurement carried out in the same manner as in Example 1, the specific surface area was 13.6 $m^2/g$.

(Removal of Protruding Objects)

Protruding objects were removed in the same manner as in Example 1.

(Total Pore Volume)

Based on a measurement carried out in the same manner as in Example 1, the total pore volume was 0.221 $cm^3/g$.

(Pore Distribution)

Based on a measurement carried out in the same manner as in Example 1, the pore volume ratio of pores having a pore size of less than 60 nm was 18.7%, and the pore volume ratio of pores having a pore size exceeding 120 nm was 0.2%.

(Calculation of Average Pore Size)

Based on a measurement carried out in the same manner as in Example 1, the average pore size was 65 nm.

(Measurement of Crystallite Size)

Based on a measurement carried out in the same manner as in Example 1, the crystallite size was 102 nm.

(Ammoxidation Reaction of Propane)

Propane was subjected to a vapor-phase ammoxidation reaction by the following method using the oxide catalyst obtained above. 35 g of the oxide catalyst was packed in a Vycor glass fluidized bed-type reaction tube having an inner diameter of 25 mm; and a mixed gas of propane:ammonia:oxygen:helium=1:1:3:18 in molar ratio was supplied for a contact time of 2.8 (sec·g/cc) at a reaction temperature of 440° C. under a reaction pressure of normal pressure. The ratio of propane conversion after the reaction was 88.5%, and the yield of acrylonitrile was 54.7%. A reaction was carried out for 3 months. The yield of acrylonitrile was 54.7% and the ammonia combustion rate was 19.4%.

Example 4

(Preparation of Niobium Raw Material Solution)

A niobium raw material solution was prepared in the same manner as in Example 1.

(Formulation of Raw Material-prepared Solution in a Formulation Tank)

19.9 kg of ammonium heptamolybdate $[(NH_4)_6Mo_7O_{24}\cdot4H_2O]$, 2.75 kg of ammonium metavanadate $[NH_4VO_3]$, 1.96 kg of tellurium trioxide $[TeO_3]$, and further an aqueous solution of cerium nitrate in which 495 g of cerium nitrate $[Ce(NO_3)_3\cdot6H_2O]$ was dissolved in 2 kg of water were added to 100 kg of water, and heated under stirring for one hour at 95° C., thereby obtaining a raw material-prepared solution (I).

2.28 kg of a hydrogen peroxide solution containing 30% by mass of $H_2O_2$ was added to 15.95 kg of the niobium raw-material solution. The mixture was stirred and mixed at a solution temperature being kept at about 20° C., thereby obtaining a raw material-prepared solution (II).

The obtained raw material-prepared solution (I) was cooled to 70° C., and 31.0 kg of silica sol containing 30.2% by mass of $SiO_2$ and having an average primary particle size of 45 nm and 7.70 kg of silica sol containing 30.0% by mass of $SiO_2$ and having an average primary particle size of 15 nm were added. Then, 3.80 kg of a hydrogen peroxide solution containing 30% by mass of $H_2O_2$ was added, and stirred and mixed for 30 minutes at 55° C. Thereafter, the raw material-prepared solution (II) and 516 g of an aqueous solution of ammonium metatungstate (50% purity) were added. Further, 8.60 kg of a silica powder was dispersed in 77.4 kg of water, and the resultant mixture was aged as is for one hour at 50° C., thereby obtaining a raw material-prepared solution (III).

(Spray Drying of Raw Material-prepared Solution Obtained in Formulation Tank)

Air heated to 210° C. and 50° C. hot water adjusted to a feed rate of 80 kg/Hr were fed to a centrifugal spray dryer until the formulation of the raw material-prepared solution (III) was complete; and the dryer inlet temperature was preset to 210° C. and the outlet temperature to 120° C.

When the feed amount of the raw material-prepared solution fed to the spray dryer was adjusted so that the spray dryer feed temperature did not fluctuate, the feed amount was 100 kg/Hr. During this period, the outlet temperature was 120±5° C., and did not greatly fluctuate.

(Measurement of UV-visible Reflectance Spectrum)

The obtained dried product was sampled each day. 0.5 g from the obtained 10 samples was tested using a JASCO UV/VIS Spectrometer V-650 manufactured by JASCO Corporation over a range of 200 to 800 nm based on a diffuse reflection method. Spectralon manufactured by Labsphere was used as a baseline reference material. The maximum absorbance value was 1.02. The absorbance at 600 nm was 0.31 to 0.36. Since this was an absorbance for which high performance could be expected based on the description in Japanese Patent Laid-Open No. 2009-148749, all of the spray-dried product was used in the classification operation without sorting.

(Classification Operation)

The obtained dried product was classified using a sieve having a sieve opening of 25 μm to obtain a classified product. The content of particles 25 μm or smaller in the obtained classified product was 0.8% by mass, and the average particle size was 55 μl.

(Calcination of Classified Product)

The obtained classified product was flowed at a rate of 20 kg/hr through a cylindrical calcining tube made of SUS, having an inner diameter of 500 mm, a length of 3,500 mm, and a thickness of 20 mm that was provided with seven weir plates having a height of 150 mm so that the length of the heating furnace section was divided into eight equal sections. Under a nitrogen gas flow of 600 NL/min, the temperature of the heating furnace was adjusted so as to have a temperature profile in which the temperature was increased to 370° C. over about four hours and kept at 370° C. for three hours while the calcining tube was being rotated at 4 rpm, to subject the classified product to pre-stage calcination, thereby obtaining a pre-stage calcined product. Then, the pre-stage calcined product was flowed at a rate of 15 kg/hr through another calcining tube made of SUS having an inner diameter of 500 mm, a length of 3,500 mm, and a thickness of 20 mm that was provided with seven weir plates having a height of 150 mm so that the length of the heating furnace section was divided into eight equal sections, while the calcining tube was being rotated at 4 rpm. At this time, while a portion of the pre-stage calcined product on the powder inlet side of the calcining tube (a portion not covered by the heating furnace) was being hammered once every five seconds from a height of 250 mm above the calcining tube in the direction perpendicular to the rotation axis by a hammering device equipped with a hammer having a mass of 14 kg with a hammering tip end made of SUS, and under a nitrogen gas flow of 500 NL/min, the temperature of the heating furnace was adjusted so as to have a temperature profile in which the temperature was increased to 690° C. at 2° C./min, calcination was carried out at 690° C. for three hours, and the temperature was reduced at 0.5° C./min, to carry out a main calcination, thereby obtaining an oxide catalyst.

(Composition of Oxide Catalyst)

Analysis of the oxide catalyst showed that a metal oxide had a composition of $MoV_{0.21}Nb_{0.09}Te_{0.20}W_{0.01}Ce_{0.01}$. Further, the support amount of silica was 47% by mass based on the total amount of the catalyst formed from a metal oxide and silica.

(Measurement of Specific Surface Area)

Based on a measurement carried out in the same manner as in Example 1, the specific surface area was 10.2 m²/g.

(Removal of Protruding Objects)

Protruding objects were removed in the same manner as in Example 1.

(Total Pore Volume)

Based on a measurement carried out in the same manner as in Example 1, the total pore volume was 0.235 cm³/g.

(Pore Distribution)

Based on a measurement carried out in the same manner as in Example 1, the pore volume ratio of pores having a pore size of less than 60 nm was 7.1%, and the pore volume ratio of pores having a pore size exceeding 120 nm was 0.7%.

(Calculation of Average Pore Size)

Based on a measurement carried out in the same manner as in Example 1, the average pore size was 92 nm.

(Measurement of Crystallite Size)

Based on a measurement carried out in the same manner as in Example 1, the crystallite size was 185 nm.

(Ammoxidation Reaction of Propane)

Propane was subjected to a vapor-phase ammoxidation reaction by the following method using the oxide catalyst obtained above. 35 g of the oxide catalyst was packed in a Vycor glass fluidized bed-type reaction tube having an inner diameter of 25 mm; and a mixed gas of propane:ammonia:oxygen:helium=1:1:3:18 in molar ratio was supplied for a contact time of 2.8 (sec·g/cc) at a reaction temperature of 440° C. under a reaction pressure of normal pressure. The ratio of propane conversion after the reaction was 88.8%, the yield of acrylonitrile was 54.8%, and the ammonia combustion rate was 19.0%.

Example 5

(Preparation of Niobium Raw Material Solution)

A niobium raw material solution was prepared in the same manner as in Example 1.

(Formulation of Raw Material-prepared Solution in a Formulation Tank)

19.9 kg of ammonium heptamolybdate $[(NH_4)_6Mo_7O_{24}·4H_2O]$. 2.75 kg of ammonium metavanadate $[NH_4VO_3]$, 3.28 kg of diantimony trioxide $[Sb_2O_3]$, and further an aqueous solution of cerium nitrate in which 495 g of cerium nitrate $[Ce(NO_3)_3·6H_2O]$ was dissolved in 2 kg of water were added to 100 kg of water, and heated under stirring for one hour at 95° C., thereby obtaining a raw material-prepared solution (I).

2.28 kg of a hydrogen peroxide solution containing 30% by mass of $H_2O_2$ was added to 15.95 kg of the niobium raw-material solution. The mixture was stirred and mixed at a solution temperature being kept at about 20° C., thereby obtaining a raw material-prepared solution (II).

The obtained raw material-prepared solution (I) was cooled to 70° C., and 31.0 kg of silica sol containing 30.2% by mass of $SiO_2$ and having an average primary particle size of 50 nm and 6.80 kg of silica sol containing 30.0% by mass of $SiO_2$ and having an average primary particle size of 18 nm were added. Then, 3.80 kg of a hydrogen peroxide solution containing 30% by mass of $H_2O_2$ was added, and stirred and mixed for 30 minutes at 55° C. Thereafter, the raw material-prepared solution (II), 258 g of an aqueous solution of ammonium metatungstate (50% purity), and 18.2 g of titanium oxide ($TiO_2$) were added. Further, 8.60 kg of a silica powder was dispersed in 77.4 kg of water, and the resultant mixture was aged as is for 1 hour at 50° C., thereby obtaining a raw material-prepared solution (III).

(Spray drying of Raw Material-prepared Solution Obtained in Formulation Tank)

Air heated to 210° C. and 50° C. hot water adjusted to a feed rate of 80 kg/Hr were fed to a centrifugal spray dryer until the formulation of the raw material-prepared solution (III) was complete; and the dryer inlet temperature was preset to 210° C. and the outlet temperature to 120° C.

When the feed amount of the raw material-prepared solution fed to the spray dryer was adjusted so that the spray dryer feed temperature did not fluctuate, the feed amount was 100 kg/Hr. During this period, the outlet temperature was 120±5° C., and did not greatly fluctuate.

(Measurement of UV-visible Reflectance Spectrum)

The obtained dried product was sampled each day. 0.5 g from the obtained 10 samples was tested using a JASCO UV/VIS Spectrometer V-650 manufactured by JASCO Corporation over a range of 200 to 800 nm based on a diffuse reflection method. Spectralon manufactured by Labsphere was used as a baseline reference material. The maximum absorbance value was 1.02. The absorbance at 600 nm was 0.31 to 0.36. Since this was an absorbance for which high performance could be expected based on the description in Japanese Patent Laid-Open No. 2009-148749, all of the spray-dried product was used in the classification operation without sorting.

(Classification Operation)

The obtained dried product was classified using a sieve having a sieve opening of 25 μm to obtain a classified product. The content of particles 25 μm or smaller in the obtained classified product was 0.8% by mass, and the average particle size was 55 μm.

(Calcination of Classified Product)

Classified products were calcined in the same manner as in Example 2.

(Composition of Oxide Catalyst)

Analysis of the oxide catalyst showed that a metal oxide had a composition of $MoV_{0.21}Nb_{0.09}Sb_{0.01}W_{0.005}Ti_{0.002}Ce_{0.01}$. Further, the support amount of silica was 47% by mass based on the total amount of the catalyst formed from a metal oxide and silica.

(Measurement of Specific Surface Area)

Based on a measurement carried out in the same manner as in Example, the specific surface area was 12.8 m²/g.

(Removal of Protruding Objects)

Protruding objects were removed in the same manner as in Example 1.

(Total Pore Volume)

Based on a measurement carried out in the same manner as in Example 1, the total pore volume was 0.288 cm³/g.

(Pore Distribution)

Based on a measurement carried out in the same manner as in Example 1, the pore volume ratio of pores having a pore size of less than 60 nm was 6.6%, and the pore volume ratio of pores having a pore size exceeding 120 nm was 0.5%.

(Calculation of Average Pore Size)

Based on a measurement carried out in the same manner as in Example 1, the average pore size was 90 nm.

(Measurement of Crystallite Size)

Based on a measurement carried out in the same manner as in Example 1, the crystallite size was 98 nm.

(Ammoxidation Reaction of Propane)

Propane was subjected to a vapor-phase ammoxidation reaction by the following method using the oxide catalyst obtained above. 35 g of the oxide catalyst was packed in a Vycor glass fluidized bed-type reaction tube having an inner diameter of 25 mm; and a mixed gas of propane:ammonia:oxygen:helium=1:1:3:18 in molar ratio was supplied for a contact time of 2.8 (sec·g/cc) at a reaction temperature of 440° C. under a reaction pressure of normal pressure. The ratio of propane conversion after the reaction was 88.8%, the yield of acrylonitrile was 54.6%, and the ammonia combustion rate was 19.5%.

Example 6

(Preparation of Niobium Raw Material Solution)

A niobium raw material solution was prepared in the same manner as in Example 1.

(Formulation of Raw Material-prepared Solution in a Formulation Tank)

19.9 kg of ammonium heptamolybdate $[(NH_4)_6Mo_7O_{24}\cdot 4H_2O]$, 2.75 kg of ammonium metavanadate $[NH_4VO_3]$, 3.28 kg of diantimony trioxide $[Sb_2O_3]$, and further an aqueous solution of cerium nitrate in which 495 g of cerium nitrate $[Ce(NO_3)_3\cdot 6H_2O]$ was dissolved in 2 kg of water were added to 100 kg of water, and heated under stirring for one hour at 95° C., thereby obtaining a raw material-prepared solution (I).

2.28 kg of a hydrogen peroxide solution containing 30% by mass of $H_2O_2$ was added to 15.95 kg of the niobium raw-material solution. The mixture was stirred and mixed at a solution temperature being kept at about 20° C., thereby obtaining a raw material-prepared solution (II).

The obtained raw material-prepared solution (I) was cooled to 70° C., and 31.0 kg of silica sol containing 30.2% by mass of $SiO_2$ and having an average primary particle size of 50 nm and 6.80 kg of silica sol containing 30.0% by mass of $SiO_2$ and having an average primary particle size of 18 nm were added. Then, 3.80 kg of a hydrogen peroxide solution containing 30% by mass of $H_2O_2$ was added, and stirred and mixed for 30 minutes at 55° C. Thereafter, the raw material-prepared solution (II), 258 g of an aqueous solution of ammonium metatungstate (50% purity), and 29.6 g of manganese oxide ($MnO_2$) were added. Further, 8.60 kg of a silica powder was dispersed in 77.4 kg of water, and the resultant mixture was aged as is for 1 hour at 50° C., thereby obtaining a raw material-prepared solution (III).

(Spray Drying of Raw Material-prepared Solution Obtained in Formulation Tank)

Air heated to 210° C. and 50° C. hot water adjusted to a feed rate of 80 kg/Hr were fed to a centrifugal spray dryer until the formulation of the raw material-prepared solution (III) was complete; and the dryer inlet temperature was preset to 210° C. and the outlet temperature to 120° C.

When the feed amount of the raw material-prepared solution fed to the spray dryer was adjusted so that the spray dryer feed temperature did not fluctuate, the feed amount was 100 kg/Hr. During this period, the outlet temperature was 120±5° C., and did not greatly fluctuate.

(Measurement of UV-visible Reflectance Spectrum)

The obtained dried product was sampled each day. 0.5 g from the obtained 10 samples was tested using a JASCO UV/VIS Spectrometer V-650 manufactured by JASCO Corporation over a range of 200 to 800 nm based on a diffuse reflection method. Spectralon manufactured by Labsphere was used as a baseline reference material. The maximum absorbance value was 1.02. The absorbance at 600 nm was 0.31 to 0.36. Since this was an absorbance for which high performance could be expected based on the description in Japanese Patent Laid-Open No. 2009-148749, all of the spray-dried product was used in the classification operation without sorting.

(Classification Operation)

The obtained dried product was classified using a sieve having a sieve opening of 25 μm to obtain a classified product. The content of particles 25 μm or smaller in the obtained classified product was 0.8% by mass, and the average particle size was 55 μm.

(Calcination of Classified Product)

Classified products were calcined in the same manner as in Example 2.

(Composition of Oxide Catalyst)

Analysis of the oxide catalyst showed that a metal oxide had a composition of $MoV_{0.21}Nb_{0.09}Sb_{0.20}W_{0.005}Mn_{0.003}Ce_{0.01}$. Further, the support amount of silica was 47% by mass based on the total amount of the catalyst formed from a metal oxide and silica.

(Measurement of Specific Surface Area)

Based on a measurement carried out in the same manner as in Example 1, the specific surface area was 13.2 m²/g.

(Removal of Protruding Objects)

Protruding objects were removed in the same manner as in Example 1.

(Measurement of Total Pore Volume)

Based on a measurement carried out in the same manner as in Example 1, the total pore volume was 0.304 cm³/g.

(Pore Distribution)

Based on a measurement carried out in the same manner as in Example 1, the pore volume ratio of pores having a pore size of less than 60 nm was 6.9%, and the pore volume ratio of pores having a pore size exceeding 120 nm was 0.6%.

(Calculation of Average Pore Size)

Based on a measurement carried out in the same manner as in Example 1, the average pore size was 92 nm.

(Measurement of Crystallite Size)

Based on a measurement carried out in the same manner as in Example 1, the crystallite size was 101 nm.

(Ammoxidation Reaction of Propane)

Propane was subjected to a vapor-phase ammoxidation reaction by the following method using the oxide catalyst obtained above. 35 g of the oxide catalyst was packed in a Vycor glass fluidized bed-type reaction tube having an inner diameter of 25 mm; and a mixed gas of propane:ammonia:oxygen:helium=1:1:3:18 in molar ratio was supplied for a contact time of 2.8 (sec·g/cc) at a reaction temperature of 440° C. under a reaction pressure of normal pressure. The ratio of propane conversion after the reaction was 88.8%, the yield of acrylonitrile was 54.7%, and the ammonia combustion rate was 19.3%.

Example 7

(Preparation of Niobium Raw Material Solution)

A niobium raw material solution was prepared in the same manner as in Example 1.

(Formulation of Raw Material-prepared Solution in a Formulation Tank)

19.9 kg of ammonium heptamolybdate $[(NH_4)_6Mo_7O_{24}\cdot 4H_2O]$, 2.75 kg of ammonium metavanadate $[NH_4VO_3]$, 3.28 kg of diantimony trioxide $[Sb_2O_3]$, and further an aqueous solution of cerium nitrate in which 495 g of cerium nitrate [Ce(NO$_3$)$_3$.6H$_2$O] was dissolved in 2 kg of water were added to 100 kg of water, and heated under stirring for one hour at 95° C., thereby obtaining a raw material-prepared solution (I).

2.28 kg of a hydrogen peroxide solution containing 30% by mass of H$_2$O$_2$ was added to 15.95 kg of the niobium raw-material solution. The mixture was stirred and mixed at a solution temperature being kept at about 20° C., thereby obtaining a raw material-prepared solution (II).

The obtained raw material-prepared solution (I) was cooled to 70° C., and 31.0 kg of silica sol containing 30.2% by mass of SiO$_2$ and having an average primary particle size of 50 nm and 6.80 kg of silica sol containing 30.0% by mass of SiO$_2$ and having an average primary particle size of 18 nm were added. Then, 3.80 kg of a hydrogen peroxide solution containing 30% by mass of H$_2$O$_2$ was added, and stirred and mixed for 30 minutes at 55° C. Thereafter, the raw material-prepared solution (II) and 155 g of an aqueous solution of ammonium metatungstate (50% purity) and 220 g of a bismuth nitrate[Bi(NO$_3$)$_3$.5H$_2$O] were added. Further, 8.60 kg of a silica powder was dispersed in 77.4 kg of water, and the resultant mixture was aged as is for one hour at 50° C., thereby obtaining a raw material-prepared solution (III).

(Spray Drying of Raw Material-prepared Solution Obtained in Formulation Tank)

Air heated to 210° C. and 50° C. hot water adjusted to a feed rate of 80 kg/Hr were fed to a centrifugal spray dryer until the formulation of the raw material-prepared solution (III) was complete; and the dryer inlet temperature was preset to 210° C. and the outlet temperature to 120° C.

When the feed amount of the raw material-prepared solution fed to the spray dryer was adjusted so that the spray dryer feed temperature did not fluctuate, the feed amount was 100 kg/Hr. During this period, the outlet temperature was 120±5° C., and did not greatly fluctuate.

(Measurement of UV-visible Reflectance Spectrum)

The obtained dried product was sampled each day. 0.5 g from the obtained 10 samples was tested using a JASCO UV/VIS Spectrometer V-650 manufactured by JASCO Corporation over a range of 200 to 800 nm based on a diffuse reflection method. Spectralon manufactured by Labsphere was used as a baseline reference material. The maximum absorbance value was 1.02. The absorbance at 600 nm was 0.31 to 0.36. Since this was an absorbance for which high performance could be expected based on the description in Japanese Patent Laid-Open No. 2009-148749, all of the spray-dried product was used in the classification operation without sorting.

(Classification Operation)

The obtained dried product was classified using a sieve having a sieve opening of 25 µm to obtain a classified product. The content of particles 25 µm or smaller in the obtained classified product was 0.8% by mass, and the average particle size was 55 µm.

(Calcination of Classified Product)

Classified products were calcined in the same manner as in Example 2.

(Composition of Oxide Catalyst)

Analysis of the oxide catalyst showed that a metal oxide had a composition of MoV$_{0.21}$Nb$_{0.09}$Sb$_{0.20}$W$_{0.003}$Bi$_{0.004}$Ce$_{0.01}$. Further, the support amount of silica was 47% by mass based on the total amount of the catalyst formed from a metal oxide and silica.

(Measurement of Specific Surface Area)

Based on a measurement carried out in the same manner as in Example 1, the specific surface area was 13.3 m$^2$/g.

(Removal of Protruding Objects)

Protruding objects were removed in the same manner as in Example 1.

(Total Pore Volume)

Based on a measurement carried out in the same manner as in Example 1, the total pore volume was 0.313 cm$^3$/g.

(Pore Distribution)

Based on a measurement carried out in the same manner as in Example 1, the pore volume ratio of pores having a pore size of less than 60 nm was 7.3%, and the pore volume ratio of pores having a pore size exceeding 120 nm was 0.8%.

(Calculation of Average Pore Size)

Based on a measurement carried out in the same manner as in Example 1, the average pore size was 94 nm.

(Measurement of Crystallite Size)

Based on a measurement carried out in the same manner as in Example 1, the crystallite size was 103 nm.

(Ammoxidation Reaction of Propane)

Propane was subjected to a vapor-phase ammoxidation reaction by the following method using the oxide catalyst obtained above. 35 g of the oxide catalyst was packed in a Vycor glass fluidized bed-type reaction tube having an inner diameter of 25 mm; and a mixed gas of propane:ammonia: oxygen:helium=1:1:3:18 in molar ratio was supplied for a contact time of 2.8 (sec·g/cc) at a reaction temperature of 440° C. under a reaction pressure of normal pressure. The ratio of propane conversion after the reaction was 88.8%, the yield of acrylonitrile was 54.6%, and the ammonia combustion rate was 19.2%.

Example 8

(Preparation of Niobium Raw Material Solution)

A niobium raw material solution was prepared in the same manner as in Example 1.

(Formulation of Raw Material-prepared Solution in a Formulation Tank)

19.9 kg of ammonium heptamolybdate [(NH$_4$)$_6$Mo$_7$O$_{24}$.4H$_2$O], 2.75 kg of ammonium metavanadate [NH$_4$VO$_3$], 3.28 kg of diantimony trioxide [Sb$_2$O$_3$], and further an aqueous solution of cerium nitrate in which 347 g of cerium nitrate [Ce(NO$_3$)$_3$.6H$_2$O] and 147 g of lanthanum nitrate [La(NO$_3$)$_3$.6H$_2$O] were dissolved in 2 kg of water were added to 100 kg of water, and heated under stirring for one hour at 95° C., thereby obtaining a raw material-prepared solution (I).

2.28 kg of a hydrogen peroxide solution containing 30% by mass of H$_2$O$_2$ was added to 15.95 kg of the niobium raw-material solution. The mixture was stirred and mixed at a solution temperature being kept at about 20° C., thereby obtaining a raw material-prepared solution (II).

The obtained raw material-prepared solution (I) was cooled to 70° C., and 31.0 kg of silica sol containing 30.2% by mass of SiO$_2$ and having an average primary particle size of 50 nm and 7.70 kg of silica sol containing 30.0% by mass of SiO$_2$ and having an average primary particle size of 18 nm were added. Then, 3.80 kg of a hydrogen peroxide solution containing 30% by mass of H$_2$O$_2$ was added, and stirred and mixed for 30 minutes at 55° C. Thereafter, the raw material-prepared solution (II) and 516 g of an aqueous solution of ammonium metatungstate (50% purity) were added. Further, 8.60 kg of a silica powder was dispersed in 77.4 kg of water, and the resultant mixture was aged as is for one hour at 50° C., thereby obtaining a raw material-prepared solution (III).

(Spray Drying of Raw Material-prepared Solution Obtained in Formulation Tank)

Air heated to 210° C. and 50° C. hot water adjusted to a feed rate of 80 kg/Hr were fed to a centrifugal spray dryer until the formulation of the raw material-prepared solution (III) was complete; and the dryer inlet temperature was preset to 210° C. and the outlet temperature to 120° C.

When the feed amount of the raw material-prepared solution fed to the spray dryer was adjusted so that the spray dryer feed temperature did not fluctuate, the feed amount was 100 kg/Hr. During this period, the outlet temperature was 120±5° C., and did not greatly fluctuate.

(Measurement of UV-visible Reflectance Spectrum)

The obtained dried product was sampled each day. 0.5 g from the obtained 10 samples was tested using a JASCO UV/VIS Spectrometer V-650 manufactured by JASCO Corporation over a range of 200 to 800 nm based on a diffuse reflection method. Spectralon manufactured by Labsphere was used as a baseline reference material. The maximum absorbance value was 1.02. The absorbance at 600 nm was 0.31 to 0.36. Since this was an absorbance for which high performance could be expected based on the description in Japanese Patent Laid-Open No. 2009-148749, all of the spray-dried product was used in the classification operation without sorting.

(Classification Operation)

The obtained dried product was classified using a sieve having a sieve opening of 25 μm to obtain a classified product. The content of particles 25 μm or smaller in the obtained classified product was 0.8% by mass, and the average particle size was 55 μm.

(Calcination of Classified Product)

Classified products were calcined in the same manner as in Example 2.

(Composition of Oxide Catalyst)

Analysis of the oxide catalyst showed that a metal oxide had a composition of $MoV_{0.21}Nb_{0.09}Sb_{0.20}W_{0.01}Ce_{0.007}La_{0.003}$. Further, the support amount of silica was 47% by mass based on the total amount of the catalyst formed from a metal oxide and silica.

(Measurement of Specific Surface Area)

Based on a measurement carried out in the same manner as in Example 1, the specific surface area was 14.2 $m^2/g$.

(Removal of Protruding Objects)

Protruding objects were removed in the same manner as in Example 1.

(Total Pore Volume)

Based on a measurement carried out in the same manner as in Example 1, the total pore volume was 0.320 $cm^3/g$.

(Pore Distribution)

Based on a measurement carried out in the same manner as in Example 1, the pore volume ratio of pores having a pore size of less than 60 nm was 6.7%, and the pore volume ratio of pores having a pore size exceeding 120 nm was 0.4%.

(Measurement of Pore Distribution)

Based on a measurement carried out in the same manner as in Example 1, the average pore size was 90 nm.

(Calculation of Average Pore Size)

Based on a measurement carried out in the same manner as in Example 1, the crystallite size was 95 nm.

(Ammoxidation Reaction of Propane)

Propane was subjected to a vapor-phase ammoxidation reaction by the following method using the oxide catalyst obtained above. 35 g of the oxide catalyst was packed in a Vycor glass fluidized bed-type reaction tube having an inner diameter of 25 mm; and a mixed gas of propane:ammonia: oxygen:helium=1:1:3:18 in molar ratio was supplied for a contact time of 2.8 (sec·g/cc) at a reaction temperature of 440° C. under a reaction pressure of normal pressure. The ratio of propane conversion after the reaction was 88.8%, the yield of acrylonitrile was 54.6%, and the ammonia combustion rate was 18.8%.

Example 9

(Preparation of Niobium Raw Material Solution)

A niobium raw material solution was prepared in the same manner as in Example 1.

(Formulation of Raw Material-prepared Solution in a Formulation Tank)

19.9 kg, of ammonium heptamolybdate $[(NH_4)_6Mo_7O_{24}\cdot 4H_2O]$. 2.75 kg of ammonium metavanadate $[NH_4VO_3]$, 3.28 kg of diantimony trioxide $[Sb_2O_3]$, and further an aqueous solution of cerium nitrate in which 397 g of cerium nitrate $[Ce(NO_3)_3\cdot 6H_2O]$ and 87 g of lanthanum nitrate $[Y(NO_3)_3\cdot 6H_2O]$ was dissolved in 2 kg of water were added to 100 kg of water, and heated under stirring for one hour at 95° C., thereby obtaining a raw material-prepared solution (I).

2.28 kg of a hydrogen peroxide solution containing 30% by mass of $H_2O_2$ was added to 15.95 kg of the niobium raw-material solution. The mixture was stirred and mixed at a solution temperature being kept at about 20° C., thereby obtaining a raw material-prepared solution (II).

The obtained raw material-prepared solution (I) was cooled to 70° C., and 31.0 kg of silica sol containing 30.2% by mass of $SiO_2$ and having an average primary particle size of 50 nm and 7.70 kg of silica sol containing 30.0% by mass of $SiO_2$ and having an average primary particle size of 18 nm were added. Then, 3.80 kg of a hydrogen peroxide solution containing 30% by mass of $H_2O_2$ was added, and stirred and mixed for 30 minutes at 55° C. Thereafter, the raw material-prepared solution (II) and 516 g of an aqueous solution of ammonium metatungstate (50% purity) were added. Further, 8.60 kg of a silica powder was dispersed in 77.4 kg of water, and the resultant mixture was aged as is for one hour at 50° C., thereby obtaining a raw material-prepared solution (III).

(Spray Drying of Raw Material-prepared Solution Obtained in Formulation Tank)

Air heated to 210° C. and 50° C. hot water adjusted to a feed rate of 80 kg/Hr were fed to a centrifugal spray dryer until the formulation of the raw material-prepared solution (III) was complete; and the dryer inlet temperature was preset to 210° C. and the outlet temperature to 120° C.

When the feed amount of the raw material-prepared solution fed to the spray dryer was adjusted so that the spray dryer feed temperature did not fluctuate, the feed amount was 100 kg/Hr. During this period, the outlet temperature was 120±5° C., and did not greatly fluctuate.

(Measurement of UV-visible Reflectance Spectrum)

The obtained dried product was sampled each day. 0.5 g from the obtained 10 samples was tested using a JASCO UV/VIS Spectrometer V-650 manufactured by JASCO Corporation over a range of 200 to 800 nm based on a diffuse reflection method. Spectralon manufactured by Labsphere was used as a baseline reference material. The maximum absorbance value was 1.02. The absorbance at 600 nm was 0.31 to 0.36. Since this was an absorbance for which high performance could be expected based on the description in Japanese Patent Laid-Open No. 2009-148749, all of the spray-dried product was used in the classification operation without sorting.

(Classification Operation)

The obtained dried product was classified using a sieve having a sieve opening of 25 μm to obtain a classified product.

The content of particles 25 μm or smaller in the obtained classified product was 0.8% by mass, and the average particle size was 55 μm.
(Calcination of Classified Product)
Classified products were calcined in the same manner as in Example 2.
(Composition of Oxide Catalyst)
Analysis of the oxide catalyst showed that a metal oxide had a composition of $MoV_{0.21}Nb_{0.09}Sb_{0.20}W_{0.01}Ce_{0.008}Y_{0.002}$. Further, the support amount of silica was 47% by mass based on the total amount of the catalyst formed from a metal oxide and silica.
(Measurement of Specific Surface Area)
Based on a measurement carried out in the same manner as in Example 1, the specific surface area was 14.5 m²/g.
(Removal of Protruding Objects)
Protruding objects were removed in the same manner as in Example 1.
(Total Pore Volume)
Based on a measurement carried out in the same manner as in Example 1, the total pore volume was 0.330 cm³/g.
(Pore Distribution)
Based on a measurement carried out in the same manner as in Example 1, the pore volume ratio of pores having a pore size of less than 60 nm was 7.2%, and the pore volume ratio of pores having a pore size exceeding 120 nm was 0.5%.
(Calculation of Average Pore Size)
Based on a measurement carried out in the same manner as in Example 1, the average pore size was 91 nm.
(Measurement of Crystallite Size)
Based on a measurement carried out in the same manner as in Example 1, the crystallite size was 102 nm.
(Ammoxidation Reaction of Propane)
Propane was subjected to a vapor-phase ammoxidation reaction by the following method using the oxide catalyst obtained above. 35 g of the oxide catalyst was packed in a Vycor glass fluidized bed-type reaction tube having an inner diameter of 25 mm; and a mixed gas of propane:ammonia: oxygen:helium=1:1:3:18 in molar ratio was supplied for a contact time of 2.8 (sec·g/cc) at a reaction temperature of 440° C. under a reaction pressure of normal pressure. The ratio of propane conversion after the reaction was 88.8%, the yield of acrylonitrile was 54.7%, and the ammonia combustion rate was 18.9%.

Example 10

(Preparation of Niobium Raw Material Solution)
A niobium raw material solution was prepared in the same manner as in Example 1.
(Formulation of Raw Material-prepared Solution in a Formulation Tank)
19.9 kg of ammonium heptamolybdate [$(NH_4)_6Mo_7O_{24}.4H_2O$], 2.75 kg of ammonium metavanadate [$NH_4VO_3$], 3.28 kg of diantimony trioxide [$Sb_2O_3$], and further an aqueous solution of cerium nitrate in which 297 g of cerium nitrate [$Ce(NO_3)_3.6H_2O$] and 146 g of lanthanum nitrate [$Yb(NO_3)_3.4H_2O$] was dissolved in 2 kg of water were added to 100 kg of water, and heated under stirring for one hour at 95° C., thereby obtaining a raw material-prepared solution (I).
2.28 kg of a hydrogen peroxide solution containing 30% by mass of $H_2O_2$ was added to 15.95 kg of the niobium raw-material solution. The mixture was stirred and mixed at a solution temperature being kept at about 20° C., thereby obtaining a raw material-prepared solution (II).

The obtained raw material-prepared solution (I) was cooled to 70° C., and 31.0 kg of silica sol containing 30.2% by mass of $SiO_2$ and having an average primary particle size of 50 nm and 6.80 kg of silica sol containing 30.0% by mass of $SiO_2$ and having an average primary particle size of 18 nm were added. Then, 3.80 g of a hydrogen peroxide solution containing 30% by mass of $H_2O_2$ was added, and stirred and mixed for 30 minutes at 55° C. Thereafter, the raw material-prepared solution (II) and 516 g of an aqueous solution of ammonium metatungstate (50% purity) were added. Further, 8.60 kg of a silica powder was dispersed in 77.4 kg of water, and the resultant mixture was aged as is for one hour at 50° C., thereby obtaining a raw material-prepared solution (III).
(Spray drying of Raw Material-prepared Solution Obtained in Formulation Tank)
Air heated to 210° C. and 50° C. hot water adjusted to a feed rate of 80 kg/Hr were fed to a centrifugal spray dryer until the formulation of the raw material-prepared solution (III) was complete; and the dryer inlet temperature was preset to 210° C. and the outlet temperature to 120° C.
When the feed amount of the raw material-prepared solution fed to the spray dryer was adjusted so that the spray dryer feed temperature did not fluctuate, the feed amount was 100 kg/Hr. During this period, the outlet temperature was 120±5° C., and did not greatly fluctuate.
(Measurement of UV-visible Reflectance Spectrum)
The obtained dried product was sampled each day. 0.5 g from the obtained 10 samples was tested using a JASCO UV/VIS Spectrometer V-650 manufactured by JASCO Corporation over a range of 200 to 800 nm based on a diffuse reflection method. Spectralon manufactured by Labsphere was used as a baseline reference material. The maximum absorbance value was 1.02. The absorbance at 600 nm was 0.31 to 0.36. Since this was an absorbance for which high performance could be expected based on the description in Japanese Patent Laid-Open No. 2009-148749, all of the spray-dried product was used in the classification operation without sorting.
(Classification Operation)
The obtained dried product was classified using a sieve having a sieve opening of 25 μm to obtain a classified product. The content of particles 25 μm or smaller in the obtained classified product was 0.8% by mass, and the average particle size was 55 μm.
(Calcination of Classified Product)
Classified products were calcined in the same manner as in Example 2.
(Composition of Oxide Catalyst)
Analysis of the oxide catalyst showed that a metal oxide had a composition of $MoV_{0.21}Nb_{0.09}Sb_{0.20}W_{0.01}Ce_{0.006}Yb_{0.003}$. Further, the support amount of silica was 47% by mass based on the total amount of the catalyst formed from a metal oxide and silica.
(Measurement of Specific Surface Area)
Based on a measurement carried out in the same manner as in Example 1, the specific surface area was 15.2 m²/g.
(Removal of Protruding Objects)
Protruding objects were removed in the same manner as in Example 1.
(Total Pore Volume)
Based on a measurement carried out in the same manner as in Example 1, the total pore volume was 0.334 cm³/g.
(Pore Distribution)
Based on a measurement carried out in the same manner as in Example 1, the pore volume ratio of pores having a pore size of less than 60 nm was 8.2%, and the pore volume ratio of pores having a pore size exceeding 120 nm was 0.4%.

(Calculation of Average Pore Size)

Based on a measurement carried out in the same manner as in Example 1, the average pore size was 88 nm.

(Measurement of Crystallite Size)

Based on a measurement carried out in the same manner as in Example 1, the crystallite size was 98 nm.

(Ammoxidation Reaction of Propane)

Propane was subjected to a vapor-phase ammoxidation reaction by the following method using the oxide catalyst obtained above. 35 g of the oxide catalyst was packed in a Vycor glass fluidized bed-type reaction tube having an inner diameter of 25 mm; and a mixed gas of propane:ammonia:oxygen:helium=1:1:3:18 in molar ratio was supplied for a contact time of 2.8 (sec·g/cc) at a reaction temperature of 440° C. under a reaction pressure of normal pressure. The ratio of propane conversion after the reaction was 88.8%, the yield of acrylonitrile was 54.6%, and the ammonia combustion rate was 19.0%.

Example 11

(Preparation of Niobium Raw Material Solution)

A niobium raw material solution was prepared in the same manner as in Example 1.

(Formulation of Raw Material-prepared Solution in a Formulation Tank)

19.9 kg of ammonium heptamolybdate [$(NH_4)_6Mo_7O_{24} \cdot 4H_2O$], 2.75 kg of ammonium metavanadate [$NH_4VO_3$], 3.28 kg of diantimony trioxide [$Sb_2O_3$], and further an aqueous solution of cerium nitrate in which 495 g of cerium nitrate [$Ce(NO_3)_3 \cdot 6H_2O$] was dissolved in 2 kg of water were added to 100 kg of water, and heated under stirring for one hour at 95° C., thereby obtaining a raw material-prepared solution (I).

2.28 kg of a hydrogen peroxide solution containing 30% by mass of $H_2O_2$ was added to 15.95 kg of the niobium raw-material solution. The mixture was stirred and mixed at a solution temperature being kept at about 20° C., thereby obtaining a raw material-prepared solution (II).

The obtained raw material-prepared solution (I) was cooled to 70° C., and 31.0 kg of silica sol containing 30.2% by mass of $SiO_2$ and having an average primary particle size of 23 nm and 6.80 kg of silica sol containing 30.0% by mass of $SiO_2$ and having an average primary particle size of 13 nm were added. Then, 3.80 kg of a hydrogen peroxide solution containing 30% by mass of $H_2O_2$ was added, and stirred and mixed for 30 minutes at 55° C. Thereafter, the raw material-prepared solution (II) and 516 g of an aqueous solution of ammonium metatungstate (50% purity) were added. Further, 8.60 kg of a silica powder was dispersed in 77.4 kg of water, and the resultant mixture was aged as is for one hour at 50° C., thereby obtaining a raw material-prepared solution (III).

(Spray Drying of Raw Material-prepared Solution Obtained in Formulation Tank)

Air heated to 210° C. and 50° C. hot water adjusted to a feed rate of 80 kg/Hr were fed to a centrifugal spray dryer until the formulation of the raw material-prepared solution (III) was complete; and the dryer inlet temperature was preset to 210° C. and the outlet temperature to 120° C.

When the feed amount of the raw material-prepared solution fed to the spray dryer was adjusted so that the spray dryer feed temperature did not fluctuate, the feed amount was 100 kg/Hr. During this period, the outlet temperature was 120±5° C., and did not greatly fluctuate.

(Measurement of UV-visible Reflectance Spectrum)

The obtained dried product was sampled each day. 0.5 g from the obtained 10 samples was tested using a JASCO UV/VIS Spectrometer V-650 manufactured by JASCO Corporation over a range of 200 to 800 nm based on a diffuse reflection method. Spectralon manufactured by Labsphere was used as a baseline reference material. The maximum absorbance value was 1.02. The absorbance at 600 nm was 0.31 to 0.36. Since this was an absorbance for which high performance could be expected based on the description in Japanese Patent Laid-Open No. 2009-148749, all of the spray-dried product was used in the classification operation without sorting.

(Classification Operation)

The obtained dried product was classified using a sieve having a sieve opening of 25 μm to obtain a classified product. The content of particles 25 μm or smaller in the obtained classified product was 0.8% by mass, and the average particle size was 55 μm.

(Calcination of Classified Product)

The obtained classified product was flowed at a rate of 20 kg/hr through a cylindrical calcining tube made of SUS, having an inner diameter of 500 mm, a length of 3,500 mm, and a thickness of 20 mm that was provided with seven weir plates having a height of 150 mm so that the length of the heating furnace section was divided into eight equal sections. Under a nitrogen gas flow of 600 NL/min, the temperature of the heating furnace was adjusted so as to have a temperature profile in which the temperature was increased to 370° C. over about four hours and kept at 370° C. for three hours while the calcining tube was being rotated at 4 rpm, to subject the classified product to pre-stage calcination, thereby obtaining a pre-stage calcined product. Then, the pre-stage calcined product was flowed at a rate of 15 kg/hr through another calcining tube made of SUS having an inner diameter of 500 mm, a length of 3,500 mm, and a thickness of 20 mm that was provided with seven weir plates having a height of 150 mm so that the length of the heating section was divided into eight equal sections, while the calcining tube was being rotated at 4 rpm. At this time, while a portion of the pre-stage calcined product on the powder inlet side of the calcining tube (a portion not covered by the heating furnace) was being hammered once every five seconds from a height of 250 mm above the calcining tube in the direction perpendicular to the rotation axis by a hammering device equipped with a hammer having a mass of 14 kg with a hammering tip end made of SUS, and under a nitrogen gas flow of 500 NL/min, the temperature of the heating furnace was adjusted so as to have a temperature profile in which the temperature was increased to 680° C. at 2° C./min, calcination was carried out at 680° C. for two hours, and the temperature was reduced at 1° C./min, to carry out a main calcination, thereby obtaining an oxide catalyst.

(Composition of Oxide Catalyst)

Analysis of the oxide catalyst showed that a metal oxide had a composition ratio of $MoV_{0.21}Nb_{0.09}Sb_{0.20}W_{0.01}Ce_{0.01}$. Further, the support amount of silica was 47% by mass based on the total amount of the catalyst formed from a metal oxide and silica.

(Measurement of Specific Surface Area)

Based on a measurement carried out in the same manner as in Example 1, the specific surface area was 14.6 m²/g.

(Removal of Protruding Objects)

Protruding objects were removed in the same manner as in Example 1.

(Total Pore Volume)

Based on a measurement carried out in the same manner as in Example 1, the total pore volume was 0.350 cm³/g.

(Pore Distribution)

Based on a measurement carried out in the same manner as in Example 1, the pore volume ratio of pores having a pore size of less than 60 nm was 5.8%, and the pore volume ratio of pores having a pore size exceeding 120 nm was 0.9%.

(Calculation of Average Pore Size)

Based on a measurement carried out in the same manner as in Example 1, the average pore size was 96 nm.

(Measurement of Crystallite Size)

Based on a measurement carried out in the same manner as in Example 1, the crystallite size was 61 nm.

(Ammoxidation Reaction of Propane)

Propane was subjected to a vapor-phase ammoxidation reaction by the following method using the oxide catalyst obtained above. 35 g of the oxide catalyst was packed in a Vycor glass fluidized bed-type reaction tube having an inner diameter of 25 mm; and a mixed gas of propane:ammonia:oxygen:helium=1:1:3:18 in molar ratio was supplied for a contact time of 2.8 (sec·g/cc) at a reaction temperature of 440° C. under a reaction pressure of normal pressure. The ratio of propane conversion after the reaction was 88.9%, the yield of acrylonitrile was 54.4%, and the ammonia combustion rate was 19.1%.

Example 12

(Preparation of Niobium Raw Material Solution)

A niobium raw material solution was prepared in the same manner as in Example 1.

(Formulation of Raw Material-prepared Solution in a Formulation Tank)

19.9 kg of ammonium heptamolybdate [$(NH_4)_6Mo_7O_{24} \cdot 4H_2O$], 2.75 kg of ammonium metavanadate [$NH_4VO_3$], 3.28 kg of diantimony trioxide [$Sb_2O_3$], and further an aqueous solution of cerium nitrate in which 495 g of cerium nitrate [$Ce(NO_3)_3 \cdot 6H_2O$] was dissolved in 2 kg of water were added to 100 kg of water, and heated under stirring for one hour at 95° C., thereby obtaining a raw material-prepared solution (I).

2.28 kg of a hydrogen peroxide solution containing 30% by mass of $H_2O_2$ was added to 15.95 kg of the niobium raw-material solution. The mixture was stirred and mixed at a solution temperature being kept at about 20° C., thereby obtaining a raw material-prepared solution (II).

The obtained raw material-prepared solution (I) was cooled to 70° C., and 31.0 kg of silica sol containing 30.2% by mass of $SiO_2$ and having an average primary particle size of 23 nm and 6.80 kg of silica sol containing 30.0% by mass of $SiO_2$ and having an average primary particle size of 13 nm were added. Then, 3.80 kg of a hydrogen peroxide solution containing 30% by mass of $H_2O_2$ was added, and stirred and mixed for 30 minutes at 55° C. Thereafter, the raw material-prepared solution (II) and 516 g of an aqueous solution of ammonium metatungstate (50% purity) were added. Further, 8.60 kg of a silica powder was dispersed in 77.4 kg of water, and the resultant mixture was aged as is for one hour at 50° C., thereby obtaining a raw material-prepared solution (III).

(Spray Drying of Raw Material-prepared Solution Obtained in Formulation Tank)

Air heated to 210° C. and 50° C. hot water adjusted to a feed rate of 80 kg/Hr were fed to a centrifugal spray dryer until the formulation of the raw material-prepared solution (III) was complete; and the dryer inlet temperature was preset to 210° C. and the outlet temperature to 120° C.

When the feed amount of the raw material-prepared solution fed to the spray dryer was adjusted so that the spray dryer feed temperature did not fluctuate, the feed amount was 100 kg/Hr. During this period, the outlet temperature was 120±5° C., and did not greatly fluctuate.

(Measurement of UV-visible Reflectance Spectrum)

The obtained dried product was sampled each day. 0.5 g from the obtained 10 samples was tested using a JASCO UV/VIS Spectrometer V-650 manufactured by JASCO Corporation over a range of 200 to 800 nm based on a diffuse reflection method. Spectralon manufactured by Labsphere was used as a baseline reference material. The maximum absorbance value was 1.02. The absorbance at 600 nm was 0.31 to 0.36. Since this was an absorbance for which high performance could be expected based on the description in Japanese Patent Laid-Open No. 2009-148749, all of the spray-dried product was used in the classification operation without sorting.

(Classification Operation)

The obtained dried product was classified using a sieve having a sieve opening of 25 μm to obtain a classified product. The content of particles 25 μm or smaller in the obtained classified product was 0.8% by mass, and the average particle size was 55 μm.

(Calcination of Classified Product)

The obtained classified product was flowed at a rate of 20 kg/hr through a cylindrical calcining tube made of SUS, having an inner diameter of 500 mm, a length of 3,500 mm, and a thickness of 20 mm that was provided with seven weir plates having a height of 150 mm so that the length of the heating furnace section was divided into eight equal sections. Under a nitrogen gas flow of 600 NL/min, the temperature of the heating furnace was adjusted so as to have a temperature profile in which the temperature was increased to 370° C. over about four hours and kept at 370° C. for three hours while the calcining tube was being rotated at 4 rpm, to subject the classified product to pre-stage calcination, thereby obtaining a pre-stage calcined product. Then, the pre-stage calcined product was flowed at a rate of 15 kg/hr through another calcining tube made of SUS having an inner diameter of 500 mm, a length of 3,500 mm, and a thickness of 20 mm that was provided with seven weir plates having a height of 150 mm so that the length of the heating section was divided into eight equal sections, while the calcining tube was being rotated at 4 rpm. At this time, while a portion of the pre-stage calcined product on the powder inlet side of the calcining tube (a portion not covered by the heating furnace) was being hammered once every five seconds from a height of 250 mm above the calcining tube in the direction perpendicular to the rotation axis by a hammering device equipped with a hammer having a mass of 14 kg with a hammering tip end made of SUS, and under a nitrogen gas flow of 500 NL/min, the temperature of the heating furnace was adjusted so as to have a temperature profile in which the temperature was increased to 685° C. at 2° C./rain, calcination was carried out at 685° C. for two and half hours, and the temperature was reduced at 1° C./min, to carry out a main calcination, thereby obtaining an oxide catalyst.

(Composition of Oxide Catalyst)

Analysis of the oxide catalyst showed that a metal oxide had a composition of $MoV_{0.21}Nb_{0.09}Sb_{0.20}W_{0.01}Ce_{0.01}$. Further, the support amount of silica was 47% by mass based on the total amount of the catalyst formed from a metal oxide and silica.

(Measurement of Specific Surface Area)

Based on a measurement carried out in the same manner as in Example 1, the specific surface area was 15.1 m²/g.

(Removal of Protruding Objects)

Protruding objects were removed in the same manner as in Example 1.

(Total Pore Volume)

Based on a measurement carried out in the same manner as in Example 1, the total pore volume was 0.306 cm$^3$/g.

(Pore Distribution)

Based on a measurement carried out in the same manner as in Example 1, the pore volume ratio of pores having a pore size of less than 60 nm was 9.3%, and the pore volume ratio of pores having a pore size exceeding 120 nm was 0.3%.

(Calculation of Average Pore Size)

Based on a measurement carried out in the same manner as in Example 1, the average pore size was 81 nm.

(Measurement of crystallite size)

Based on a measurement carried out in the same manner as in Example 1, the crystallite size was 181 nm.

(Ammoxidation Reaction of Propane)

Propane was subjected to a vapor-phase ammoxidation reaction by the following method using the oxide catalyst obtained above. 35 g of the oxide catalyst was packed in a Vycor glass fluidized bed-type reaction tube having an inner diameter of 25 mm; and a mixed gas of propane:ammonia:oxygen:helium=1:1:3:18 in molar ratio was supplied for a contact time of 2.8 (sec·g/cc) at a reaction temperature of 440° C. under a reaction pressure of normal pressure. The ratio of propane conversion after the reaction was 89.1%, the yield of acrylonitrile was 54.3%, and the ammonia combustion rate was 19.4%.

Example 13

(Preparation of Niobium Raw Material Solution)

A niobium raw material solution was prepared in the same manner as in Example 1.

(Formulation of Raw Material-prepared Solution in a Formulation Tank)

19.9 kg of ammonium heptamolybdate [(NH$_4$)$_6$Mo$_7$O$_{24}$.4H$_2$O], 2.75 kg of ammonium metavanadate [NH$_4$VO$_3$], 3.28 kg of diantimony trioxide [Sb$_2$O$_3$], and further an aqueous solution of cerium nitrate in which 495 g of cerium nitrate [Ce(NO$_3$)$_3$.6H$_2$O] was dissolved in 2 kg of water were added to 100 kg of water, and heated under stirring for one hour at 95° C., thereby obtaining a raw material-prepared solution (I).

2.28 kg of a hydrogen peroxide solution containing 30% by mass of H$_2$O$_2$ was added to 15.95 kg of the niobium raw-material solution. The mixture was stirred and mixed at a solution temperature being kept at about 20° C., thereby obtaining a raw material-prepared solution (II).

The obtained raw material-prepared solution (I) was cooled to 70° C., and 34.0 kg of silica sol containing 30.2% by mass of SiO$_2$ and having an average primary particle size of 55 nm and 3.80 kg of silica sol containing 30.0% by mass of SiO$_2$ and having an average primary particle size of 13 nm were added. Then, 3.80 kg of a hydrogen peroxide solution containing 30% by mass of H$_2$O$_2$ was added, and stirred and mixed for 30 minutes at 55° C. Thereafter, the raw material-prepared solution (II) and 516 g of an aqueous solution of ammonium metatungstate (50% purity) were added. Further, 8.60 kg of a silica powder was dispersed in 77.4 kg of water, and the resultant mixture was aged as is for one hour at 50° C., thereby obtaining a raw material-prepared solution (III).

(Spray Drying of Raw Material-prepared Solution Obtained in Formulation Tank)

Air heated to 210° C. and 50° C. hot water adjusted to a feed rate of 80 kg/Hr were fed to a centrifugal spray dryer until the formulation of the raw material-prepared solution (III) was complete; and the dryer inlet temperature was preset to 210° C. and the outlet temperature to 120° C.

When the feed amount of the raw material-prepared solution fed to the spray dryer was adjusted so that the spray dryer feed temperature did not fluctuate, the feed amount was 100 kg/Hr. During this period, the outlet temperature was 120±5° C., and did not greatly fluctuate.

(Measurement of UV-visible Reflectance Spectrum)

The obtained dried product was sampled each day. 0.5 g from the obtained 10 samples was tested using a JASCO UV/VIS Spectrometer V-650 manufactured by JASCO Corporation over a range of 200 to 800 nm based on a diffuse reflection method. Spectralon manufactured by Labsphere was used as a baseline reference material. The maximum absorbance value was 1.02. The absorbance at 600 nm was 0.31 to 0.36. Since this was an absorbance for which high performance could be expected based on the description in Japanese Patent Laid-Open No. 2009-148749, all of the spray-dried product was used in the classification operation without sorting.

(Classification Operation)

The obtained dried product was classified using a sieve having a sieve opening of 25 μm to obtain a classified product. The content of particles 25 μm or smaller in the obtained classified product was 0.8% by mass, and the average particle size was 55 μm.

(Calcination of Classified Product)

The obtained classified product was flowed at a rate of 20 kg/hr through a cylindrical calcining tube made of SUS, having an inner diameter of 500 mm, a length of 3,500 mm, and a thickness of 20 mm that was provided with seven weir plates having a height of 150 mm so that the length of the heating furnace section was divided into eight equal sections. Under a nitrogen gas flow of 600 NL/min, the temperature of the heating furnace was adjusted so as to have a temperature profile in which the temperature was increased to 370° C. over about four hours and kept at 370° C. for three hours while the calcining tube was being rotated at 4 rpm, to subject the classified product to pre-stage calcination, thereby obtaining a pre-stage calcined product. Then, the pre-stage calcined product was flowed at a rate of 15 kg/hr through another calcining tube made of SUS having an inner diameter of 500 mm, a length of 3,500 mm, and a thickness of 20 mm that was provided with seven weir plates having a height of 150 mm so that the length of the heating section was divided into eight equal sections, while the tube was being rotated at 4 rpm. At this time, while a portion of the pre-stage calcined product on the powder inlet side of the calcining tube (a portion not covered by the heating furnace) was being hammered once every five seconds from a height of 250 mm above the calcining tube in the direction perpendicular to the rotation axis by a hammering device equipped with a hammer having a mass of 14 kg with a hammering tip end made of SUS, and under a nitrogen gas flow of 500 NL/min, the temperature of the heating furnace was adjusted so as to have a temperature profile in which the temperature was increased to 695° C. at 2° C./min, calcination was carried out at 695° C. for two hours, and the temperature was reduced at 1° C./min, to carry out a main calcination, thereby obtaining an oxide catalyst.

(Composition of Oxide Catalyst)

Analysis of the oxide catalyst showed that a metal oxide had a composition of MoV$_{0.21}$Nb$_{0.09}$Sb$_{0.20}$W$_{0.01}$Ce$_{0.01}$. Further, the support amount of silica was 47% by mass based on the total amount of the catalyst formed from a metal oxide and silica.

(Measurement of Specific Surface Area)

Based on a measurement carried out in the same manner as in Example 1, the specific surface area was 8.0 m$^2$/g.

(Removal of Protruding Objects)
Protruding objects were removed in the same manner as in Example 1.
(Total Pore Volume)
Based on a measurement carried out in the same manner as in Example 1, the total pore volume was 0.168 cm$^3$/g.
(Pore Distribution)
Based on a measurement carried out in the same manner as in Example 1, the pore volume ratio of pores having a pore size of less than 60 nm was 8.8%, and the pore volume ratio of pores having a pore size exceeding 120 nm was 0.4%.
(Calculation of Average Pore Size)
Based on a measurement carried out in the same manner as in Example 1, the average pore size was 84 nm.
(Measurement of Crystallite Size)
Based on a measurement carried out in the same manner as in Example 1, the crystallite size was 156 nm.
(Ammoxidation Reaction of Propane)
Propane was subjected to a vapor-phase ammoxidation reaction by the following method using the oxide catalyst obtained above. 35 g of the oxide catalyst was packed in a Vycor glass fluidized bed-type reaction tube having an inner diameter of 25 mm; and a mixed gas of propane:ammonia:oxygen:helium=1:1:3:18 in molar ratio was supplied for a contact time of 2.8 (sec·g/cc) at a reaction temperature of 440° C. under a reaction pressure of normal pressure. The ratio of propane conversion after the reaction was 89.2%, the yield of acrylonitrile was 54.0%, and the ammonia combustion rate was 19.2%.

Example 14

(Preparation of Niobium Raw Material Solution)
A niobium raw material solution was prepared in the same manner as in Example 1.
(Formulation of Raw Material-prepared Solution in a Formulation Tank)
19.9 kg of ammonium heptamolybdate [$(NH_4)_6Mo_7O_{24} \cdot 4H_2O$], 2.75 kg of ammonium metavanadate [$NH_4VO_3$], 3.28 kg of diantimony trioxide [$Sb_2O_3$], and further an aqueous solution of cerium nitrate in which 495 g of cerium nitrate [$Ce(NO_3)_3 \cdot 6H_2O$] was dissolved in 2 kg of water were added to 100 kg of water, and heated under stirring for one hour at 95° C., thereby obtaining a raw material-prepared solution (I).
2.28 kg of a hydrogen peroxide solution containing 30% by mass of $H_2O_2$ was added to 15.95 kg of the niobium raw-material solution. The mixture was stirred and mixed at a solution temperature being kept at about 20° C., thereby obtaining a raw material-prepared solution (II).
The obtained raw material-prepared solution (I) was cooled to 70° C., and 31.0 kg of silica sol containing 30.2% by mass of $SiO_2$ and having an average primary particle size of 23 nm and 6.80 kg of silica sol containing 30.0% by mass of $SiO_2$ and having an average primary particle size of 13 nm were added. Then, 3.80 kg of a hydrogen peroxide solution containing 30% by mass of $H_2O_2$ was added, and stirred and mixed for 30 minutes at 55° C. Thereafter, the raw material-prepared solution (II) and 516 g of an aqueous solution of ammonium metatungstate (50% purity) were added. Further, 8.60 kg of a silica powder was dispersed in 77.4 kg of water, and the resultant mixture was aged as is for one hour at 50° C., thereby obtaining a raw material-prepared solution (III).
(Spray Drying of Raw Material-prepared Solution Obtained in Formulation Tank)
Air heated to 210° C. and 50° C. hot water adjusted to a feed rate of 80 kg/Hr were fed to a centrifugal spray dryer until the formulation of the raw material-prepared solution (III) was complete; and the dryer inlet temperature was preset to 210° C. and the outlet temperature to 120° C.
When the feed amount of the raw material-prepared solution fed to the spray dryer was adjusted so that the spray dryer feed temperature did not fluctuate, the feed amount was 100 kg/Hr. During this period, the outlet temperature was 120±5° C., and did not greatly fluctuate.
(Measurement of UV-visible Reflectance Spectrum)
The obtained dried product was sampled each day. 0.5 g from the obtained 10 samples was tested using a JASCO UV/VIS Spectrometer V-650 manufactured by JASCO Corporation over a range of 200 to 800 nm based on a diffuse reflection method. Spectralon manufactured by Labsphere was used as a baseline reference material. The maximum absorbance value was 1.02. The absorbance at 600 nm was 0.31 to 0.36. Since this was an absorbance for which high performance could be expected based on the description in Japanese Patent Laid-Open No. 2009-148749, all of the spray-dried product was used in the classification operation without sorting.
(Classification Operation)
The obtained dried product was classified using a sieve having a sieve opening of 25 μm to obtain a classified product. The content of particles 25 μm or smaller in the obtained classified product was 0.8% by mass, and the average particle size was 55 μm.
(Calcination of Classified Product)
The obtained classified product was flowed at a rate of 20 kg/hr through a cylindrical calcining tube made of SUS, having an inner diameter of 500 mm, a length of 3,500 mm, and a thickness of 20 mm that was provided with seven weir plates having a height of 150 mm so that the length of the heating furnace section was divided into eight equal sections. Under a nitrogen gas flow of 600 NL/min, the temperature of the heating furnace was adjusted so as to have a temperature profile in which the temperature was increased to 370° C. over about four hours and kept at 370° C. for three hours while the calcining tube was being rotated at 4 rpm, to subject the classified product to pre-stage calcination, thereby obtaining a pre-stage calcined product. Then, the pre-stage calcined product was flowed at a rate of 15 kg/hr through another calcining tube made of SUS having an inner diameter of 500 mm, a length of 3,500 mm, and a thickness of 20 mm that was provided with seven weir plates having a height of 150 mm so that the length of the heating section was divided into eight equal sections, while the calcining tube was being rotated at 4 rpm. At this time, while a portion of the pre-stage calcined product on the powder inlet side of the calcining tube (a portion not covered by the heating furnace) was being hammered once every five seconds from a height of 250 mm above the calcining tube in the direction perpendicular to the rotation axis by a hammering device equipped with a hammer having a mass of 14 kg with a hammering tip end made of SUS, and under a nitrogen gas flow of 500 NL/min, the temperature of the heating furnace was adjusted so as to have a temperature profile in which the temperature was increased to 670° C. at 2° C./rain, calcination was carried out at 670° C. for two hours, and the temperature was reduced at 1° C./min, to carry out a main calcination, thereby obtaining an oxide catalyst.
(Composition of Oxide Catalyst)
Analysis of the oxide catalyst showed that a metal oxide had a composition of $MoV_{0.21}Nb_{0.09}Sb_{0.20}W_{0.01}Ce_{0.01}$. Further, the support amount of silica was 47% by mass based on the total amount of the catalyst formed from a metal oxide and silica.

(Measurement of Specific Surface Area)

Based on a measurement carried out in the same manner as in Example 1, the specific surface area was 16.7 m$^2$/g.

(Removal of Protruding Objects)

Protruding objects were removed in the same manner as in Example 1.

(Total Pore Volume)

Based on a measurement carried out in the same manner as in Example 1, the total pore volume was 0.342 cm$^3$/g.

(Pore Distribution)

Based on a measurement carried out in the same manner as in Example 1, the pore volume ratio of pores having a pore size of less than 60 nm was 9.0%, and the pore volume ratio of pores having a pore size exceeding 120 nm was 0.3%.

(Calculation of average pore size)

Based on a measurement carried out in the same manner as in Example 1, the average pore size was 82 nm.

(Measurement of Crystallite Size)

Based on a measurement carried out in the same manner as in Example 1, the crystallite size was 52 nm.

(Ammoxidation Reaction of Propane)

Propane was subjected to a vapor-phase ammoxidation reaction by the following method using the oxide catalyst obtained above. 35 g of the oxide catalyst was packed in a Vycor glass fluidized bed-type reaction tube having an inner diameter of 25 mm; and a mixed gas of propane:ammonia:oxygen:helium=1:1:3:18 in molar ratio was supplied for a contact time of 2.8 (sec·g/cc) at a reaction temperature of 440° C. under a reaction pressure of normal pressure. The ratio of propane conversion after the reaction was 89.1%, the yield of acrylonitrile was 54.0%, and the ammonia combustion rate was 19.5%.

Example 15

(Preparation of Niobium Raw Material Solution)

A niobium raw material solution was prepared in the same manner as in Example 1.

(Formulation of Raw Material-prepared Solution in a Formulation Tank)

19.9 kg of ammonium heptamolybdate [(NH$_4$)$_6$Mo$_7$O$_{24}$·4H$_2$O], 2.75 kg of ammonium metavanadate [NH$_4$VO$_3$], 3.28 kg of diantimony trioxide [Sb$_2$O$_3$], and further an aqueous solution of cerium nitrate in which 495 g of cerium nitrate [Ce(NO$_3$)$_3$·6H$_2$O] was dissolved in 2 kg of water were added to 100 kg of water, and heated under stirring for one hour at 95° C., thereby obtaining a raw material-prepared solution (I).

2.28 kg of a hydrogen peroxide solution containing 30% by mass of H$_2$O$_2$ was added to 15.95 kg of the niobium raw-material solution. The mixture was stirred and mixed at a solution temperature being kept at about 20° C., thereby obtaining a raw material-prepared solution (II).

The obtained raw material-prepared solution (I) was cooled to 70° C., and 30.7 kg of silica sol containing 30.2% by mass of SiO$_2$ and having an average primary particle size of 25 nm and 7.1 kg of silica sol containing 30.0% by mass of SiO$_2$ and having an average primary particle size of 12 nm were added. Then, 3.80 kg of a hydrogen peroxide solution containing 30% by mass of H$_2$O$_2$ was added, and stirred and mixed for 30 minutes at 55° C. Thereafter, the raw material-prepared solution (II) and 516 g of an aqueous solution of ammonium metatungstate (50% purity) were added. Further, 8.60 kg of a silica powder was dispersed in 77.4 kg of water, and the resultant mixture was aged as is for one hour at 50° C., thereby obtaining a raw material-prepared solution (III).

(Spray Drying of Raw Material-prepared Solution Obtained in Formulation Tank)

Air heated to 210° C. and 0.50° C. hot water adjusted to a feed rate of 80 kg/Hr were fed to a centrifugal spray dryer until the formulation of the raw material-prepared solution (III) was complete; and the dryer inlet temperature was preset to 210° C. and the outlet temperature to 120° C.

When the feed amount of the raw material-prepared solution fed to the spray dryer was adjusted so that the spray dryer feed temperature did not fluctuate, the feed amount was 100 kg/Hr. During this period, the outlet temperature was 120±5° C., and did not greatly fluctuate.

(Measurement of UV-visible Reflectance Spectrum)

The obtained dried product was sampled each day. 0.5 g from the obtained 10 samples was tested using a JASCO UV/VIS Spectrometer V-650 manufactured by JASCO Corporation over a range of 200 to 800 nm based on a diffuse reflection method. Spectralon manufactured by Labsphere was used as a baseline reference material. The maximum absorbance value was 1.02. The absorbance at 600 nm was 0.31 to 0.36. Since this was an absorbance for which high performance could be expected based on the description in Japanese Patent Laid-Open No. 2009-148749, all of the spray-dried product was used in the classification operation without sorting.

(Classification Operation)

The obtained dried product was classified using a sieve having a sieve opening of 25 μm to obtain a classified product. The content of particles 25 μm or smaller in the obtained classified product was 0.8% by mass, and the average particle size was 55 μm.

(Calcination of Classified Product)

The obtained classified product was flowed at a rate of 20 kg/hr through a cylindrical calcining tube made of SUS, having an inner diameter of 500 mm, a length of 3,500 mm, and a thickness of 20 mm that was provided with seven weir plates having a height of 150 mm so that the length of the heating furnace section was divided into eight equal sections. Under a nitrogen gas flow of 600 NL/min, the temperature of the heating furnace was adjusted so as to have a temperature profile in which the temperature was increased to 370° C. over about four hours and kept at 370° C. for three hours while the calcining tube was being rotated at 4 rpm, to subject the classified product to pre-stage calcination, thereby obtaining a pre-stage calcined product. Then, the pre-stage calcined product was flowed at a rate of 15 kg/hr through another calcining tube made of SUS having an inner diameter of 500 mm, a length of 3,500 mm, and a thickness of 20 mm that was provided with seven weir plates having a height of 150 mm so that the length of the heating section was divided into eight equal sections, while the calcining tube was being rotated at 4 rpm. At this time, while a portion of the pre-stage calcined product on the powder inlet side of the calcining tube (a portion not covered by the heating furnace) was being hammered once every five seconds from a height of 250 mm above the calcining tube in the direction perpendicular to the rotation axis by a hammering device equipped with a hammer having a mass of 14 kg with a hammering tip end made of SUS, and under a nitrogen gas flow of 500 NL/min, the temperature of the heating furnace was adjusted so as to have a temperature profile in which the temperature was increased to 695° C. at 2° C./min, calcination was carried out at 695° C. for one hour, and the temperature was reduced at 1° C./min, to carry out a main calcination, thereby obtaining an oxide catalyst.

(Composition of Oxide Catalyst)

Analysis of the oxide catalyst showed that a metal oxide had a composition of $MoV_{0.21}Nb_{0.09}Sb_{0.20}W_{0.01}Ce_{0.01}$. Further, the support amount of silica was 47% by mass based on the total amount of the catalyst formed from a metal oxide and silica.

(Measurement of Specific Surface Area)

Based on a measurement carried out in the same manner as in Example 1, the specific surface area was 9.2 $m^2/g$.

(Removal of Protruding Objects)

Protruding objects were removed in the same manner as in Example 1.

(Total Pore Volume)

Based on a measurement carried out in the same manner as in Example 1, the total pore volume was 0.170 $cm^3/g$.

(Pore Distribution)

Based on a measurement carried out in the same manner as in Example 1, the pore volume ratio of pores having a pore size of less than 60 nm was 10.6%, and the pore volume ratio of pores having a pore size exceeding 120 nm was 0.3%.

(Calculation of Average Pore Size)

Based on a measurement carried out in the same manner as in Example 1, the average pore size was 74 nm.

(Measurement of Crystallite Size)

Based on a measurement carried out in the same manner as in Example 1, the crystallite size was 55 nm.

(Ammoxidation Reaction of Propane)

Propane was subjected to a vapor-phase ammoxidation reaction by the following method using the oxide catalyst obtained above. 35 g of the oxide catalyst was packed in a Vycor glass fluidized bed-type reaction tube having an inner diameter of 25 mm; and a mixed gas of propane:ammonia:oxygen:helium=1:1:3:18 in molar ratio was supplied for a contact time of 2.8 (sec·g/cc) at a reaction temperature of 440° C. under a reaction pressure of normal pressure. The ratio of propane conversion after the reaction was 89.1%, the yield of acrylonitrile was 54.1%, and the ammonia combustion rate was 19.3%.

Example 16

(Preparation of Niobium Raw Material Solution)

A niobium raw material solution was prepared in the same manner as in Example 1.

(Formulation of Raw Material-prepared Solution in a Formulation Tank)

19.9 kg of ammonium heptamolybdate $[(NH_4)_6Mo_7O_{24}\cdot 4H_2O]$, 2.75 kg of ammonium metavanadate $[NH_4VO_3]$, 3.28 kg of diantimony trioxide $[Sb_2O_3]$, and further an aqueous solution of cerium nitrate in which 495 g of cerium nitrate $[Ce(NO_3)_3\cdot 6H_2O]$ was dissolved in 2 kg of water were added to 100 kg of water, and heated under stirring for one hour at 95° C., thereby obtaining a raw material-prepared solution (I).

2.28 kg of a hydrogen peroxide solution containing 30% by mass of $H_2O_2$ was added to 15.95 kg of the niobium raw-material solution. The mixture was stirred and mixed at a solution temperature being kept at about 20° C., thereby obtaining a raw material-prepared solution (II).

The obtained raw material-prepared solution (I) was cooled to 70° C., and 56.4 kg of silica sol containing 30.2% by mass of $SiO_2$ and having an average primary particle size of 23 nm and 6.90 kg of silica sol containing 30.0% by mass of $SiO_2$ and having an average primary particle size of 13 nm were added. Then, 3.80 kg of a hydrogen peroxide solution containing 30% by mass of $H_2O_2$ was added, and stirred and mixed for 30 minutes at 55° C. Thereafter, the raw material-prepared solution (II) and 516 g of an aqueous solution of ammonium metatungstate (50% purity) were added. Then the resultant mixture was aged for one hour at 50° C., thereby obtaining a raw material-prepared solution (III).

(Spray Drying of Raw Material-prepared Solution Obtained in Formulation Tank)

Air heated to 210° C. and 50° C. hot water adjusted to a feed rate of 80 kg/Hr were fed to a centrifugal spray dryer until the formulation of the raw material-prepared solution (III) was complete; and the dryer inlet temperature was preset to 210° C. and the outlet temperature to 120° C.

When the feed amount of the raw material-prepared solution fed to the spray dryer was adjusted so that the spray dryer feed temperature did not fluctuate, the feed amount was 100 kg/Hr. During this period, the outlet temperature was 120±5° C., and did not greatly fluctuate.

(Measurement of UV-visible Reflectance Spectrum)

The obtained dried product was sampled each day. 0.5 g from the obtained 10 samples was tested using a JASCO UV/VIS Spectrometer V-650 manufactured by JASCO Corporation over a range of 200 to 800 nm based on a diffuse reflection method. Spectralon manufactured by Labsphere was used as a baseline reference material. The maximum absorbance value was 1.02. The absorbance at 600 nm was 0.31 to 0.36. Since this was an absorbance for which high performance could be expected based on the description in Japanese Patent Laid-Open No. 2009-148749, all of the spray-dried product was used in the classification operation without sorting.

(Classification Operation)

The obtained dried product was classified using a sieve having a sieve opening of 25 μm to obtain a classified product. The content of particles 25 μm or smaller in the obtained classified product was 0.8% by mass, and the average particle size was 55 μm.

(Calcination of Classified Product)

The obtained classified product was flowed at a rate of 20 kg/hr through a cylindrical calcining tube made of SUS, having an inner diameter of 500 mm, a length of 3,500 mm, and a thickness of 20 mm that was provided with seven weir plates having a height of 150 mm so that the length of the heating furnace section was divided into eight equal sections. Under a nitrogen gas flow of 600 NL/min, the temperature of the heating furnace was adjusted so as to have a temperature profile in which the temperature was increased to 370° C. over about four hours and kept at 370° C. for three hours while the calcining tube was being rotated at 4 rpm, to subject the classified product to pre-stage calcination, thereby obtaining a pre-stage calcined product. Then, the pre-stage calcined product was flowed at a rate of 15 kg/hr through another calcining tube made of SUS having an inner diameter of 500 mm, a length of 3,500 mm, and a thickness of 20 mm that was provided with seven weir plates having a height of 150 mm so that the length of the heating section was divided into eight equal sections, while the calcining tube was being rotated at 4 rpm. At this time, while a portion of the pre-stage calcined product on the powder inlet side of the calcining tube (a portion not covered by the heating furnace) was being hammered once every five seconds from a height of 250 mm above the calcining tube in the direction perpendicular to the rotation axis by a hammering device equipped with a hammer having a mass of 14 kg with a hammering tip end made of SUS, and under a nitrogen gas flow of 500 NL/min, the temperature of the heating furnace was adjusted so as to have a temperature profile in which the temperature was increased to 685° C. at 2° C./min, calcination was carried out at 685° C.

for two hours, and the temperature was reduced at 1° C./min, to carry out a main calcination, thereby obtaining an oxide catalyst.
(Composition of Oxide Catalyst)
Analysis of the oxide catalyst showed that a metal oxide had a composition of $MoV_{0.21}Nb_{0.09}Sb_{0.20}W_{0.01}Ce_{0.01}$. Further, the support amount of silica was 47% by mass based on the total amount of the catalyst formed from a metal oxide and silica.
(Measurement of Specific Surface Area)
Based on a measurement carried out in the same manner as in Example 1, the specific surface area was 10.2 m$^2$/g.
(Removal of Protruding Objects)
Protruding objects were removed in the same manner as in Example 1.
(Total Pore Volume)
Based on a measurement carried out in the same manner as in Example 1, the total pore volume was 0.184 cm$^3$/g.
(Pore Distribution)
Based on a measurement carried out in the same manner as in Example 1, the pore volume ratio of pores having a pore size of less than 60 nm was 9.6%, and the pore volume ratio of pores having a pore size exceeding 120 nm was 0.2%.
(Calculation of Average Pore Size)
Based on a measurement carried out in the same manner as in Example 1, the average pore size was 72 nm.
(Measurement of Crystallite Size)
Based on a measurement carried out in the same manner as in Example 1, the crystallite size was 98 nm.
(Ammoxidation Reaction of Propane)
Propane was subjected to a vapor-phase ammoxidation reaction by the following method using the oxide catalyst obtained above. 35 g of the oxide catalyst was packed in a Vycor glass fluidized bed-type reaction tube having an inner diameter of 25 mm; and a mixed gas of propane:ammonia:oxygen:helium=1:1:3:18 in molar ratio was supplied for a contact time of 2.8 (sec·g/cc) at a reaction temperature of 440° C. under a reaction pressure of normal pressure. The ratio of propane conversion after the reaction was 90.1%, the yield of acrylonitrile was 54.1%, and the ammonia combustion rate was 19.6%.

Example 17

(Preparation of Niobium Raw Material Solution)
A niobium raw material solution was prepared in the same manner as in Example 1.
(Formulation of Raw Material-prepared Solution in a Formulation Tank)
19.9 kg of ammonium heptamolybdate [$(NH_4)_6Mo_7O_{24}\cdot4H_2O$], 2.75 kg of ammonium metavanadate [$NH_4VO_3$], 3.28 kg of diantimony trioxide [$Sb_2O_3$], and further an aqueous solution of cerium nitrate in which 495 g of cerium nitrate [$Ce(NO_3)_3\cdot6H_2O$] was dissolved in 2 kg of water were added to 100 kg of water, and heated under stirring for one hour at 95° C., thereby obtaining a raw material-prepared solution (I).
2.28 kg of a hydrogen peroxide solution containing 30% by mass of $H_2O_2$ was added to 15.95 kg of the niobium raw-material solution. The mixture was stirred and mixed at a solution temperature being kept at about 20° C., thereby obtaining a raw material-prepared solution (II).
The obtained raw material-prepared solution (I) was cooled to 70° C., and 31.0 kg of silica sol containing 30.2% by mass of $SiO_2$ and having an average primary particle size of 23 nm and 6.80 kg of silica sol containing 30.0% by mass of $SiO_2$ and having an average primary particle size of 13 nm were added. Then, 3.80 kg of a hydrogen peroxide solution containing 30% by mass of $H_2O_2$ was added, and stirred and mixed for 30 minutes at 55° C. Thereafter, the raw material-prepared solution (II) and 516 g of an aqueous solution of ammonium metatungstate (50% purity) were added. Further, 8.60 kg of a silica powder was dispersed in 77.4 kg of water, and the resultant mixture was aged as is for one hour at 50° C., thereby obtaining a raw material-prepared solution (III).
(Spray Drying of Raw Material-prepared Solution Obtained in Formulation Tank)
Air heated to 210° C. and 50° C. hot water adjusted to a feed rate of 80 kg/Hr were fed to a centrifugal spray dryer until the formulation of the raw material-prepared solution (III) was complete; and the dryer inlet temperature was preset to 210° C. and the outlet temperature to 120° C.
When the feed amount of the raw material-prepared solution fed to the spray dryer was adjusted so that the spray dryer feed temperature did not fluctuate, the feed amount was 100 kg/Hr. During this period, the outlet temperature was 120±5° C., and did not greatly fluctuate.
(Measurement of UV-visible Reflectance Spectrum)
The obtained dried product was sampled each day. 0.5 g from the obtained 10 samples was tested using a JASCO UV/VIS Spectrometer V-650 manufactured by JASCO Corporation over a range of 200 to 800 nm based on a diffuse reflection method. Spectralon manufactured by Labsphere was used as a baseline reference material. The maximum absorbance value was 1.02. The absorbance at 600 nm was 0.31 to 0.36. Since this was an absorbance for which high performance could be expected based on the description in Japanese Patent Laid-Open No. 2009-148749, all of the spray-dried product was used in the classification operation without sorting.
(Classification Operation)
The obtained dried product was classified using a sieve having a sieve opening of 25 μm to obtain a classified product. The content of particles 25 μm or smaller in the obtained classified product was 0.8% by mass, and the average particle size was 55 μm.
(Calcination of Classified Product)
The obtained classified product was flowed at a rate of 20 kg/hr through a cylindrical calcining tube made of SUS, having an inner diameter of 500 mm, a length of 3,500 mm, and a thickness of 20 mm that was provided with seven weir plates having a height of 150 mm so that the length of the heating furnace section was divided into eight equal sections. Under a nitrogen gas flow of 600 NL/min, the temperature of the heating furnace was adjusted so as to have a temperature profile in which the temperature was increased to 370° C. over about four hours and kept at 370° C. for three hours while the calcining tube was being rotated at 4 rpm, to subject the classified product to pre-stage calcination, thereby obtaining a pre-stage calcined product. Then, the pre-stage calcined product was flowed at a rate of 15 kg/hr through another calcining tube made of SUS having an inner diameter of 500 mm, a length of 3,500 mm, and a thickness of 20 mm that was provided with seven weir plates having a height of 150 mm so that the length of the heating section was divided into eight equal sections, while the calcining tube was being rotated at 4 rpm. At this time, while a portion of the pre-stage calcined product on the powder inlet side of the calcining tube (a portion not covered by the heating furnace) was being hammered once every five seconds from a height of 250 mm above the calcining tube in the direction perpendicular to the rotation axis by a hammering device equipped with a hammer having a mass of 14 kg with a hammering tip end made of SUS, and under a nitrogen gas flow of 500 NL/min, the temperature of the heating furnace was adjusted so as to have a temperature profile in which the temperature was increased to 550° C. at 2° C./min, calcination was carried out at 550° C. for two hours, and the temperature was reduced at 1° C./min, to carry out a main calcination, thereby obtaining an oxide catalyst.

(Composition of Oxide Catalyst)

Analysis of the oxide catalyst showed that a metal oxide had a composition of $MoV_{0.21}Nb_{0.09}Sb_{0.20}W_{0.01}Ce_{0.01}$. Further, the support amount of silica was 47% by mass based on the total amount of the catalyst formed from a metal oxide and silica.

(Measurement of Specific Surface Area)

Based on a measurement carried out in the same manner as in Example 1, the specific surface area was 17.4 $m^2/g$.

(Removal of Protruding Objects)

Protruding objects were removed in the same manner as in Example 1.

(Total Pore Volume)

Based on a measurement carried out in the same manner as in Example 1, the total pore volume was 0.270 $cm^3/g$.

(Pore Distribution)

Based on a measurement carried out in the same manner as in Example 1, the pore volume ratio of pores having a pore size of less than 60 nm was 31.2%, and the pore volume ratio of pores having a pore size exceeding 120 nm was 0.1%.

(Calculation of Average Pore Size)

Based on a measurement carried out in the same manner as in Example 1, the average pore size was 62 nm.

(Measurement of Crystallite Size)

Based on a measurement carried out in the same manner as in Example 1, the crystallite size was 44 nm.

(Ammoxidation Reaction of Propane)

Propane was subjected to a vapor-phase ammoxidation reaction by the following method using the oxide catalyst obtained above. 35 g of the oxide catalyst was packed in a Vycor glass fluidized bed-type reaction tube having an inner diameter of 25 mm; and a mixed gas of propane:ammonia:oxygen:helium=1:1:3:18 in molar ratio was supplied for a contact time of 2.8 (sec·g/cc) at a reaction temperature of 440° C. under a reaction pressure of normal pressure. The ratio of propane conversion after the reaction was 90.1%, the yield of acrylonitrile was 53.8%, and the ammonia combustion rate was 19.8%.

Comparative Example 1

(Preparation of Niobium Raw Material Solution)

A niobium raw material solution was prepared in the same manner as in Example 1.

(Formulation of Raw Material-prepared Solution in a Formulation Tank)

21.0 kg of ammonium heptamolybdate [$(NH_4)_6Mo_7O_{24}·4H_2O$], 2.91 kg of ammonium metavanadate [$NH_4VO_3$], 3.46 kg of diantimony trioxide [$Sb_2O_3$], and further an aqueous solution of cerium nitrate in which 524 g of cerium nitrate [$Ce(NO_3)_3·6H_2O$] was dissolved in 2 kg of water were added to 100 kg of water, and heated under stirring for one hour at 95° C., thereby obtaining a raw material-prepared solution (I).

134 g of a hydrogen peroxide solution containing 30% by mass of $H_2O_2$ was added to 937 g of the niobium raw-material solution. The mixture was stirred and mixed at a solution temperature being kept at about 20° C., thereby obtaining a raw material-prepared solution (II).

The obtained raw material-prepared solution (I) was cooled to 70° C., and 31.0 kg of silica sol containing 30.2% by mass of $SiO_2$ and having an average primary particle size of 26 nm and 6.80 kg of silica sol containing 30.0% by mass of $SiO_2$ and having an average primary particle size of 16 nm were added. Then, 4.02 kg of a hydrogen peroxide solution containing 30% by mass of $H_2O_2$ was added, and stirred and mixed for 30 minutes at 55° C. Thereafter, the raw material-prepared solution (II) and 523 g of an aqueous solution of ammonium metatungstate (50% purity) were added. Further, 8.60 kg of a silica powder was dispersed in 77.4 kg of water, and the resultant mixture was aged as is for one hour at 50° C., thereby obtaining a raw material-prepared solution (III).

(Spray Drying of Raw Material-prepared Solution Obtained in Formulation Tank)

Air heated to 210° C. and 50° C. hot water adjusted to a feed rate of 80 kg/Hr were fed to a centrifugal spray dryer until the formulation of the raw material-prepared solution (III) was complete; and the dryer inlet temperature was preset to 210° C. and the outlet temperature to 120° C.

When the feed amount of the raw material-prepared solution fed to the spray dryer was adjusted so that the spray dryer feed temperature did not fluctuate, the feed amount was 100 kg/Hr. During this period, the outlet temperature was 120±5° C., and did not greatly fluctuate.

(Measurement of UV-visible Reflectance Spectrum)

The obtained dried product was sampled each day. 0.5 g from the obtained 10 samples was tested using a JASCO UV/VIS Spectrometer V-650 manufactured by JASCO Corporation over a range of 200 to 800 nm based on a diffuse reflection method. Spectralon manufactured by Labsphere was used as a baseline reference material. The maximum absorbance value was 1.02. The absorbance at 600 nm was 0.31 to 0.36. Since this was an absorbance for which high performance could be expected based on the description in Japanese Patent Laid-Open No. 2009-148749, all of the spray-dried product was used in the classification operation without sorting.

(Classification Operation)

The obtained dried product was classified using a sieve having a sieve opening of 25 μm to obtain a classified product. The content of particles 25 μm or smaller in the obtained classified product was 0.8% by mass, and the average particle size was 55 μm.

(Calcination of Classified Product)

Classified products were calcined in the same manner as in Example 2.

(Composition of Oxide Catalyst)

Analysis of the oxide catalyst showed that a metal oxide had a composition of $MoV_{0.60}Nb_{0.005}Sb_{0.30}W_{0.01}Ce_{0.01}$. Further, the support amount of silica was 47% by mass based on the total amount of the catalyst formed from a metal oxide and silica.

(Measurement of Specific Surface Area)

Based on a measurement carried out in the same manner as in Example 1, the specific surface area was 14.6 $m^2/g$.

(Removal of Protruding Objects)

Protruding objects were removed in the same manner as in Example 1.

(Total Pore Volume)

Based on a measurement carried out in the same manner as in Example 1, the total pore volume was 0.329 $cm^3/g$.

(Pore Distribution)

Based on a measurement carried out in the same manner as in Example 1, the pore volume ratio of pores having a pore size of less than 60 nm was 8.9%, and the pore volume ratio of pores having a pore size exceeding 120 nm was 0.4%.

(Calculation of Average Pore Size)

Based on a measurement carried out in the same manner as in Example 1, the average pore size was 90 nm.

(Measurement of Crystallite Size)

Based on a measurement carried out in the same manner as in Example 1, the crystallite size was 120 nm.

(Ammoxidation Reaction of Propane)

Propane was subjected to a vapor-phase ammoxidation reaction by the following method using the oxide catalyst obtained above. 35 g of the oxide catalyst was packed in a Vycor glass fluidized bed-type reaction tube having an inner diameter of 25 mm; and a mixed gas of propane:ammonia:oxygen:helium=1:1:3:18 in molar ratio was supplied for a contact time of 2.8 (sec·g/cc) at a reaction temperature of 440° C. under a reaction pressure of normal pressure. The ratio of propane conversion after the reaction was 87.5%, the yield of acrylonitrile was 51.5%, and the ammonia combustion rate was 21.1%.

Comparative Example 2

(Preparation of Niobium Raw Material Solution)

A niobium raw material solution was prepared in the same manner as in Example 1.

(Formulation of Raw Material-prepared Solution in a Formulation Tank)

19.9 kg of ammonium heptamolybdate [$(NH_4)_6Mo_7O_{24}\cdot4H_2O$], 2.75 kg of ammonium metavanadate [$NH_4VO_3$], 3.28 kg of diantimony trioxide [$Sb_2O_3$], and further an aqueous solution of cerium nitrate in which 495 g of cerium nitrate [$Ce(NO_3)_3\cdot6H_2O$] was dissolved in 2 kg of water were added to 100 kg of water, and heated under stirring for one hour at 95° C., thereby obtaining a raw material-prepared solution (I).

2.28 kg of a hydrogen peroxide solution containing 30% by mass of $H_2O_2$ was added to 15.95 kg of the niobium raw-material solution. The mixture was stirred and mixed at a solution temperature being kept at about 20° C., thereby obtaining a raw material-prepared solution (II).

The obtained raw material-prepared solution (I) was cooled to 70° C., and 31.0 kg of silica sol containing 30.2% by mass of $SiO_2$ and having an average primary particle size of 108 nm and 6.80 kg of silica sol containing 30.0% by mass of $SiO_2$ and having an average primary particle size of 16 nm were added. Then, 3.80 kg of a hydrogen peroxide solution containing 30% by mass of $H_2O_2$ was added, and stirred and mixed for 30 minutes at 55° C. Thereafter, the raw material-prepared solution (II) and 516 g of an aqueous solution of ammonium metatungstate (50% purity) were added. Further, 8.60 kg of a silica powder was dispersed in 77.4 kg of water, and the resultant mixture was aged as is for one hour at 50° C., thereby obtaining a raw material-prepared solution (III).

(Spray Drying of Raw Material-prepared Solution Obtained in Formulation Tank)

Air heated to 210° C. and 50° C. hot water adjusted to a feed rate of 80 kg/Hr were fed to a centrifugal spray dryer until the formulation of the raw material-prepared solution (III) was complete; and the dryer inlet temperature was preset to 210° C. and the outlet temperature to 120° C.

When the feed amount of the raw material-prepared solution fed to the spray dryer was adjusted so that the spray dryer feed temperature did not fluctuate, the feed amount was 100 kg/Hr. During this period, the outlet temperature was 120±5° C., and did not greatly fluctuate.

(Measurement of UV-visible Reflectance Spectrum)

The obtained dried product was sampled each day. 0.5 g from the obtained 10 samples was tested using a JASCO UV/VIS Spectrometer V-650 manufactured by JASCO Corporation over a range of 200 to 800 nm based on a diffuse reflection method. Spectralon manufactured by Labsphere was used as a baseline reference material. The maximum absorbance value was 1.02. The absorbance at 600 nm was 0.31 to 0.36. Since this was an absorbance for which high performance could be expected based on the description in Japanese Patent Laid-Open No. 2009-148749, all of the spray-dried product was used in the classification operation without sorting.

(Classification Operation)

The obtained dried product was classified using a sieve having a sieve opening of 25 μm to obtain a classified product. The content of particles 25 μm or smaller in the obtained classified product was 0.8% by mass, and the average particle size was 55 μm.

(Calcination of Classified Product)

Classified products were calcined in the same manner as in Example 2.

(Composition of Oxide Catalyst)

Analysis of the oxide catalyst showed that a metal oxide had a composition ratio of $MoV_{0.21}Nb_{0.09}Sb_{0.20}W_{0.01}Ce_{0.01}$. Further, the support amount of silica was 47% by mass based on the total amount of the catalyst formed from a metal oxide and silica.

(Measurement of Specific Surface Area)

Based on a measurement carried out in the same manner as in Example 1, the specific surface area was 14.0 $m^2/g$.

(Removal of Protruding Objects)

Protruding objects were removed in the same manner as in Example 1.

(Total Pore Volume)

Based on a measurement carried out in the same manner as in Example 1, the total pore volume was 0.543 $cm^3/g$.

(Pore Distribution)

Based on a measurement carried out in the same manner as in Example 1, the pore volume ratio of pores having a pore size of less than 60 nm was 1.3%, and the pore volume ratio of pores having a pore size exceeding 120 nm was 3.2%.

(Calculation of Average Pore Size)

Based on a measurement carried out in the same manner as in Example 1, the average pore size was 155 nm.

(Measurement of Crystallite Size)

Based on a measurement carried out in the same manner as in Example 1, the crystallite size was 105 nm.

(Ammoxidation Reaction of Propane)

Propane was subjected to a vapor-phase ammoxidation reaction by the following method using the oxide catalyst obtained above. 35 g of the oxide catalyst was packed in a Vycor glass fluidized bed-type reaction tube having an inner diameter of 25 mm; and a mixed gas of propane:ammonia:oxygen:helium=1:1:3:18 in molar ratio was supplied for a contact time of 2.8 (sec·g/cc) at a reaction temperature of 440° C. under a reaction pressure of normal pressure. The ratio of propane conversion after the reaction was 86.9%, the yield of acrylonitrile was 52.6%, and the ammonia combustion rate was 19.3%.

Comparative Example 3

(Preparation of Niobium Raw Material Solution)

A niobium raw material solution was prepared in the same manner as in Example 1.

(Formulation of Raw Material-prepared Solution in a Formulation Tank)

19.9 kg of ammonium heptamolybdate [$(NH_4)_6Mo_7O_{24}\cdot4H_2O$], 2.75 kg of ammonium metavanadate [NH$_4$VO$_3$], 3.28 kg of diantimony trioxide [Sb$_2$O$_3$], and further an aqueous solution of cerium nitrate in which 495 g of cerium nitrate [Ce(NO$_3$)$_3$.6H$_2$O] was dissolved in 2 kg of water were added to 100 kg of water, and heated under stirring for one hour at 95° C., thereby obtaining a raw material-prepared solution (I).

2.28 kg of a hydrogen peroxide solution containing 30% by mass of H$_2$O$_2$ was added to 15.95 kg of the niobium raw-material solution. The mixture was stirred and mixed at a solution temperature being kept at about 20° C., thereby obtaining a raw material-prepared solution (II).

The obtained raw material-prepared solution (I) was cooled to 70° C., and 31.0 kg of silica sol containing 30.2% by mass of SiO$_2$ and having an average primary particle size of 12 nm and 6.80 kg of silica sol containing 30.0% by mass of SiO$_2$ and having an average primary particle size of 5 nm were added. Then, 3.80 kg of a hydrogen peroxide solution containing 30% by mass of H$_2$O$_2$ was added, and stirred and mixed for 30 minutes at 55° C. Thereafter, the raw material-prepared solution (II) and 516 g of an aqueous solution of ammonium metatungstate (50% purity) were added. Further, 8.60 kg of a silica powder was dispersed in 77.4 kg of water, and the resultant mixture was aged as is for one hour at 50° C., thereby obtaining a raw material-prepared solution (III).

(Spray Drying of Raw Material-prepared Solution Obtained in Formulation Tank)

Air heated to 210° C. and 50° C. hot water adjusted to a feed rate of 80 kg/Hr were fed to a centrifugal spray dryer until the formulation of the raw material-prepared solution (III) was complete; and the dryer inlet temperature was preset to 210° C. and the outlet temperature to 120° C.

When the feed amount of the raw material-prepared solution fed to the spray dryer was adjusted so that the spray dryer feed temperature did not fluctuate, the feed amount was 100 kg/Hr. During this period, the outlet temperature was 120±5° C., and did not greatly fluctuate.

(Measurement of UV-visible Reflectance Spectrum)

The obtained dried product was sampled each day. 0.5 g from the obtained 10 samples was tested using a JASCO UV/VIS Spectrometer V-650 manufactured by JASCO Corporation over a range of 200 to 800 nm based on a diffuse reflection method. Spectralon manufactured by Labsphere was used as a baseline reference material. The maximum absorbance value was 1.02. The absorbance at 600 nm was 0.31 to 0.36. Since this was an absorbance for which high performance could be expected based on the description in Japanese Patent Laid-Open No. 2009-148749, all of the spray-dried product was used in the classification operation without sorting.

(Classification Operation)

The obtained dried product was classified using a sieve having a sieve opening of 25 μm to obtain a classified product. The content of particles 25 μm or smaller in the obtained classified product was 0.8% by mass, and the average particle size was 55 μm.

(Calcination of Classified Product)

Classified products were calcined in the same manner as in Example 2.

(Composition of Oxide Catalyst)

Analysis of the oxide catalyst showed that a metal oxide had a composition of MoV$_{0.21}$Nb$_{0.09}$Sb$_{0.20}$W$_{0.01}$Ce$_{0.01}$. Further, the support amount of silica was 47% by mass based on the total amount of the catalyst formed from a metal oxide and silica.

(Measurement of Specific Surface Area)

Based on a measurement carried out in the same manner as in Example 1, the specific surface area was 13.8 m$^2$/g.

(Removal of Protruding Objects)

Protruding objects were removed in the same manner as in Example 1.

(Total Pore Volume)

Based on a measurement carried out in the same manner as in Example 1, the total pore volume was 0.086 cm$^3$/g.

(Pore Distribution)

Based on a measurement carried out in the same manner as in Example 1, the pore volume ratio of pores having a pore size of less than 60 nm was 88.2%, and the pore volume ratio of pores having a pore size exceeding 120 nm was 0%.

(Calculation of Average Pore Size)

Based on a measurement carried out in the same manner as in Example 1, the average pore size was 25 nm.

(Measurement of Crystallite Size)

Based on a measurement carried out in the same manner as in Example 1, the crystallite size was 104 nm.

(Ammoxidation Reaction of Propane)

Propane was subjected to a vapor-phase ammoxidation reaction by the following method using the oxide catalyst obtained above. 35 g of the oxide catalyst was packed in a Vycor glass fluidized bed-type reaction tube having an inner diameter of 25 mm; and a mixed gas of propane:ammonia:oxygen:helium=1:1:3:18 in molar ratio was supplied for a contact time of 2.8 (sec·g/cc) at a reaction temperature of 440° C. under a reaction pressure of normal pressure. The ratio of propane conversion after the reaction was 87.1%, the yield of acrylonitrile was 53.1%, and the ammonia combustion rate was 22.6%.

Comparative Example 4

(Preparation of Niobium Raw Material Solution)

A niobium raw material solution was prepared in the same manner as in Example 1.

(Formulation of Raw Material-prepared Solution in a Formulation Tank)

19.9 kg of ammonium heptamolybdate [(NH$_4$)$_6$Mo$_7$O$_{24}$.4H$_2$O], 2.75 kg of ammonium metavanadate [NH$_4$VO$_3$], 3.28 kg of diantimony trioxide [Sb$_2$O$_3$], and further an aqueous solution of cerium nitrate in which 495 g of cerium nitrate [Ce(NO$_3$)$_3$.6H$_2$O] was dissolved in 2 kg of water were added to 100 kg of water, and heated under stirring for one hour at 95° C., thereby obtaining a raw material-prepared solution (I).

2.28 kg of a hydrogen peroxide solution containing 30% by mass of H$_2$O$_2$ was added to 15.95 kg of the niobium raw-material solution. The mixture was stirred and mixed at a solution temperature being kept at about 20° C., thereby obtaining a raw material-prepared solution (II).

The obtained raw material-prepared solution (I) was cooled to 70° C., and 31.0 kg of silica sol containing 30.2% by mass of SiO$_2$ and having an average primary particle size of 110 nm and 6.80 kg of silica sol containing 30.0% by mass of SiO$_2$ and having an average primary particle size of 16 nm were added. Then, 3.80 kg of a hydrogen peroxide solution containing 30% by mass of H$_2$O$_2$ was added, and stirred and mixed for 30 minutes at 55° C. Thereafter, the raw material-prepared solution (II) and 516 g of an aqueous solution of ammonium metatungstate (50% purity) were added. Further, 8.60 kg of a silica powder was dispersed in 77.4 kg of water, and the resultant mixture was aged as is for one hour at 50° C., thereby obtaining a raw material-prepared solution (III).

(Spray Drying of Raw Material-prepared Solution Obtained in Formulation Tank)

Air heated to 210° C. and 50° C. hot water adjusted to a feed rate of 80 kg/Hr were fed to a centrifugal spray dryer until the formulation of the raw material-prepared solution (III) was complete; and the dryer inlet temperature was preset to 210° C. and the outlet temperature to 120° C.

When the feed amount of the raw material-prepared solution fed to the spray dryer was adjusted so that the spray dryer feed temperature did not fluctuate, the feed amount was 100 kg/Hr. During this period, the outlet temperature was 120±5° C., and did not greatly fluctuate.

(Measurement of UV-visible Reflectance Spectrum)

The obtained dried product was sampled each day. 0.5 g from the obtained 10 samples was tested using a JASCO UV/VIS Spectrometer V-650 manufactured by JASCO Corporation over a range of 200 to 800 nm based on a diffuse reflection method. Spectralon manufactured by Labsphere was used as a baseline reference material. The maximum absorbance value was 1.02. The absorbance at 600 nm was 0.31 to 0.36. Since this was an absorbance for which high performance could be expected based on the description in Japanese Patent Laid-Open No. 2009-148749, all of the spray-dried product was used in the classification operation without sorting.

(Classification Operation)

The obtained dried product was classified using a sieve having a sieve opening of 25 μm to obtain a classified product. The content of particles 25 μm or smaller in the obtained classified product was 0.8% by mass, and the average particle size was 55 μm.

(Calcination of Classified Product)

The obtained classified product was flowed at a rate of 20 kg/hr through a cylindrical calcining tube made of SUS, having an inner diameter of 500 mm, a length of 3,500 mm, and a thickness of 20 mm that was provided with seven weir plates having a height of 150 mm so that the length of the heating furnace section was divided into eight equal sections. Under a nitrogen gas flow of 600 NL/min, the temperature of the heating furnace was adjusted so as to have a temperature profile in which the temperature was increased to 370° C. over about four hours and kept at 370° C. for three hours while the calcining tube was being rotated at 4 rpm, to subject the classified product to pre-stage calcination, thereby obtaining a pre-stage calcined product. Then, the pre-stage calcined product was flowed at a rate of 15 kg/hr through another calcining tube made of SUS having an inner diameter of 500 mm, a length of 3,500 mm, and a thickness of 20 mm that was provided with seven weir plates having a height of 150 mm so that the length of the heating section was divided into eight equal sections, while the calcining tube was being rotated at 4 rpm. At this time, while a portion of the pre-stage calcined product on the powder inlet side of the calcining tube (a portion not covered by the heating furnace) was being hammered once every five seconds from a height of 250 mm above the calcining tube in the direction perpendicular to the rotation axis by a hammering device equipped with a hammer having a mass of 14 kg with a hammering tip end made of SUS, and under a nitrogen gas flow of 500 NL/min, the temperature of the heating furnace was adjusted so as to have a temperature profile in which the temperature was increased to 695° C. at 2° C./rain, calcination was carried out at 695° C. for four hours, and the temperature was reduced at 0.5° C./min, to carry out a main calcination, thereby obtaining an oxide catalyst.

(Composition of Oxide Catalyst)

Analysis of the oxide catalyst showed that a metal oxide had a composition ratio of $MoV_{0.21}Nb_{0.09}Sb_{0.20}W_{0.01}Ce_{0.01}$. Further, the support amount of silica was 47% by mass based on the total amount of the catalyst formed from a metal oxide and silica.

(Measurement of Specific Surface Area)

Based on a measurement carried out in the same manner as in Example 1, the specific surface area was 8.1 $m^2/g$.

(Removal of Protruding Objects)

Protruding objects were removed in the same manner as in Example 1.

(Total Pore Volume)

Based on a measurement carried out in the same manner as in Example 1, the total pore volume was 0.324 $cm^3/g$.

(Pore Distribution)

Based on a measurement carried out in the same manner as in Example 1, the pore volume ratio of pores having a pore size of less than 60 nm was 1.1%, and the pore volume ratio of pores having a pore size exceeding 120 nm was 3.8%.

(Calculation of Average Pore Size)

Based on a measurement carried out in the same manner as in Example 1, the average pore size was 160 nm.

(Measurement of Crystallite Size)

Based on a measurement carried out in the same manner as in Example 1, the crystallite size was 390 nm.

(Ammoxidation Reaction of Propane)

Propane was subjected to a vapor-phase ammoxidation reaction by the following method using the oxide catalyst obtained above. 35 g of the oxide catalyst was packed in a Vycor glass fluidized bed-type reaction tube having an inner diameter of 25 mm; and a mixed gas of propane:ammonia:oxygen:helium=1:1:3:18 in molar ratio was supplied for a contact time of 2.8 (sec·g/cc) at a reaction temperature of 440° C. under a reaction pressure of normal pressure. The ratio of propane conversion after the reaction was 85.9%, the yield of acrylonitrile was 52.2%, and the ammonia combustion rate was 20.1%.

Comparative Example 5

(Preparation of Niobium Raw Material Solution)

A niobium raw material solution was prepared in the same manner as in Example 1.

(Formulation of Raw Material-prepared Solution in a Formulation Tank)

19.9 kg of ammonium heptamolybdate $[(NH_4)_6Mo_7O_{24}.4H_2O]$, 2.75 kg of ammonium metavanadate $[NH_4VO_3]$, 3.28 kg of diantimony trioxide $[Sb_2O_3]$, and further an aqueous solution of cerium nitrate in which 495 g of cerium nitrate $[Ce(NO_3)_3.6H_2O]$ was dissolved in 2 kg of water were added to 100 kg of water, and heated under stirring for one hour at 95° C., thereby obtaining a raw material-prepared solution (I).

2.28 kg of a hydrogen peroxide solution containing 30% by mass of $H_2O_2$ was added to 15.95 kg of the niobium raw-material solution. The mixture was stirred and mixed at a solution temperature being kept at about 20° C., thereby obtaining a raw material-prepared solution (II).

The obtained raw material-prepared solution (I) was cooled to 70° C., and 31.0 kg of silica sol containing 30.2% by mass of $SiO_2$ and having an average primary particle size of 108 nm and 6.80 kg of silica sol containing 30.0% by mass of $SiO_2$ and having an average primary particle size of 16 nm were added. Then, 3.80 kg of a hydrogen peroxide solution containing 30% by mass of $H_2O_2$ was added, and stirred and mixed for 30 minutes at 55° C. Thereafter, the raw material-prepared solution (II) and 516 g of an aqueous solution of ammonium metatungstate (50% purity) were added. Further, 8.60 kg of a silica powder was dispersed in 77.4 kg of water, and the resultant mixture was aged as is for one hour at 50° C., thereby obtaining a raw material-prepared solution (III).

(Spray Drying of Raw Material-prepared Solution Obtained in Formulation Tank)

Air heated to 210° C. and 50° C. hot water adjusted to a feed rate of 80 kg/Hr were fed to a centrifugal spray dryer until the formulation of the raw material-prepared solution (III) was complete; and the dryer inlet temperature was preset to 210° C. and the outlet temperature to 120° C.

When the feed amount of the raw material-prepared solution fed to the spray dryer was adjusted so that the spray dryer feed temperature did not fluctuate, the feed amount was 100 kg/Hr. During this period, the outlet temperature was 120±5° C., and did not greatly fluctuate.

(Measurement of UV-visible Reflectance Spectrum)

The obtained dried product was sampled each day. 0.5 g from the obtained 10 samples was tested using a JASCO UV/VIS Spectrometer V-650 manufactured by JASCO Corporation over a range of 200 to 800 nm based on a diffuse reflection method. Spectralon manufactured by Labsphere was used as a baseline reference material. The maximum absorbance value was 1.02. The absorbance at 600 nm was 0.31 to 0.36. Since this was an absorbance for which high performance could be expected based on the description in Japanese Patent Laid-Open No. 2009-148749, all of the spray-dried product was used in the classification operation without sorting.

(Classification Operation)

The obtained dried product was classified using a sieve having a sieve opening of 25 μm to obtain a classified product. The content of particles 25 μm or smaller in the obtained classified product was 0.8% by mass, and the average particle size was 55 μm.

(Calcination of Classified Product)

The obtained classified product was flowed at a rate of 20 kg/hr through a cylindrical calcining tube made of SUS, having an inner diameter of 500 mm, a length of 3,500 mm, and a thickness of 20 mm that was provided with seven weir plates having a height of 150 mm so that the length of the heating furnace section was divided into eight equal sections. Under a nitrogen gas flow of 600 NL/min, the temperature of the heating furnace was adjusted so as to have a temperature profile in which the temperature was increased to 370° C. over about four hours and kept at 370° C. for three hours while the calcining tube was being rotated at 4 rpm, to subject the classified product to pre-stage calcination, thereby obtaining a pre-stage calcined product. Then, the pre-stage calcined product was flowed at a rate of 15 kg/hr through another calcining tube made of SUS having an inner diameter of 500 mm, a length of 3,500 mm, and a thickness of 20 mm that was provided with seven weir plates having a height of 150 mm so that the length of the heating section was divided into eight equal sections, while the calcining tube was being rotated at 4 rpm. At this time, while a portion of the pre-stage calcined product on the powder inlet side of the calcining tube (a portion not covered by the heating furnace) was being hammered once every five seconds from a height of 250 mm above the calcining tube in the direction perpendicular to the rotation axis by a hammering device equipped with a hammer having a mass of 14 kg with a hammering tip end made of SUS, and under a nitrogen gas flow of 500 NL/min, the temperature of the heating furnace was adjusted so as to have a temperature profile in which the temperature was increased to 670° C. at 2° C./rain, calcination was carried out at 670° C. for one hour, and the temperature was reduced at 2° C./min, to carry out a main calcination, thereby obtaining an oxide catalyst.

(Composition of Oxide Catalyst)

Analysis of the oxide catalyst showed that a metal oxide had a composition ratio of $MoV_{0.21}Nb_{0.09}Sb_{0.20}W_{0.01}Ce_{0.01}$. Further, the support amount of silica was 47% by mass based on the total amount of the catalyst formed from a metal oxide and silica.

(Measurement of Specific Surface Area)

Based on a measurement carried out in the same manner as in Example 1, the specific surface area was 16.2 $m^2/g$.

(Removal of Protruding Objects)

Protruding objects were removed in the same manner as in Example 1.

(Total Pore Volume)

Based on a measurement carried out in the same manner as in Example 1, the total pore volume was 0.559 $cm^3/g$.

(Pore Distribution)

Based on a measurement carried out in the same manner as in Example 1, the pore volume ratio of pores having a pore size of less than 60 nm was 2.3%, and the pore volume ratio of pores having a pore size exceeding 120 nm was 3.2%.

(Calculation of Average Pore Size)

Based on a measurement carried out in the same manner as in Example 1, the average pore size was 138 nm.

(Measurement of Crystallite Size)

Based on a measurement carried out in the same manner as in Example 1, the crystallite size was 20 nm.

(Ammoxidation Reaction of Propane)

Propane was subjected to a vapor-phase ammoxidation reaction by the following method using the oxide catalyst obtained above. 35 g of the oxide catalyst was packed in a Vycor glass fluidized bed-type reaction tube having an inner diameter of 25 mm; and a mixed gas of propane:ammonia:oxygen:helium=1:1:3:18 in molar ratio was supplied for a contact time of 2.8 (sec·g/cc) at a reaction temperature of 440° C. under a reaction pressure of normal pressure. The ratio of propane conversion after the reaction was 86.5%, the yield of acrylonitrile was 52.1%, and the ammonia combustion rate was 19.3%.

Comparative Example 6

(Preparation of Niobium Raw Material Solution)

A niobium raw material solution was prepared in the same manner as in Example 1.

(Formulation of Raw Material-prepared Solution in a Formulation Tank)

19.9 kg of ammonium heptamolybdate $[(NH_4)_6Mo_7O_{24}\cdot4H_2O]$, 2.75 kg of ammonium metavanadate $[NH_4VO_3]$, 3.28 kg of diantimony trioxide $[Sb_2O_3]$, and further an aqueous solution of cerium nitrate in which 495 g of cerium nitrate $[Ce(NO_3)_3\cdot6H_2O]$ was dissolved in 2 kg of water were added to 100 kg of water, and heated under stirring for one hour at 95° C., thereby obtaining a raw material-prepared solution (I).

2.28 kg of a hydrogen peroxide solution containing 30% by mass of $H_2O_2$ was added to 15.95 kg of the niobium raw-material solution. The mixture was stirred and mixed at a solution temperature being kept at about 20° C., thereby obtaining a raw material-prepared solution (II).

The obtained raw material-prepared solution (I) was cooled to 70° C., and 31.0 kg of silica sol containing 30.2% by mass of $SiO_2$ and having an average primary particle size of 12 nm and 6.80 kg of silica sol containing 30.0% by mass of $SiO_2$ and having an average primary particle size of 8 nm were added. Then, 3.80 kg of a hydrogen peroxide solution containing 30% by mass of $H_2O_2$ was added, and stirred and mixed for 30 minutes at 55° C. Thereafter, the raw material-prepared solution (II) and 516 g of an aqueous solution of ammonium metatungstate (50% purity) were added. Further, 8.60 kg of a silica powder was dispersed in 77.4 kg of water, and the resultant mixture was aged as is for one hour at 50° C., thereby obtaining a raw material-prepared solution (III).

(Spray Drying of Raw Material-prepared Solution Obtained in Formulation Tank)

Air heated to 210° C. and 50° C. hot water adjusted to a feed rate of 80 kg/Hr were fed to a centrifugal spray dryer until the formulation of the raw material-prepared solution (III) was complete; and the dryer inlet temperature was preset to 210° C. and the outlet temperature to 120° C.

When the feed amount of the raw material-prepared solution fed to the spray dryer was adjusted so that the spray dryer feed temperature did not fluctuate, the feed amount was 100 kg/Hr. During this period, the outlet temperature was 120±5° C., and did not greatly fluctuate.

(Measurement of UV-visible Reflectance Spectrum)

The obtained dried product was sampled each day. 0.5 g from the obtained 10' samples was tested using a JASCO UV/VIS Spectrometer V-650 manufactured by JASCO Corporation over a range of 200 to 800 nm based on a diffuse reflection method. Spectralon manufactured by Labsphere was used as a baseline reference material. The maximum absorbance value was 1.02. The absorbance at 600 nm was 0.31 to 0.36. Since this was an absorbance for which high performance could be expected based on the description in Japanese Patent Laid-Open No. 2009-148749, all of the spray-dried product was used in the classification operation without sorting.

(Classification Operation)

The obtained dried product was classified using a sieve having a sieve opening of 25 μm to obtain a classified product. The content of particles 25 μm or smaller in the obtained classified product was 0.8% by mass, and the average particle size was 55 μm.

(Calcination of Classified Product)

The obtained classified product was flowed at a rate of 20 kg/hr through a cylindrical calcining tube made of SUS, having an inner diameter of 500 mm, a length of 3,500 mm, and a thickness of 20 mm that was provided with seven weir plates having a height of 150 mm so that the length of the heating furnace section was divided into eight equal sections. Under a nitrogen gas flow of 600 NL/min, the temperature of the heating furnace was adjusted so as to have a temperature profile in which the temperature was increased to 370° C. over about four hours and kept at 370° C. for three hours while the calcining tube was being rotated at 4 rpm, to subject the classified product to pre-stage calcination, thereby obtaining a pre-stage calcined product. Then, the pre-stage calcined product was flowed at a rate of 15 kg/hr through another calcining tube made of SUS having an inner diameter of 500 mm, a length of 3,500 mm, and a thickness of 20 mm that was provided with seven weir plates having a height of 150 mm so that the length of the heating section was divided into eight equal sections, while the calcining tube was being rotated at 4 rpm. At this time, while a portion of the pre-stage calcined product on the powder inlet side of the calcining tube (a portion not covered by the heating furnace) was being hammered once every five seconds from a height of 250 mm above the calcining tube in the direction perpendicular to the rotation axis by a hammering device equipped with a hammer having a mass of 14 kg with a hammering tip end made of SUS, and under a nitrogen gas flow of 500 NL/min, the temperature of the heating furnace was adjusted so as to have a temperature profile in which the temperature was increased to 695° C. at 2° C./rain, calcination was carried out at 695° C. for four hours, and the temperature was reduced at 1° C./min, to carry out a main calcination, thereby obtaining an oxide catalyst.

(Composition of Oxide Catalyst)

Analysis of the oxide catalyst showed that a metal oxide had a composition ratio of $MoV_{0.21}Nb_{0.09}Sb_{0.20}W_{0.01}Ce_{0.01}$. Further, the support amount of silica was 47% by mass based on the total amount of the catalyst formed from a metal oxide and silica.

(Measurement of Specific Surface Area)

Based on a measurement carried out in the same manner as in Example 1, the specific surface area was 9.2 m$^2$/g.

(Removal of Protruding Objects)

Protruding objects were removed in the same manner as in Example 1.

(Total Pore Volume)

Based on a measurement carried out in the same manner as in Example 1, the total pore volume was 0.097 cm$^3$/g.

(Pore Distribution)

Based on a measurement carried out in the same manner as in Example 1, the pore volume ratio of pores having a pore size of less than 60 nm was 68.4%, and the pore volume ratio of pores having a pore size exceeding 120 nm was 0%.

(Calculation of Average Pore Size)

Based on a measurement carried out in the same manner as in Example 1, the average pore size was 42 nm.

(Measurement of Crystallite Size)

Based on a measurement carried out in the same manner as in Example 1, the crystallite size was 375 nm.

(Ammoxidation Reaction of Propane)

Propane was subjected to a vapor-phase ammoxidation reaction by the following method using the oxide catalyst obtained above. 35 g of the oxide catalyst was packed in a Vycor glass fluidized bed-type reaction tube having an inner diameter of 25 mm; and a mixed gas of propane:ammonia:oxygen:helium=1:1:3:18 in molar ratio was supplied for a contact time of 2.8 (sec·g/cc) at a reaction temperature of 440° C. under a reaction pressure of normal pressure. The ratio of propane conversion after the reaction was 87.0%, the yield of acrylonitrile was 52.3%, and the ammonia combustion rate was 23.1%.

Comparative Example 7

(Preparation of Niobium Raw Material Solution)

A niobium raw material solution was prepared in the same manner as in Example 1.

(Formulation of Raw Material-prepared Solution in a Formulation Tank)

19.9 kg of ammonium heptamolybdate [$(NH_4)_6Mo_7O_{24} \cdot 4H_2O$], 2.75 kg of ammonium metavanadate [$NH_4VO_3$], 3.28 kg of diantimony trioxide [$Sb_2O_3$], and further an aqueous solution of cerium nitrate in which 495 g of cerium nitrate [$Ce(NO_3)_3 \cdot 6H_2O$] was dissolved in 2 kg of water were added to 100 kg of water, and heated under stirring for one hour at 95° C., thereby obtaining a raw material-prepared solution (I).

2.28 kg of a hydrogen peroxide solution containing 30% by mass of $H_2O_2$ was added to 15.95 kg of the niobium raw-material solution. The mixture was stirred and mixed at a solution temperature being kept at about 20° C., thereby obtaining a raw material-prepared solution (II).

The obtained raw material-prepared solution (I) was cooled to 70° C., and 31.0 kg of silica sol containing 30.2% by mass of $SiO_2$ and having an average primary particle size of 10 nm and 6.80 kg of silica sol containing 30.0% by mass of $SiO_2$ and having an average primary particle size of 13 nm were added. Then, 3.80 kg of a hydrogen peroxide solution containing 30% by mass of $H_2O_2$ was added, and stirred and mixed for 30 minutes at 55° C. Thereafter, the raw material-prepared solution (II) and 516 g of an aqueous solution of ammonium metatungstate (50% purity) were added. Further, 8.60 kg of a silica powder was dispersed in 77.4 kg of water, and the resultant mixture was aged as is for one hour at 50° C., thereby obtaining a raw material-prepared solution (III).

(Spray Drying of Raw Material-prepared Solution Obtained in Formulation Tank)

Air heated to 210° C. and 50° C. hot water adjusted to a feed rate of 80 kg/Hr were fed to a centrifugal spray dryer until the formulation of the raw material-prepared solution (III) was complete; and the dryer inlet temperature was preset to 210° C. and the outlet temperature to 120° C.

When the feed amount of the raw material-prepared solution fed to the spray dryer was adjusted so that the spray dryer feed temperature did not fluctuate, the feed amount was 100 kg/Hr. During this period, the outlet temperature was 120±5° C., and did not greatly fluctuate.

(Measurement of UV-visible Reflectance Spectrum)

The obtained dried product was sampled each day. 0.5 g from the obtained 10 samples was tested using a JASCO UV/VIS Spectrometer V-650 manufactured by JASCO Corporation over a range of 200 to 800 nm based on a diffuse reflection method. Spectralon manufactured by Labsphere was used as a baseline reference material. The maximum absorbance value was 1.02. The absorbance at 600 nm was 0.31 to 0.36. Since this was an absorbance for which high performance could be expected based on the description in Japanese Patent Laid-Open No. 2009-148749, all of the spray-dried product was used in the classification operation without sorting.

(Classification Operation)

The obtained dried product was classified using a sieve having a sieve opening of 25 μm to obtain a classified product. The content of particles 25 μm or smaller in the obtained classified product was 0.8% by mass, and the average particle size was 55 μm.

(Calcination of Classified Product)

The obtained classified product was flowed at a rate of 20 kg/hr through a cylindrical calcining tube made of SUS, having an inner diameter of 500 mm, a length of 3,500 mm, and a thickness of 20 mm that was provided with seven weir plates having a height of 150 mm so that the length of the heating furnace section was divided into eight equal sections. Under a nitrogen gas flow of 600 NL/min, the temperature of the heating furnace was adjusted so as to have a temperature profile in which the temperature was increased to 370° C. over about four hours and kept at 370° C. for three hours while the calcining tube was being rotated at 4 rpm, to subject the classified product to pre-stage calcination, thereby obtaining a pre-stage calcined product. Then, the pre-stage calcined product was flowed at a rate of 15 kg/hr through another calcining tube made of SUS having an inner diameter of 500 mm, a length of 3,500 mm, and a thickness of 20 mm that was provided with seven weir plates having a height of 150 mm so that the length of the heating section was divided into eight equal sections, while the calcining tube was being rotated at 4 rpm. At this time, while a portion of the pre-stage calcined product on the powder inlet side of the calcining tube (a portion not covered by the heating furnace) was being hammered once every five seconds from a height of 250 mm above the calcining tube in the direction perpendicular to the rotation axis by a hammering device equipped with a hammer having a mass of 14 kg with a hammering tip end made of SUS, and under a nitrogen gas flow of 500 NL/min, the temperature of the heating furnace was adjusted so as to have a temperature profile in which the temperature was increased to 670° C. at 2° C./min, calcination was carried out at 670° C. for one hour, and the temperature was reduced at 1° C./min, to carry out a main calcination, thereby obtaining an oxide catalyst.

(Composition of Oxide Catalyst)

Analysis of the oxide catalyst showed that a metal oxide had a composition ratio of $MoV_{0.21}Nb_{0.09}Sb_{0.20}W_{0.01}Ce_{0.01}$. Further, the support amount of silica was 47% by mass based on the total amount of the catalyst formed from a metal oxide and silica.

(Measurement of Specific Surface Area)

Based on a measurement carried out in the same manner as in Example 1, the specific surface area was 20.3 m²/g.

(Removal of Protruding Objects)

Protruding objects were removed in the same manner as in Example 1.

(Total Pore Volume)

Based on a measurement carried out in the same manner as in Example 1, the total pore volume was 0.112 cm³/g.

(Pore Distribution)

Based on a measurement carried out in the same manner as in Example 1, the pore volume ratio of pores having a pore size of less than 60 nm was 91.4%, and the pore volume ratio of pores having a pore size exceeding 120 nm was 0%.

(Calculation of Average Pore Size)

Based on a measurement carried out in the same manner as in Example 1, the average pore size was 22 nm.

(Measurement of Crystallite Size)

Based on a measurement carried out in the same manner as in Example 1, the crystallite size was 24 nm.

(Ammoxidation Reaction of Propane)

Propane was subjected to a vapor-phase ammoxidation reaction by the following method using the oxide catalyst obtained above. 35 g of the oxide catalyst was packed in a Vycor glass fluidized bed-type reaction tube having an inner diameter of 25 mm; and a mixed gas of propane:ammonia:oxygen:helium=1:1:3:18 in molar ratio was supplied for a contact time of 2.8 (sec·g/cc) at a reaction temperature of 440° C. under a reaction pressure of normal pressure. The ratio of propane conversion after the reaction was 86.3.1%, the yield of acrylonitrile was 52.1%, and the ammonia combustion rate was 21.1%.

Comparative Example 8

(Preparation of Niobium Raw Material Solution)

A niobium raw material solution was prepared in the same manner as in Example 1.

(Formulation of Raw Material-prepared Solution in a Formulation Tank)

19.9 kg of ammonium heptamolybdate $[(NH_4)_6Mo_7O_{24} \cdot 4H_2O]$, 2.75 kg of ammonium metavanadate $[NH_4VO_3]$, 3.28 kg of diantimony trioxide $[Sb_2O_3]$, and further an aqueous solution of cerium nitrate in which 495 g of cerium nitrate $[Ce(NO_3)_3 \cdot 6H_2O]$ was dissolved in 2 kg of water were added to 100 kg of water, and heated under stirring for one hour at 95° C., thereby obtaining a raw material-prepared solution (I).

2.28 kg of a hydrogen peroxide solution containing 30% by mass of $H_2O_2$ was added to 15.95 kg of the niobium raw-material solution. The mixture was stirred and mixed at a solution temperature being kept at about 20° C., thereby obtaining a raw material-prepared solution (II).

The obtained raw material-prepared solution (I) was cooled to 70° C., and 31.0 kg of silica sol containing 30.2% by mass of SiO$_2$ and having an average primary particle size of 15 nm and 6.80 kg of silica sol containing 30.0% by mass of SiO$_2$ and having an average primary particle size of 5 nm were added. Then, 3.80 kg of a hydrogen peroxide solution containing 30% by mass of H$_2$O$_2$ was added, and stirred and mixed for 30 minutes at 55° C. Thereafter, the raw material-prepared solution (II) and 516 g of an aqueous solution of ammonium metatungstate (50% purity) were added. Further, 8.60 kg of a silica powder was dispersed in 77.4 kg of water, and the resultant mixture was aged as is for one hour at 50° C., thereby obtaining a raw material-prepared solution (III).

(Spray Drying of Raw Material-prepared Solution Obtained in Formulation Tank)

Air heated to 210° C. and 50° C. hot water adjusted to a feed rate of 80 kg/Hr were fed to a centrifugal spray dryer until the formulation of the raw material-prepared solution (III) was complete; and the dryer inlet temperature was preset to 210° C. and the outlet temperature to 120° C.

When the feed amount of the raw material-prepared solution fed to the spray dryer was adjusted so that the spray dryer feed temperature did not fluctuate, the feed amount was 100 kg/Hr. During this period, the outlet temperature was 120±5° C., and did not greatly fluctuate.

(Measurement of UV-visible Reflectance Spectrum)

The obtained dried product was sampled each day. 0.5 g from the obtained 10 samples was tested using a JASCO UV/VIS Spectrometer V-650 manufactured by JASCO Corporation over a range of 200 to 800 nm based on a diffuse reflection method. Spectralon manufactured by Labsphere was used as a baseline reference material. The maximum absorbance value was 1.02. The absorbance at 600 nm was 0.31 to 0.36. Since this was an absorbance for which high performance could be expected based on the description in Japanese Patent Laid-Open No. 2009-148749, all of the spray-dried product was used in the classification operation without sorting.

(Classification Operation)

The obtained dried product was classified using a sieve having a sieve opening of 25 μm to obtain a classified product. The content of particles 25 μm or smaller in the obtained classified product was 0.8% by mass, and the average particle size was 55 μm.

(Calcination of Classified Product)

The obtained classified product was flowed at a rate of 20 kg/hr through a cylindrical calcining tube made of SUS, having an inner diameter of 500 mm, a length of 3,500 mm, and a thickness of 20 mm that was provided with seven weir plates having a height of 150 mm so that the length of the heating furnace section was divided into eight equal sections. Under a nitrogen gas flow of 600 NL/min, the temperature of the heating furnace was adjusted so as to have a temperature profile in which the temperature was increased to 370° C. over about four hours and kept at 370° C. for three hours while the calcining tube was being rotated at 4 rpm, to subject the classified product to pre-stage calcination, thereby obtaining a pre-stage calcined product. Then, the pre-stage calcined product was flowed at a rate of 15 kg/hr through another calcining tube made of SUS having an inner diameter of 500 mm, a length of 3,500 mm, and a thickness of 20 mm that was provided with seven weir plates having a height of 150 mm so that the length of the heating section was divided into eight equal sections, while the calcining tube was being rotated at 4 rpm. At this time, while a portion of the pre-stage calcined product on the powder inlet side of the calcining tube (a portion not covered by the heating furnace) was being hammered once every five seconds from a height of 250 mm above the calcining tube in the direction perpendicular to the rotation axis by a hammering device equipped with a hammer having a mass of 14 kg with a hammering tip end made of SUS, and under a nitrogen gas flow of 500 NL/min, the temperature of the heating furnace was adjusted so as to have a temperature profile in which the temperature was increased to 700° C. at 2° C./min, calcination was carried out at 700° C. for two hours, and the temperature was reduced at 0.2° C./min, to carry out a main calcination, thereby obtaining an oxide catalyst.

(Composition of Oxide Catalyst)

Analysis of the oxide catalyst showed that a metal oxide had a composition ratio of MoV$_{0.21}$Nb$_{0.09}$Sb$_{0.20}$W$_{0.01}$Ce$_{0.01}$. Further, the support amount of silica was 47% by mass based on the total amount of the catalyst formed from a metal oxide and silica.

(Measurement of Specific Surface Area)

Based on a measurement carried out in the same manner as in Example 1, the specific surface area was 4.2 m$^2$/g.

(Removal of Protruding Objects)

Protruding objects were removed in the same manner as in Example 1.

(Total Pore Volume)

Based on a measurement carried out in the same manner as in Example 1, the total pore volume was 0.055 cm$^3$/g.

(Pore Distribution)

Based on a measurement carried out in the same manner as in Example 1, the pore volume ratio of pores having a pore size of less than 60 nm was 54.6%, and the pore volume ratio of pores having a pore size exceeding 120 nm was 0%.

(Calculation of Average Pore Size)

Based on a measurement carried out in the same manner as in Example 1, the average pore size was 52 nm.

(Measurement of Crystallite Size)

Based on a measurement carried out in the same manner as in Example 1, the crystallite size was 204 nm.

(Ammoxidation Reaction of Propane)

Propane was subjected to a vapor-phase ammoxidation reaction by the following method using the oxide catalyst obtained above. 35 g of the oxide catalyst was packed in a Vycor glass fluidized bed-type reaction tube having an inner diameter of 25 mm; and a mixed gas of propane:ammonia:oxygen:helium=1:1:3:18 in molar ratio was supplied for a contact time of 2.8 (sec·g/cc) at a reaction temperature of 440° C. under a reaction pressure of normal pressure. The ratio of propane conversion after the reaction was 86.2%, the yield of acrylonitrile was 50.6%, and the ammonia combustion rate was 22.8%.

Comparative Example 9

(Preparation of Niobium Raw Material Solution)

A niobium raw material solution was prepared in the same manner as in Example 1.

(Formulation of Raw Material-prepared Solution in a Formulation Tank)

19.9 kg of ammonium heptamolybdate [(NH$_4$)$_6$Mo$_7$O$_{24}$.4H$_2$O], 2.75 kg of ammonium metavanadate [NH$_4$VO$_3$], 3.28 kg of diantimony trioxide [Sb$_2$O$_3$], and further an aqueous solution of cerium nitrate in which 495 g of cerium nitrate [Ce(NO$_3$)$_3$.6H$_2$O] was dissolved in 2 kg of water were added to 100 kg of water, and heated under stirring for one hour at 95° C., thereby obtaining a raw material-prepared solution (I).

2.28 kg of a hydrogen peroxide solution containing 30% by mass of $H_2O_2$ was added to 15.95 kg of the niobium raw-material solution. The mixture was stirred and mixed at a solution temperature being kept at about 20° C., thereby obtaining a raw material-prepared solution (II).

The obtained raw material-prepared solution (I) was cooled to 70° C., and 34.7 kg of silica sol containing 30.2% by mass of $SiO_2$ and having an average primary particle size of 23 nm was added. Then, 3.80 kg of a hydrogen peroxide solution containing 30% by mass of $H_2O_2$ was added, and stirred and mixed for 30 minutes at 55° C. Thereafter, the raw material-prepared solution (II) and 516 g of an aqueous solution of ammonium metatungstate (50% purity) were added. Further, 8.60 kg of a silica powder was dispersed in 77.4 kg of water, and the resultant mixture was aged as is for one hour at 50° C., thereby obtaining a raw material-prepared solution (III).

(Spray Drying of Raw Material-prepared Solution Obtained in Formulation Tank)

Air heated to 210° C. and 50° C. hot water adjusted to a feed rate of 80 kg/Hr were fed to a centrifugal spray dryer until the formulation of the raw material-prepared solution (III) was complete; and the dryer inlet temperature was preset to 210° C. and the outlet temperature to 120° C.

When the feed amount of the raw material-prepared solution fed to the spray dryer was adjusted so that the spray dryer feed temperature did not fluctuate, the feed amount was 100 kg/Hr. During this period, the outlet temperature was 120±5° C., and did not greatly fluctuate.

(Measurement of UV-visible Reflectance Spectrum)

The obtained dried product was sampled each day. 0.5 g from the obtained 10 samples was tested using a JASCO UV/VIS Spectrometer V-650 manufactured by JASCO Corporation over a range of 200 to 800 nm based on a diffuse reflection method. Spectralon manufactured by Labsphere was used as a baseline reference material. The maximum absorbance value was 1.02. The absorbance at 600 nm was 0.31 to 0.36. Since this was an absorbance for which high performance could be expected based on the description in Japanese Patent Laid-Open No. 2009-148749, all of the spray-dried product was used in the classification operation without sorting.

(Classification Operation)

The obtained dried product was classified using a sieve having a sieve opening of 25 μm to obtain a classified product. The content of particles 25 μm or smaller in the obtained classified product was 0.8% by mass, and the average particle size was 55 μm.

(Calcination of Classified Product)

The obtained classified product was flowed at a rate of 20 kg/hr through a cylindrical calcining tube made of SUS, having an inner diameter of 500 mm, a length of 3,500 mm, and a thickness of 20 mm that was provided with seven weir plates having a height of 150 mm so that the length of the heating furnace section was divided into eight equal sections. Under a nitrogen gas flow of 600 NL/min, the temperature of the heating furnace was adjusted so as to have a temperature profile in which the temperature was increased to 370° C. over about four hours and kept at 370° C. for three hours while the calcining tube was being rotated at 4 rpm, to subject the classified product to pre-stage calcination, thereby obtaining a pre-stage calcined product. Then, the pre-stage calcined product was flowed at a rate of 15 kg/hr through another calcining tube made of SUS having an inner diameter of 500 mm, a length of 3,500 mm, and a thickness of 20 mm that was provided with seven weir plates having a height of 150 mm so that the length of the heating section was divided into eight equal sections, while the calcining tube was being rotated at 4 rpm. At this time, while a portion of the pre-stage calcined product on the powder inlet side of the calcining tube (a portion not covered by the heating furnace) was being hammered once every five seconds from a height of 250 mm above the calcining tube in the direction perpendicular to the rotation axis by a hammering device equipped with a hammer having a mass of 14 kg with a hammering tip end made of SUS, and under a nitrogen gas flow of 500 NL/min, the temperature of the heating furnace was adjusted so as to have a temperature profile in which the temperature was increased to 685° C. at 2° C./rain, calcination was carried out at 685° C. for two hours, and the temperature was reduced at 1° C./min, to carry out a main calcination, thereby obtaining an oxide catalyst.

(Composition of Oxide Catalyst)

Analysis of the oxide catalyst showed that a metal oxide had a composition of $MoV_{0.21}Nb_{0.09}Sb_{0.20}W_{0.01}Ce_{0.01}$. Further, the support amount of silica was 47% by mass based on the total amount of the catalyst formed from a metal oxide and silica.

(Measurement of Specific Surface Area)

Based on a measurement carried out in the same manner as in Example 1, the specific surface area was 15.1 $m^2$/g.

(Removal of Protruding Objects)

Protruding objects were removed in the same manner as in Example 1.

(Total Pore Volume)

Based on a measurement carried out in the same manner as in Example 1, the total pore volume was 0.174 $cm^3$/g.

(Pore Distribution)

Based on a measurement carried out in the same manner as in Example 1, the pore volume ratio of pores having a pore size of less than 60 nm was 63.8%, and the pore volume ratio of pores having a pore size exceeding 120 nm was 0%.

(Average Pore Size)

Based on a measurement carried out in the same manner as in Example 1, the average pore size was 46 nm.

(Measurement of Crystallite Size)

Based on a measurement carried out in the same manner as in Example 1, the crystallite size was 98 nm.

(Ammoxidation Reaction of Propane)

Propane was subjected to a vapor-phase ammoxidation reaction by the following method using the oxide catalyst obtained above. 35 g of the oxide catalyst was packed in a Vycor glass fluidized bed-type reaction tube having an inner diameter of 25 mm; and a mixed gas of propane:ammonia:oxygen:helium=1:1:3:18 in molar ratio was supplied for a contact time of 2.8 (sec·g/cc) at a reaction temperature of 440° C. under a reaction pressure of normal pressure. The ratio of propane conversion after the reaction was 90.1%, the yield of acrylonitrile was 53.1%, and the ammonia combustion rate was 22.3%.

The following Table 1 illustrates the composition and physical properties of the catalysts according to the respective examples and comparative examples, and the acrylonitrile yield and ammonia combustion rate.

TABLE 1

|  |  | Composition | | | | | Average Pore Size (nm) | Total Pore Volume (cm3/g) | Specific Surface Area (m2/g) | Crystallite (nm) | Acrylonitrile Yield (%) | Ammonia Combustion Rate (%) |
|---|---|---|---|---|---|---|---|---|---|---|---|---|
|  |  | V | Nb | X | T | Z |  |  |  |  |  |  |
| Example | 1 | 0.21 | 0.09 | Sb0.20 | W0.01 | Ce0.01 | 110 | 0.297 | 10.8 | 106 | 54.8 | 18.8 |
|  | 2 | 0.21 | 0.09 | Sb0.20 | W0.01 | Ce0.01 | 90 | 0.288 | 12.8 | 98 | 54.9 | 18.6 |
|  | 3 | 0.21 | 0.09 | Sb0.20 | W0.01 | Ce0.01 | 65 | 0.221 | 13.6 | 102 | 54.7 | 19.4 |
|  | 4 | 0.21 | 0.09 | Te0.20 | W0.01 | Ce0.01 | 92 | 0.235 | 10.2 | 185 | 54.8 | 19.0 |
|  | 5 | 0.21 | 0.09 | Sb0.20 | W0.005, Ti0.002 | Ce0.01 | 90 | 0.288 | 12.8 | 98 | 54.6 | 19.5 |
|  | 6 | 0.21 | 0.09 | Sb0.20 | W0.005, Mn0.003 | Ce0.01 | 92 | 0.304 | 13.2 | 101 | 54.7 | 19.3 |
|  | 7 | 0.21 | 0.09 | Sb0.20 | W0.003, Bi0.004 | Ce0.01 | 94 | 0.313 | 13.3 | 103 | 54.6 | 19.2 |
|  | 8 | 0.21 | 0.09 | Sb0.20 | W0.01 | Ce0.007, La0.003 | 90 | 0.320 | 14.2 | 95 | 54.6 | 18.8 |
|  | 9 | 0.21 | 0.09 | Sb0.20 | W0.01 | Ce0.008, Y0.002 | 91 | 0.330 | 14.5 | 102 | 54.7 | 18.9 |
|  | 10 | 0.21 | 0.09 | Sb0.20 | W0.01 | Ce0.006, Yb0.003 | 88 | 0.334 | 15.2 | 98 | 54.6 | 19.0 |
|  | 11 | 0.21 | 0.09 | Sb0.20 | W0.01 | Ce0.01 | 96 | 0.350 | 14.6 | 61 | 54.4 | 19.1 |
|  | 12 | 0.21 | 0.09 | Sb0.20 | W0.01 | Ce0.01 | 81 | 0.306 | 15.1 | 181 | 54.3 | 19.4 |
|  | 13 | 0.21 | 0.09 | Sb0.20 | W0.01 | Ce0.01 | 84 | 0.168 | 8.0 | 156 | 54.0 | 19.2 |
|  | 14 | 0.21 | 0.09 | Sb0.20 | W0.01 | Ce0.01 | 82 | 0.342 | 16.7 | 52 | 54.0 | 19.5 |
|  | 15 | 0.21 | 0.09 | Sb0.20 | W0.01 | Ce0.01 | 74 | 0.170 | 9.2 | 55 | 54.1 | 19.3 |
|  | 16 | 0.21 | 0.09 | Sb0.20 | W0.01 | Ce0.01 | 72 | 0.184 | 10.2 | 98 | 54.1 | 19.6 |
|  | 17 | 0.21 | 0.09 | Sb0.20 | W0.01 | Ce0.01 | 62 | 0.270 | 17.4 | 44 | 53.8 | 19.8 |
| Comparative Example | 1 | 0.21 | 0.005 | Sb0.20 | W0.01 | Ce0.01 | 90 | 0.329 | 14.6 | 120 | 51.5 | 21.1 |
|  | 2 | 0.21 | 0.09 | Sb0.20 | W0.01 | Ce0.01 | 155 | 0.543 | 14.0 | 105 | 52.6 | 19.3 |
|  | 3 | 0.21 | 0.09 | Sb0.20 | W0.01 | Ce0.01 | 25 | 0.086 | 13.8 | 104 | 53.1 | 22.6 |
|  | 4 | 0.21 | 0.09 | Sb0.20 | W0.01 | Ce0.01 | 160 | 0.324 | 8.1 | 390 | 52.2 | 20.1 |
|  | 5 | 0.21 | 0.09 | Sb0.20 | W0.01 | Ce0.01 | 138 | 0.559 | 16.2 | 20 | 52.1 | 19.3 |
|  | 6 | 0.21 | 0.09 | Sb0.20 | W0.01 | Ce0.01 | 42 | 0.097 | 9.2 | 375 | 52.3 | 23.1 |
|  | 7 | 0.21 | 0.09 | Sb0.20 | W0.01 | Ce0.01 | 22 | 0.112 | 20.3 | 24 | 52.1 | 21.1 |
|  | 8 | 0.21 | 0.09 | Sb0.20 | W0.01 | Ce0.01 | 52 | 0.055 | 4.2 | 204 | 50.6 | 22.8 |
|  | 9 | 0.21 | 0.09 | Sb0.20 | W0.01 | Ce0.01 | 46 | 0.174 | 15.1 | 98 | 53.1 | 22.3 |

The present application is based on a Japanese patent application filed with the Japan Patent Office on Apr. 21, 2011 (Japanese Patent Laid-Open No. 2011-095422), the contents of which are hereby incorporated in their entirety.

Industrial Applicability

The silica-supported catalyst according to the present invention has industrial applicability as a catalyst used when producing a corresponding unsaturated nitrile in a vapor-phase catalytic ammoxidation reaction of propane or isobutane.

What is claimed is:

1. A silica-supported catalyst used when producing a corresponding unsaturated nitrile in a vapor-phase catalytic ammoxidation reaction of propane or isobutane, the catalyst comprising a metal oxide represented by the following formula (1):

$$MoV_aNb_bX_cT_dZ_eO_n \qquad (1),$$

wherein X represents at least one or more elements selected from Sb and Te; T represents at least one or more elements selected from Ti, W, Mn, and Bi; Z represents at least one or more elements selected from La, Ce, Yb, and Y; and a, b, c, d, and e are in a range of $0.05 \leq a \leq 0.5$, $0.01 \leq b \leq 0.5$, $0.001 \leq c \leq 0.5$, $0 \leq d \leq 1$, and $0 \leq e \leq 1$, respectively, and n represents a value that satisfies an atomic valence, and wherein the silica-supported catalyst has an average pore size of 60 to 120 nm, a total pore volume of 0.15 cm$^3$/g or more, a specific surface area of 5 to 25 m$^2$/g, and a crystallite size of 40 to 250 nm as determined from half width of a (001) peak by X-ray diffraction.

2. The silica-supported catalyst according to claim 1, wherein a pore volume of pores having a pore size of less than 60 nm based on total pore volume is less than 30%, and a pore volume of pores having a pore size exceeding 120 nm based on total pore volume is less than 30%.

3. The silica-supported catalyst according to claim 1 or 2, wherein a support amount of the silica is 20 to 70% by mass based on total mass of the catalyst composed of the metal oxide and the silica.

4. A method for producing a silica-supported catalyst, comprising the steps of:
(I) preparing a raw material-prepared solution containing Mo, V, Nb, X, T, and Z, wherein X represents at least one or more elements selected from Sb and Te; T represents at least one or more elements selected from Ti, W, Mn, and Bi; Z represents at least one or more elements selected from La, Ce, Yb, and Y; an atomic ratio a of V to one Mo atom is $0.05 \leq a \leq 0.5$, an atomic ratio b of Nb to one Mo atom is $0.01 \leq b \leq 0.5$, an atomic ratio c of X to one Mo atom is $0.001 \leq c \leq 0.5$, an atomic ratio d of T to one Mo atom is $0 \leq d \leq 1$, and an atomic ratio e of Z to one Mo atom is $0 \leq e \leq 1$;
(II) drying the raw material-prepared solution to obtain a dry powder;
(III) pre-stage calcining the dry powder at 200 to 400° C. to obtain a pre-stage calcined body; and
(IV) main-calcining the pre-stage calcined body at 600 to 750° C. to obtain a calcined body,
wherein the raw material-prepared solution comprises:
0 to 30% by mass based on total mass of silica raw materials of (i) a silica sol having an average primary particle size of 3 nm or more and less than 20 nm;
30 to 70% by mass based on total mass of the silica raw materials of (ii) a silica sol having an average primary particle size of 20 nm or more and 100 nm or less; and
30 to 70% by mass based on total mass of the silica raw materials of a silica powder having an average primary particle size of 50 nm or less,
wherein a total of the silica sol (i), the silica sol (ii), and the silica powder is 100% by mass based on silica.

5. A method for producing a corresponding unsaturated nitrile by performing a vapor-phase catalytic ammoxidation reaction of propane or isobutane using a silica-supported catalyst, wherein the silica-supported catalyst comprises a metal oxide represented by the following formula (1):

$$Mo V_a Nb_b X_c T_d Z_e O_n \qquad (1),$$

wherein X represents at least one or more elements selected from Sb and Te; T represents at least one or more elements selected from Ti, W, Mn, and Bi; Z represents at least one or more elements selected from La, Ce, Yb, and Y; and a, b, c, d, and e are in a range of $0.05 \leq a \leq 0.5$, $0.01 \leq b \leq 0.5$, $0.001 \leq c \leq 0.5$, $0 \leq d \leq 1$, and $0 \leq e \leq 1$, respectively, and n represents a value that satisfies an atomic valence, and wherein the silica-supported catalyst has an average pore size of 60 to 120 nm, a total pore volume of 0.15 cm$^3$/g or more, a specific surface area of 5 to 25 m$^2$/g, and a crystallite size of 40 to 250 nm as determined from half width of a (001) peak by X-ray diffraction.

6. The method for producing a corresponding unsaturated nitrile according to claim 5, wherein a pore volume of pores having a pore size of less than 60 nm based on total pore volume is less than 30%, and a pore volume of pores having a pore size exceeding 120 nm based on total pore volume is less than 30%.

7. The method for producing a corresponding unsaturated nitrile according to claim 5, wherein a support amount of the silica is 20 to 70% by mass based on total mass of the catalyst composed of the metal oxide and the silica.

* * * * *